United States Patent
Blanchard et al.

(10) Patent No.: US 8,945,515 B2
(45) Date of Patent: Feb. 3, 2015

(54) METHODS AND COMPOSITIONS FOR ALTERING PHOTOPHYSICAL PROPERTIES OF FLUOROPHORES VIA PROXIMAL QUENCHING

(75) Inventors: Scott Blanchard, New York, NY (US); Roger Altman, New York, NY (US); J. David Warren, New York, NY (US)

(73) Assignee: Cornell University, Ithaca, NY (US)

( * ) Notice: Subject to any disclaimer, the term of this patent is extended or adjusted under 35 U.S.C. 154(b) by 54 days.

(21) Appl. No.: 13/202,351

(22) PCT Filed: Feb. 19, 2010

(86) PCT No.: PCT/US2010/024824
§ 371 (c)(1),
(2), (4) Date: Sep. 20, 2011

(87) PCT Pub. No.: WO2010/096720
PCT Pub. Date: Aug. 26, 2010

(65) Prior Publication Data
US 2012/0027689 A1 Feb. 2, 2012

Related U.S. Application Data

(60) Provisional application No. 61/153,871, filed on Feb. 19, 2009.

(51) Int. Cl.
*A61B 5/00* (2006.01)
*A61K 49/00* (2006.01)
*G01N 33/542* (2006.01)

(52) U.S. Cl.
CPC ......... *A61K 49/0052* (2013.01); *A61K 49/0041* (2013.01); *A61K 49/0067* (2013.01); *G01N 33/542* (2013.01); *A61K 49/0032* (2013.01)
USPC ....................................... 424/9.6

(58) Field of Classification Search
None
See application file for complete search history.

(56) References Cited

U.S. PATENT DOCUMENTS

2006/0099604 A1* 5/2006 Stevens et al. ............... 435/6
2008/0102036 A1 5/2008 Poss et al.

OTHER PUBLICATIONS

Rasnik et al. Nonblinking and long-lasting single-molecule fluorescence imaging. 2006 Nat. Methods 3: 891-893.*
Liu et al. Rational design and synthesis of a novel class of highly fluorescent rhodamine dyes that have strong absorption at long wavelengths. 2003 Tetrahedron Lett. 44: 4355-4359.*
Koopmans et al. Single-pair FRET microscopy reveals mononucleosome dynamics. 2007 J. Fluoresc. 17:785-795.*
Liphardt B. et al., "Laser Dyes With Intramolecular Triplet Quenching", *Optics Communications* 38(3):207-210 (Aug. 1, 1981).
Aitken C.E. et al., "An Oxygen Scavenging System for Improvement of Dye Stability in Single-Molecule Fluorescence Experiments", Biophysical Journal 94:1826-1835 (Mar. 2008).
Domanov Y., "Fluorescence Resonance Energy Transfer (FRET)-Actually Seeing Molecular Proximity", Graduate Course "Practical fluorescence techniques for life scientists", Helsinki (Oct. 2006).
Marshall R.A. et al., "Irreversible Chemical Steps Control Intersubunit Dynamics During Translation", PNAS 105 (40):15364-15369 (Oct. 7, 2008).
Tomschik M. et al., "Nucleosome Dynamics as Studied by Single-Pair Fluorescence Resonance Energy Transfer: A Reevaluation", J. Fluoresc 19:53-62 (2009).
International Search Report dated Sep. 16, 2010 received from the Korean Intellectual Property Office from related Application No. PCT/US2010/024824.
Written Opinion dated Sep. 16, 2010 received from the Korean Intellectual Property Office from related Application No. PCT/US2010/024824.

* cited by examiner

*Primary Examiner* — Michael G Hartley
*Assistant Examiner* — Jennifer Lamberski
(74) *Attorney, Agent, or Firm* — Scully, Scott, Murphy & Presser, P.C.

(57) ABSTRACT

The invention is directed to fluorophore-containing compositions and configurations wherein proximity between the fluorophore and one or more protective agents (PAs) modifies the lifetime of fluorescent and/or dark states, their frequency of occurrence, and the total lifetime of fluorescence in order to appropriately modify the photophysical characteristics of the fluorophore. The invention is also directed to methods that utilize these compositions and configurations.

7 Claims, 42 Drawing Sheets

Cy5-labeled DNA oligonucleotide showing characteristic blinking behavior mCherry (fluorescent protein variant) showing characteristic blinking behavior Quantum Dot (Q625-Invitrogen) showing characteristic blinking behavior.

cyclooctatetraene (COT)

Trolox nitrobenzyl alcohol (NBA)

Chloramphenicol

Commercial monoreactive NHS-Cy5

Commercial bisreactive NHS-Cy5

Commercial monoreactive
Mal-Cy5

Commercial bisreactive
Mal-Cy5

US 8,945,515 B2

METHODS AND COMPOSITIONS FOR ALTERING PHOTOPHYSICAL PROPERTIES OF FLUOROPHORES VIA PROXIMAL QUENCHING

CROSS REFERENCE TO RELATED APPLICATION

This application claims the benefit of priority from U.S. Provisional Application No. 61/153,871, filed on Feb. 19, 2009.

GOVERNMENT SUPPORT

This invention was made with government support under GM079238 awarded by the National Institutes of Health. The government has certain rights in the invention.

FIELD OF THE INVENTION

The present invention relates generally to fluorophore compositions, and more particularly, to fluorophore compositions in which a fluorescence property of the fluorophore is modified by another molecule.

BACKGROUND OF THE INVENTION

Fluorescence applications penetrate nearly every field of biological research and have more recently been proposed as a means for light-based computational applications by virtue of a single fluorophore's observed propensity to undergo a binary switch between fluorescent and dark states. In vitro and in vivo fluorescence measurements, as well as wide-field, scanning confocal, and Total Internal Reflection Fluorescence Microscopy (TIRE) used for whole cell and single-molecule imaging rely on high-quantum yield, stable fluorescent species such as those shown in FIG. 3.

However, the utility of such fluorophores, including organic dyes, fluorescent proteins, as well as inorganic quantum dots and nanocrystals, is limited by their intrinsic photophysical properties that lead to transient and/or permanent dark states. It is believed that these dark states arise via electronic transitions from the singlet ground and/or excited states to triplet dark states, as depicted by a simplified Jablonski diagram shown in FIG. 1. From triplet states, deleterious physical modifications or damage can occur to the dye.

For example, such processes tend to limit photon emission from the fluorophore including stochastic "blinking" events and irreversible photobleaching. Blinking and photobleaching phenomena occur in all fluorescence applications but are particularly pronounced in experiments demanding intense illumination, including confocal imaging of cells and single-molecule fluorescence methods.

In order to characterize the blinking and photobleaching behaviors adequately, individual fluorophores must be tracked as a function of time. Here, the application of modern single-molecule fluorescence methods is ideal. Single, fluorescing molecules can be easily tracked using total internal reflection (TIR) fluorescence methods where the fluorophore is spatially tethered near an optically-transparent surface and illuminated by a single-frequency laser light source, as shown, for example, in FIG. 2. In such an experimental setting, blinking and photobleaching appear as brief periods of fluorescence punctuated by long-lived non-fluorescing states, as shown, for example in FIG. 4. Although for some applications this switching behavior may be detrimental, this characteristic may be harnessed (e.g., appropriately adjusted, modified, or even enhanced) for such applications as super-resolution imaging, computational applications, and sensor technologies.

Compounds such as Trolox, p-nitrobenzyl alcohol (NBA), β-mercaptoethanol (BME), mercaptoethylamine (MEA), n-propyl gallate, 1,4-diazabicyclo[2.2.2]octane (DABCO), and cyclooctatetraene (COT) that favorably affect dark state and photobleaching lifetimes have come into increasingly widespread use as additives in solution-based experiments. However, the use of such protective agents in solution is limited by their solubility (Trolox, COT and NBA, in particular, are highly insoluble in aqueous solutions). Examples are shown in FIG. 5. Moreover, if beneficial outcomes are required for fluorescence imaging in cells, the protective agent's membrane permeability and potential toxicity must also be considered.

SUMMARY OF THE INVENTION

The present invention provides new fluorophore-containing compositions and configurations wherein the fluorophore is placed in proximity to one or more protective molecules (including triplet state quenchers (TSQs) that increase the rate of relaxation from the triplet dark state to the ground state), which modifies the effective time spent in dark states either by reducing their frequency of occurrence or their lifetime in order to appropriately modify the photophysical characteristics of the fluorophore. In particular, the proximity between the fluorophore and one or more protective agents can be adjusted in order to suitably adjust the time spent in fluorescent and/or dark states. In particular embodiments, adjustments in proximity are made in order to improve the total number of photons emitted from a single fluorophore prior to photobleaching and to increase or optimize the effective flux of photons generated by a single fluorophore per unit time. Thus, the present invention establishes a general chemical strategy where dye proximity to one or more protective agents can be used to favorably "tune" dye photophysics via the manipulation of dark state and fluorescent state lifetimes as schematized in FIG. 1.

Use of protective agents in solution as reported in the art is often limited by protective agent solubility and/or toxicity in applications involving cells. Such limitations are bypassed by the present invention where solubility considerations are circumnavigated by direct and/or indirect attachment of one or more protective agents to the dye molecule. Accordingly, excess protective agent in solution is not required. In addition, the present invention effectively circumvents unwanted photophysical dye behavior in both bulk and single-molecule contexts in the absence and presence of oxygen. In addition to improving the performance of dyes for fluorescence imaging experiments in vitro, this means of mitigating fluorophore photophysical processes can also be applied to in vivo fluorescence and FRET imaging at both the bulk and single-molecule scale. One embodiment of single-molecule imaging which demands high-illumination intensity and long-lived fluorescence employs a total internal reflection configuration such as that shown in FIG. 2. The present invention can also be applied to molecular imaging where increased illumination intensities are demanded for applications such as high-spatial and -time resolution measurements; cellular imaging where unwanted fluorophore photobleaching often limits the overall time and signal-to-noise ratio of the measurement; super-resolution imaging, which demands robust dye lifetime and blinking kinetics PCR; sequencing and microarray applications that have ever-increasing demands on sensitivity;

light-based computer applications where fluorophore photobleaching determines the lifetime of the photoswitch; medical imaging diagnostics based on fluorescence detection; as well as nanoparticles, such as quantum dots, impregnated with dye-protective agent conjugates.

In one embodiment, the invention is directed to a composition containing a fluorophore having attached thereto one or more protective agent moieties. If two or more protective agent moieties are included, they may be the same or different. The one or more protective agent moieties are attached covalently or non-covalently to the fluorophore either directly or via a spacer molecule.

In another embodiment, the invention is directed to a composition containing one or more fluorophores and one or more protective agent molecules, wherein the fluorophores are in close proximity to the protective agent such that the protective agent has an effect on the photophysical properties of the fluorophore. In this embodiment, the fluorophore and protective agent are not linked directly or through a linker. For example, in one embodiment, the fluorophore and protective agent are separately conjugated to a biomolecule, such as a protein, DNA, RNA, RNA-protein, DNA-protein, or protein-protein complex. In a particular embodiment, the protein is a fluorescent protein. In another embodiment, the fluorophore and protective agent are held proximal to each other by having the fluorophore and protective agent incorporated within different locations of a vesicle. In a further embodiment thereof, a biomolecule to be studied is encapsulated by the vesicle. In a further embodiment thereof, the biomolecule is fluorophore-conjugated, and the protective agent is within the membrane of the vesicle or on an inner surface or outer surface of the membrane. In another embodiment, the fluorophore and protective agent are held proximal to each other by having the fluorophore and protective agent on the surface or passivation shell of a nanoparticle. The nanoparticle can be, for example, a quantum dot. In yet another embodiment, the fluorophore and protective agent are held proximal to each other by having the fluorophore and protective agent attached to a surface of a bulk solid.

In another embodiment, the invention is directed to a method for performing single-molecule Fluorescence Resonance Energy Transfer (FRET). The method includes measuring the FRET efficiency of a labeled biomolecule containing a biomolecule attached to a donor fluorophore and acceptor fluorophore, wherein one or both of the fluorophores are attached covalently to one or more protective agent moieties, or one or both of the fluorophores are not linked to a protective agent, either directly or via a linker, but held proximal to one or more protective agents. In a particular embodiment thereof, the fluorophore-labeled biomolecule is encapsulated within a vesicle, and a protective agent is within a membrane of the vesicle or on an inner or outer surface of the membrane.

In yet another embodiment, the invention is directed to a method for tuning the photophysical properties of a fluorophore. The method includes analyzing the fluorescence properties of a consortium of fluorophores held at proximal distances to one or more protective agents, and identifying new protective agents by this analysis, and/or finding a fluorophore-protective agent composition with an optimal set of photophysical properties by this analysis.

In still another embodiment, the invention is directed to a method for detecting a cellular process. The method includes: (i) administering to the cell or animal a targeting probe that includes a biomolecule possessing a targeting portion thereon, at least one fluorophore, and at least one protective agent moiety, wherein the protective agent is in close enough proximity to the fluorophore such that the protective agent enhances or otherwise optimizes the photophysical properties of the fluorophore, and ii) detecting the targeting probe in the cell.

In further embodiments of any of the compositions and methods described above, the fluorophore is a "red-shifted fluorophore", i.e., by exhibiting an emission wavelength greater than 594 nm. Such fluorophores are particularly suitable for use in FRET, and particularly, smFRET methods.

BRIEF DESCRIPTION OF THE FIGURES

As shown in FIG. 9, the Cy5-Trolox conjugate (orange) is greatly improved in lifetime over the no-PA Cy5 control (>10-fold). By adding a second protective agent (either NBA and Trolox) in proximity (within 30Å) of the Cy5-Trolox fluorophore, an additional improvement in fluorophore lifetime ($t_{on}$) is observed. In the case of a Trolox (purple), the additional improvement is >1.3-fold. In the case of NBA (green) the additional improvement is >2-fold. Thus, the total improvement achieved was >20-fold over the parent compound. Drawings depicting other exemplary strategies for achieving proximity of more than one protective agent to a fluorescing species.

DETAILED DESCRIPTION OF THE INVENTION

Figure 1:
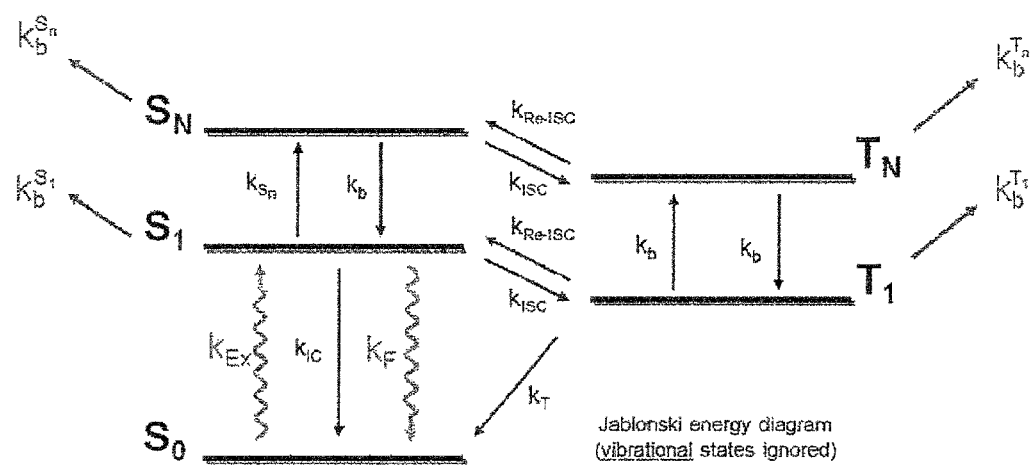
FIG. 1. Simplified Jablonski diagram describing competing kinetic pathways that dictate the photophysical properties of fluorescent molecular species. Shown here are the ground ($S_0$), singlet ($S_1$ and $S_N$), and triplet states ($T_1$ and $T_N$).
Figure 2:
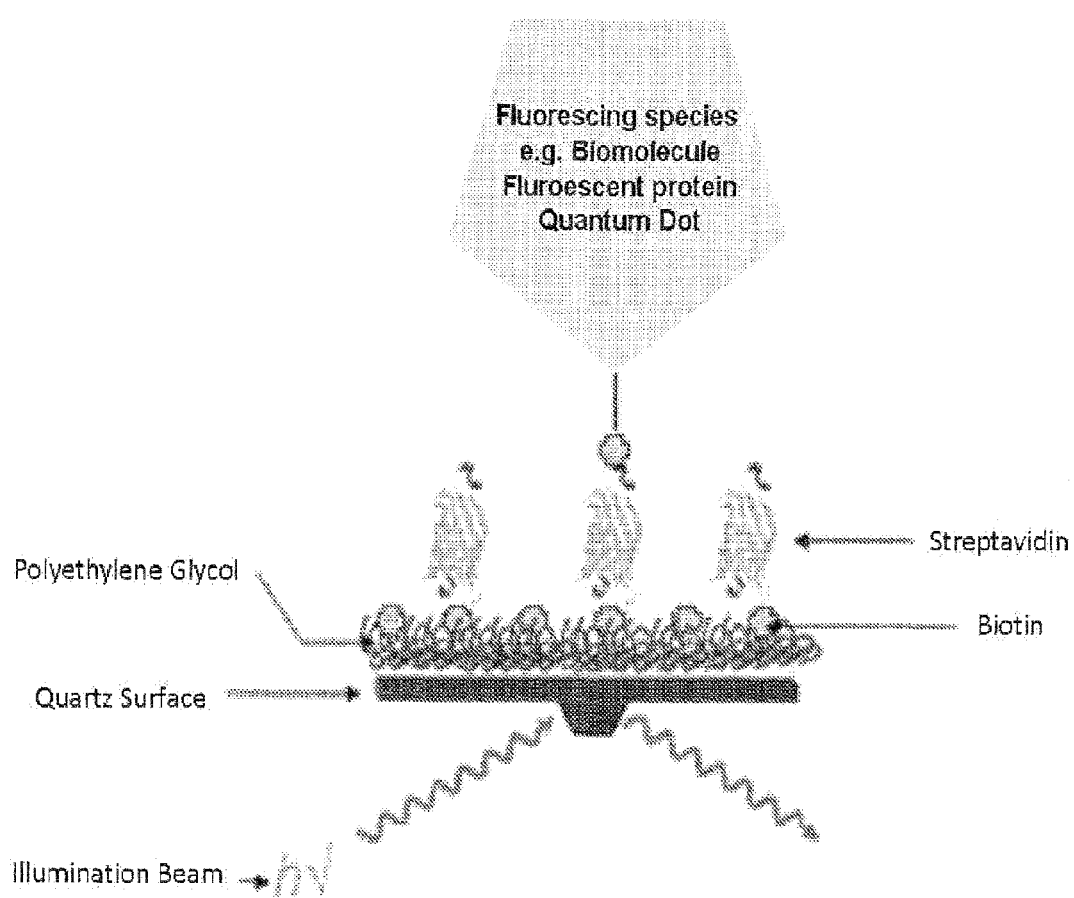
FIG. 2. Schematic of the Total Internal Reflection (TIR) imaging approach. A single-fluorescently labeled species is tethered within the evanescent wave generated by TIR of one or more single-frequency light sources. Fluorophore proximity to an optically-transparent surface is achieved by adhesion or through a specific, chemical strategy such as a biotin-streptavidin bridge as shown. In such a configuration, fluorescent properties can be interrogated and examined at high-spatial and -time resolution, comparable or better than those that can be achieved using confocal imaging methods.
Figure 3:
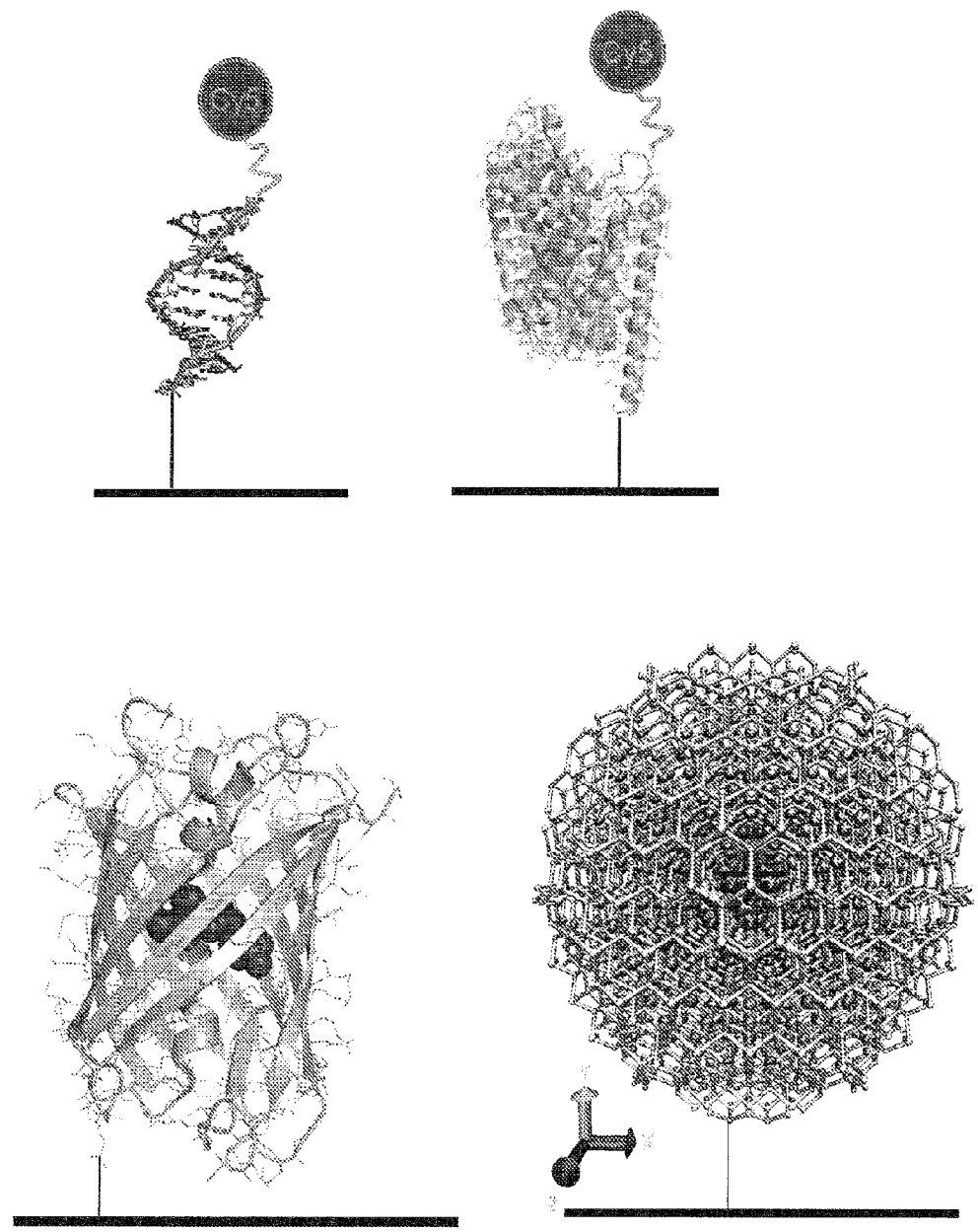
FIG. 3. Single, fluorescent species of relevance to the present invention include organic fluorophores attached to biomolecules of interest (such as DNA or protein molecules as shown in the upper panels), fluorescent proteins (such as mCherry shown in the lower left panel) and quantum dots (lower right panel).
Figure 4:
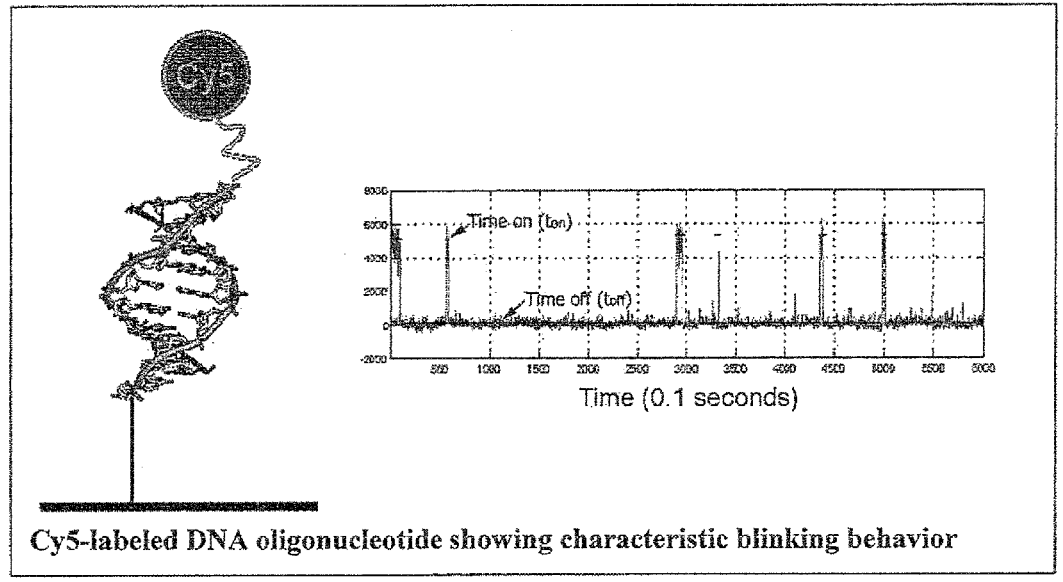
FIG. 4. Graphs showing blinking behavior typical of single fluorescent dye molecules in 3 different experimental contexts: Cy5-labeled DNA oligonucleotides (top panel); a fluorescent protein variant mCherry (middle panel); quantum dot, an example of a nanoparticle (bottom panel). In cellular conditions (which includes molecular oxygen ($O_2$)) or under oxygen scavenging conditions (achieved by degassing or enzymatic means), fluorophores are fluorescent only a fraction of the time (indicated by "Time On", $t_{on}$). The remainder of the time is spent in one or more non-fluorescing states (indicated by "Time Off", $t_{off}$) from which the return to fluorescence can often be slow even in the presence of "photo-resurrecting" light sources. Temporary dark states are referred to in the art as "blinking", events thought to result from intersystem crossing (ISC) to triplet states, while permanent dark states are "photobleached" states thought to result from chemical damage to the fluorescing species.
Figure 4:
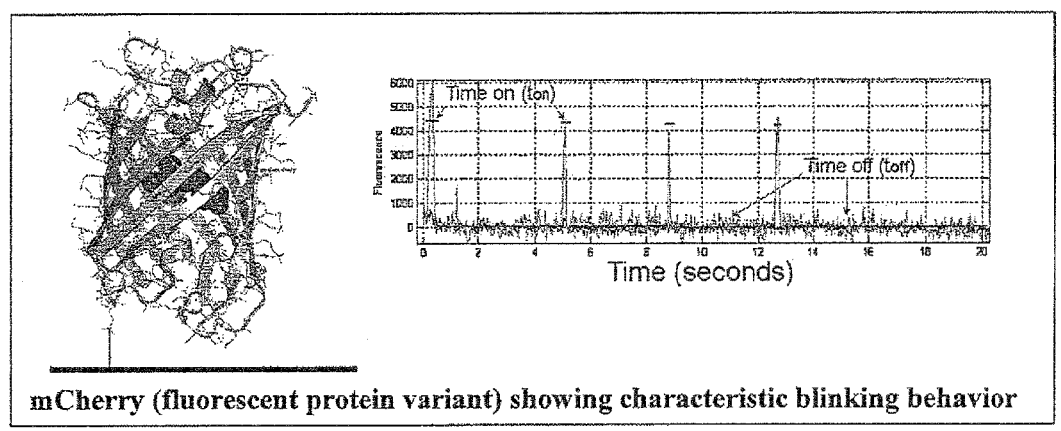
Figure 4:
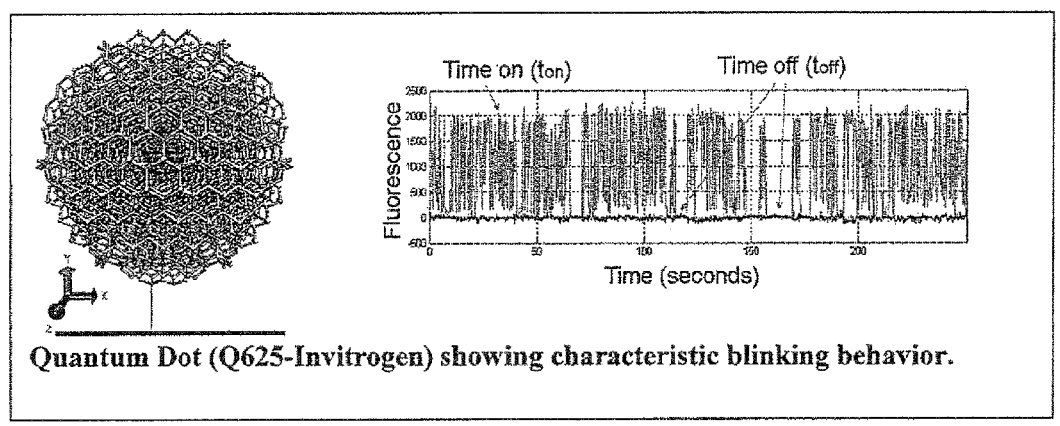
Figure 5:
FIG. 5. Exemplary "protective agents" which have been shown to mitigate unwanted photophysical processes. Shown are COT, Trolox and NBA and derivatives thereof.
Figure 5:
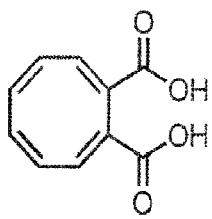
Figure 5:
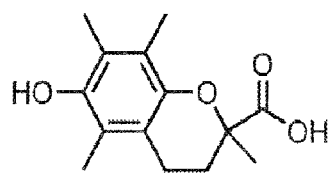
Figure 5:
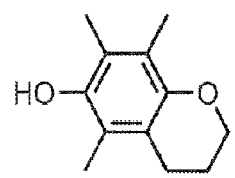
Figure 5:
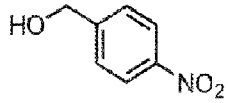
Figure 5:
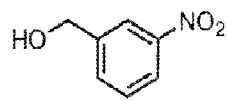
Figure 5:
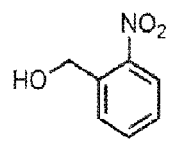
Figure 5:
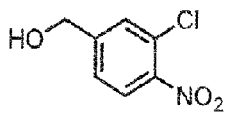
Figure 5:
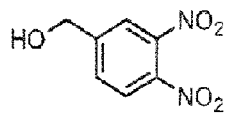
Figure 5:
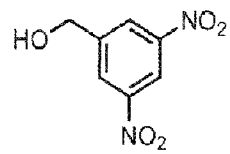
Figure 5:
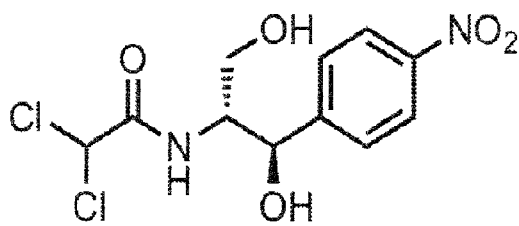

As used herein, a "fluorophore" (or "fluorescing species") refers to any species possessing a fluorescent property when appropriately stimulated. The stimulation that elicits fluorescence is typically illumination; however, other types of stimulation (e.g., collisional) are also considered herein.

In one embodiment, the fluorophore is an organic fluorophore. In different embodiments, the organic fluorophore can include, for example, a charged (i.e., ionic) molecule (e.g., sulfonate or ammonium groups), uncharged (i.e., neutral) molecule, saturated molecule, unsaturated molecule, cyclic molecule, bicyclic molecule, tricyclic molecule, polycyclic molecule, acyclic molecule, aromatic molecule, and/or heterocyclic molecule (i.e., by being ring-substituted by one or more heteroatoms selected from, for example, nitrogen, oxygen and sulfur). In the particular case of unsaturated fluorophores, the fluorophore contains one, two, three, or more carbon-carbon and/or carbon-nitrogen double and/or triple bonds. In a particular embodiment, the fluorophore contains at least two (e.g., two, three, four, five, or more) conjugated double bonds aside from any aromatic group that may be in the fluorophore. In other embodiments, the fluorophore is a fused polycyclic aromatic hydrocarbon (PAH) containing at least two, three, four, five, or six rings (e.g., naphthalene, pyrene, anthracene, chrysene, triphenylene, tetracene, azulene, and phenanthrene) wherein the PAH can be optionally ring-substituted or derivatized by one, two, three or more heteroatoms or heteroatom-containing groups.

In other embodiments, the organic fluorophore is a xanthene derivative (e.g., fluorescein, rhodamine, Oregon green, eosin, and Texas Red), cyanine or its derivatives or subclasses (e.g., streptocyanines, hemicyanines, closed chain cyanines, phycocyanins, allophycocyanins, indocarbocyanines, oxacarbocyanines, thiacarbocyanines, merocyanins, and phthalocyanines), naphthalene derivatives (e.g., dansyl and prodan derivatives), coumarin and its derivatives, oxadiazole and its derivatives (e.g., pyridyloxazoles, nitrobenzoxadiazoles, and benzoxadiazoles), pyrene and its derivatives, oxazine and its derivatives (e.g., Nile Red, Nile Blue, and cresyl violet), acridine derivatives (e.g., proflavin, acridine orange, and acridine yellow), arylmethine derivatives (e.g., auramine, crystal violet, and malachite green), and tetrapyrrole derivatives (e.g., porphyrins and bilirubins). Some particular families of dyes considered herein are the Cy® family of dyes (e.g., Cy2, Cy3, Cy3B, Cy3.5, Cy5, Cy5.5, and Cy7), the Alexa® family of dyes (e.g., Alexa Fluor 350, 405, 430, 488, 500, 514, 532, 546, 555, 568, 594, 610, 633, 647, 660, 680, 700, 750, and 790), the ATTO® family of dyes (e.g., ATTO 390, 425, 465, 488, 495, 520, 532, 550, 565, 590, 594, 601, 615, 619, 629, 635, 645, 663, 680, 700, 729, and 740), and the Dy® family of dyes (e.g., DY 530, 547, 548, 549, 550, 554, 556, 560, 590, 610, 615, 630, 631, 631, 632, 633, 634, 635, 636, 647, 648, 649, 650, 651, 652, 675, 676, 677, 680, 681, 682, 700, 701, 730, 731, 732, 734, 750, 751, 752, 776, 780, 781, 782, and 831). The ATTO dyes, in particular, can have several structural motifs, including, coumarin-based, rhodamine-based, carbopyronin-based, and oxazine-based structural motifs.

In a particular embodiment, the fluorophore is a streptocyanine (open chain cyanine) having the general structure:

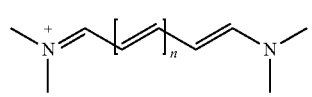

(1)

wherein n in formula (1) above can be, for example, precisely, at least, or no more than 0, 1, 2, 3, 4, 5, 6, 7, 8, or within a range therein. Other structures related to or derived from formula (1) are also considered herein, as amply described in Guieu, V., et al., *Eur. J. Org. Chem.,* 2007, 804-810, which is incorporated herein by reference in its entirety. A particular streptocyanine molecule considered herein has the following structure:

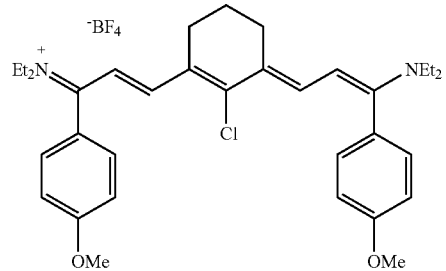

(1a)

In another particular embodiment, the fluorophore is a hemicyanine having the general structure:

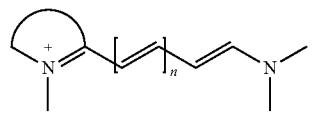

(2)

wherein n in formula (2) is as defined above. Other structures related to or derived from formula (2) are also considered herein, as amply described in Stathatos, E., et al. *Chem. Mater.,* 2001, 13, 3888-3892, and Yao, Q.-H., et al. *J. Mater. Chem.,* 2003, 13, 1048-1053, which are incorporated herein by reference in their entirety. Some particular streptocyanine molecules considered herein have the following structures:

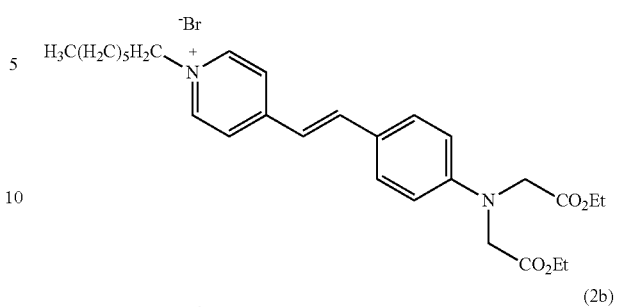

(2a)

(2b)

In another particular embodiment, the fluorophore is a closed cyanine having the general structure:

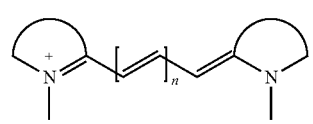

(3)

wherein n in formula (3) is as defined above. Some particular streptocyanine molecules considered herein have the following structures:

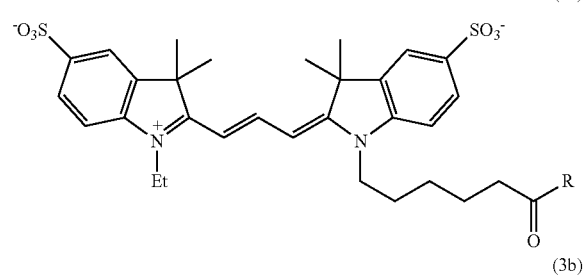

(3a)

(3b)

In another particular embodiment, the fluorophore is a coumarin-based molecule having the general structure:

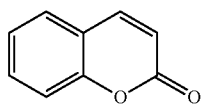
(4)

Other structures related to or derived from formula (4) are also considered herein, as amply described in Schiedel, M.-S., et al. *J. Organomet. Chem.* 2002, 653, 200-208, which is incorporated herein by reference in its entirety. Some particular coumarin-based molecules considered herein have the following structures:

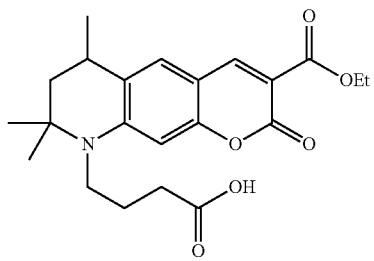
(4a)

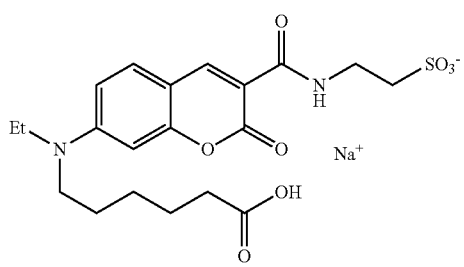
(4b)

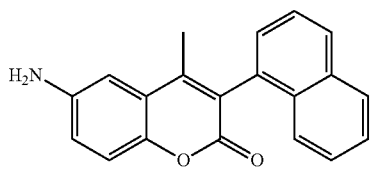
(4c)

In another particular embodiment, the fluorophore is a rhodamine-based molecule having the general structure:

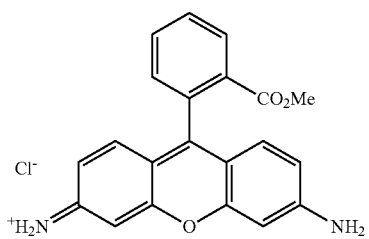
(5)

Other structures related to or derived from formula (5) are also considered herein, as amply described in Beija, M., et al. *Chem. Sec. Rev.* 2009, 38, 2410-2433, which is incorporated herein by reference in its entirety. Some particular rhodamine-based molecules considered herein have the following structures:

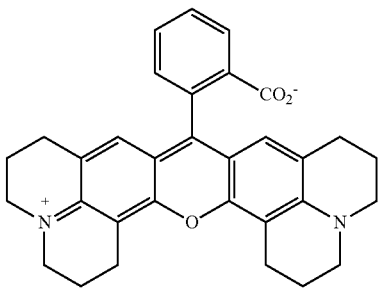
(5a)

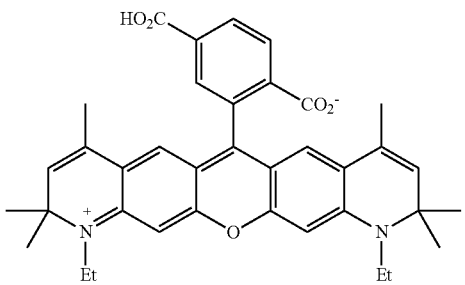
(5b)

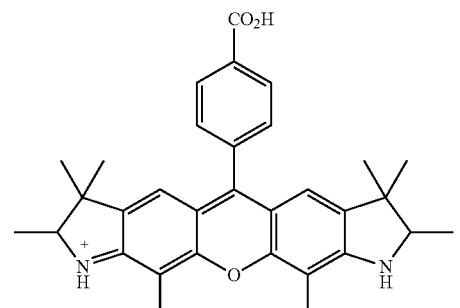
(5c)

In another particular embodiment, the fluorophore is a carbopyronin-based molecule having the general structure:

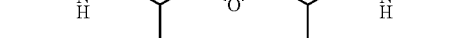
(6)

Other structures related to or derived from formula (6) are also considered herein, as amply described in Arden-Jacob, J., et al. *Spectrochim. Acta* 2001, 57, 2271-2283, which is incorporated herein by reference in its entirety. Some particular carbopyronin-based molecules considered herein have the following structures:

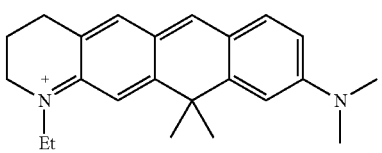
(6a)

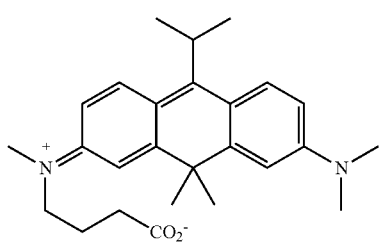

(6b)

In another particular embodiment, the fluorophore is a oxazine-based molecule having the general structure:

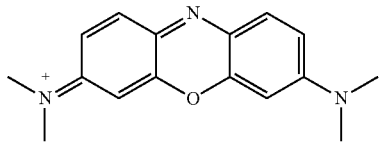

(7)

Other structures related to or derived from formula (7) are also considered herein, as amply described by Van Thien, T. in *Chemistry and Applications of Leuco Dyes* 1997, 67-95, which is incorporated herein by reference in its entirety. A particular oxazine-based molecule considered herein has the following structure:

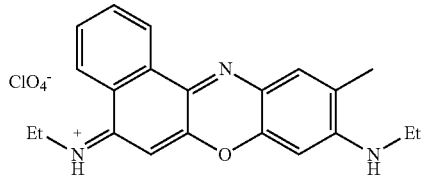

(7a)

In another particular embodiment, the fluorophore consists of at least two (e.g., two, three, four, five, or more) conjugated double bonds aside from any aromatic group that may be in the fluorophore. Such compounds may not necessarily be classified as belonging to a particular group. Some particular compounds of this nature considered herein have the following structures:

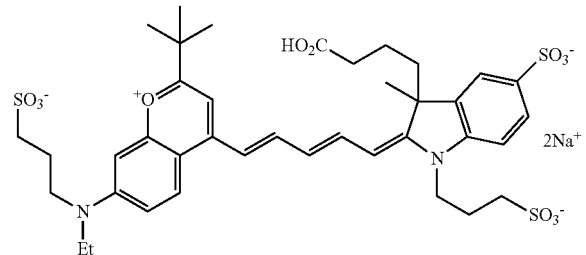

(8a)

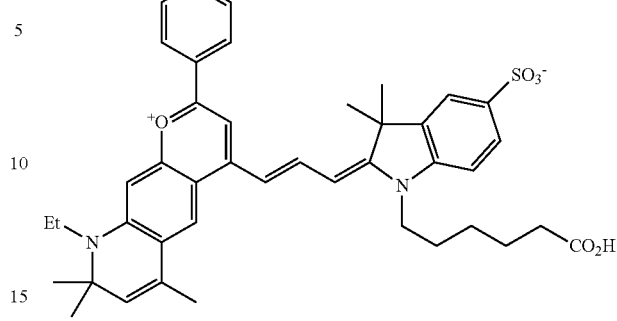

(8b)

(8c)

The fluorophores considered herein can absorb and emit light of any wavelengths. However, in different embodiments, it may be desired to select a fluorophore with particular absorption and emission characteristics. For example, in different embodiments, the fluorophore preferably absorbs at nanometer (nm) wavelengths of 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, or 800 nm, or within a range bounded by any two of the foregoing values. In different embodiments, the fluorophore preferably emits at any of the foregoing wavelengths, or within a range bounded by any two of the foregoing values, wherein it is understood that a fluorophore generally emits at a higher wavelength than the absorbed wavelength. The impinging electromagnetic radiation (i.e., which is absorbed by the fluorophore) can be in a dispersed form, or alternatively, in a focused form, such as a laser. Moreover, the absorbed or emitted radiation can be in the form of, for example, far infrared, infrared, far red, visible, near-ultraviolet, or ultraviolet. When two or more fluorophores are used (e.g., attached to a biomolecule, as in FRET and smFRET methods), one of the fluorophores functions as a donor fluorophore and the other functions as an acceptor fluorophore. In some embodiments, it is preferred for a protective agent to bind to or be in close proximity with either the acceptor fluorophore or the donor fluorophore, but not both.

In particular embodiments, a "red-shifted fluorophore" is preferred. The red-shifted fluorophore is characterized by exhibiting an emission wavelength greater than 594 nm. Such fluorophores are particularly useful in FRET and small molecule FRET (i.e., smFRET) methods.

In another embodiment, the fluorophore has an inorganic composition. For example, the fluorophore can include a fluorescent transition metal or rare earth (e.g., lanthanide) metal species or particle (e.g., nanoparticle or microparticle). The transition metal or rare earth metal species can be, for example, a metal-ligand complex. The ligand can be any suitable ligand, such as, for example, acetylacetonate, a Schiff base (e.g., salen), amine, phosphine, thiol, phenanthroline, bipyridine, or phenolate-based ligand. By "transition metal" is meant any of the metals in Groups IB to VIIIB of the Periodic Table. By "rare earth metal" is meant any of the lanthanides and actinides with atomic numbers of, respectively, 57-71 and 90-103. Some particular rare earth metals considered herein include lanthanum, cerium, praseodymium, neodymium, promethium, samarium, europium, gadolinium, terbium, dysprosium, holmium, erbium, thulium, ytterbium, lutetium, and hafnium, and combinations thereof.

In one embodiment, a fluorescent nanoparticle contains a non-fluorescent matrix (e.g., a polymer, ceramic, or metal) into which is included an organic or inorganic fluorescent species (i.e., within or on the surface of the nanoparticle). In particular embodiments, the particle includes an organic polymer (e.g., polystyrene) or inorganic polymer (e.g., silica or siloxane-based). In another embodiment, the particle includes a metal, e.g., nanoparticles based on copper, silver, gold, palladium, or platinum, or a combination thereof. In another embodiment, the fluorescent particle has a semiconductor (i.e., quantum dot) composition. The quantum dot particle typically includes a sulfide, selenide, telluride, nitride, phosphide, arsenide, and/or antimonide of a Group IB element (e.g., Cu or Ag), Group II element (e.g., Zn or Cd), or Group III element (e.g., B, Al, Ga, or In), or combination of these elements. Furthermore, the quantum dot can be essentially homogeneous in structure, or alternatively, layered (e.g., a core-shell quantum dot). The core and shell of such a quantum dot can, independently, be composed of any of the semiconductor compositions described above (e.g., "core: shell" compositions of the type ZnS:CdSe, ZnSe:CdSe, ZnS: CdS, ZnSe:CdS, CdS:ZnSe, CdSe:ZnSe, CdS:ZnS, or CdSe: ZnS). In some embodiments, the quantum dot further includes a dopant fluorescent species, such as any of the rare earth metals or organic fluorescent species described above, either by being incorporated into the core or shell of the quantum dot or by being adsorbed or linked to the surface or passivation shell of the quantum dot.

In different embodiments, the particle (particularly, a quantum dot) possesses a size (i.e., diameter) of, for example, 1, 2, 5, 10, 15, 20, 30, 40, 50, 60, 70, 80, 90, 100, 110, or 120 nm, or a size within a range bounded by any two of the foregoing values. A metal particle that is not a quantum dot may be any of the foregoing sizes, as well as significantly larger sizes, e.g., about, at least, or no more than 150, 200, 250, 300, 350, 400, or 500 nm or a size within a range bounded by any two of the foregoing values. A polymer particle can be any of the foregoing sizes, as well as significantly larger sizes, e.g., about, at least, or no more than 600, 700, 800, 900, 1000, 2000, 3000, 4000, or 5000 nm, or a size within a range bounded by any two of the foregoing values.

Any of the fluorophores considered herein (and particularly, the organic fluorophores) can include functional groups that allow them to be linked to another molecule or conjugated to a biomolecule. For example, the fluorophore can include one, two, or more amino-reactive, thiol-reactive, aldehyde-reactive, or ketone-reactive groups. Some examples of amino-reactive groups include activated ester groups (e.g., N-succinimidyl ester (e.g., N-hydroxysuccinimidyl, i.e., NHS), carbodiimide ester groups (e.g., EDC), tetrafluorophenyl esters, dichlorophenol esters, and sulfo-derivatives thereof), and combinations thereof), isothiocyanate, sulfonylchloride, dichlorotriazines, aryl halides, and acyl azides. Some examples of thiol reactive groups include maleimido groups, haloacetamide (e.g., iodoacetamide) groups, disulfide groups, thiosulfate, and acryloyl groups. Some examples of aldehyde-reactive and ketone-reactive groups include hydrazide, semicarbazide, carbohydrazide, and hydroxylamine groups. The functional group can also be a reactive probe, i.e., a chemical moiety that selectively targets (i.e., binds to and/or reacts with) another molecule. In a preferred example, the reaction is specific for the two reacting species such that reaction of the probe with another functional group on the molecule of interest is not possible (e.g., reactions reviewed in Prescher, J. A., et al., *Nat. Chem. Biol.* 2005, 1, 13-21, which is incorporated herein by reference in its entirety). For example, a biotin molecule may be included in the fluorophore to specifically bind the fluorophore to a streptavidin conjugate; or an antibody or fragment thereof may be included in the fluorophore to specifically bind the fluorophore to a molecule bearing an epitope reactive with the antibody; or a peptide, oligopeptide, or lectin may be included in the fluorophore to specifically bind or react the fluorophore with another biomolecule; or a nucleic acid, nucleoside, nucleotide, oligonucleotide, or DNA or RNA strand or vector may be included in the fluorophore to specifically bind the fluorophore to a complimentary strand.

As used herein, a "protective agent" (or "quencher" or "triplet state quencher" or "fluorescence modifier", in particular embodiments) is a molecule or a moiety (i.e., group) that has the ability to alter the photophysical properties of a fluorophore, particularly by altering the light state-dark state (i.e., singlet-triplet) occupancy distribution or relaxation pathway of excited and relaxing electrons. The ability of a molecule to function as a protective agent is often evidenced by its ability to alter the blinking and/or photobleaching characteristics of a fluorophore.

In a particular embodiment, the protective agent is a chromanol-derived molecule within the following generic structural formula:

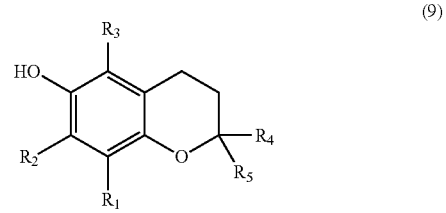

(9)

In formula (9) above, $R_1$, $R_2$, $R_3$, $R_4$ and $R_5$ can independently be selected from a hydrogen atom or hydrocarbon group. The hydrocarbon group can be saturated or unsaturated, and/or straight-chained or branched, and/or cyclic or acyclic, and can include, for example, one, two, three, four, five, six, seven, eight, nine, ten, eleven, twelve, or more carbon atoms (e.g., methyl, ethyl, n-propyl, isopropyl, n-butyl, isobutyl, t-butyl, pentyl, hexyl, heptyl, octyl, nonyl, decyl, and dodecyl groups). An unsaturated hydrocarbon group can contain at least one, two, three, or more carbon-carbon or carbon-nitrogen double and/or triplet bonds. In one embodiment, the hydrocarbon group is composed solely of carbon and hydrogen. In another embodiment, the hydrocarbon group includes one, two, three, or more heteroatoms, such as oxygen, nitrogen, sulfur, and/or halogen (e.g., fluoro, chloro, bromo, iodo) atoms. Since the protective agent molecules described herein are often directly or indirectly covalently linked to a fluorophore and/or biomolecule, a surface (i.e., of a bulk solid), or other molecule of interest, any one or more of the groups $R_1$, $R_2$, $R_3$, $R_4$ and $R_5$ can also represent a bond to another molecule or surface, or alternatively, a linking group with a bond to another molecule or a surface. Often, the group $R_4$ can be taken as a bond to an atom of a molecule, macromolecule, or surface.

In particular embodiments of formula (9), $R_1$, $R_2$, and $R_3$ are selected from methyl and hydrogen atoms (i.e., all methyl groups, or two methyl groups and one hydrogen atom, or one methyl group and two hydrogen atoms, or all hydrogen atoms). In another particular embodiment, $R_4$ is a methyl or carboxylic acid group, or a methylene, ethylene, carbonyl, ester, or amido linking group. In other embodiments, $R_4$ and $R_5$ are independently selected from methyl, ethyl, vinyl, allyl, n-propyl, n-butyl, isobutyl, t-butyl, and/or hydrogen (H) groups. In particular embodiments, $R_4$ and $R_5$ are both methyl groups, both hydrogen atoms, or one is methyl and the other hydrogen. In other particular embodiments, $R_5$ is a long chain hydrocarbon group (e.g., of at least 4, 5, 6, 7, 8, 9, 10, 11, 12, 13, 14, 15, or 16 carbon atoms).

In more specific embodiments, $R_5$ is an unsaturated group that results in formula (9) being a tocopherol, or tocotrienol, or derivative thereof; for example, wherein $R_5$ has the structure:

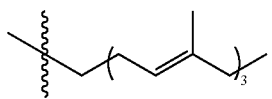

(10)

In a particular embodiment, the protective agent is Trolox, which has the following formula:

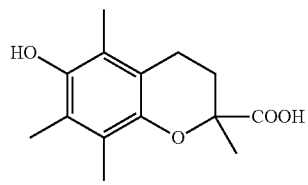

(11)

Formula (11) is also meant to include any derivative of Trolox that retains protective agent abilities. The Trolox derivative can be, for example, a result of replacing the carboxy OH group by a hydrocarbon group (e.g., any of the hydrocarbon groups described above), an ether group (i.e., —OR group, where R is a hydrocarbon group or ester-activating group), an amino group (i.e., —$NR_6R_7$ group, where $R_6$ and $R_7$ are selected from hydrogen atoms and/or hydrocarbon groups), β-keto group, sulfonamide group, phosphate group, or chloro group. The Trolox derivative can also be, for example, a result of replacing the phenolic OH group or a hydrogen atom with any of the foregoing groups. Formula (11) is also meant to include a Trolox or Trolox derivative group bound to an atom of another molecule (wherein the molecule may be, for example, a fluorophore, a linker, biomolecule, macromolecule, or surface). The Trolox group results by replacement of one or more hydrogen atoms of Trolox or derivative thereof with a bond (or with a linker having a bond) to another molecule or surface. The hydrogen atom being replaced with a bond can be, for example, from a C—H group, hydroxyl group, amino group, or other group. Alternatively, the Trolox group results by replacement of one or more hydroxyl groups, methyl groups, or the carboxy group with a bond (or with a linker having a bond) to another molecule or surface.

In another particular embodiment, the protective agent is a nitro-substituted aromatic molecule or group in which the aromatic molecule or group can be cyclic (i.e., contain a single ring) or polycyclic (i.e., two, three, four, or more rings either linked or fused with each other). Typically, the molecule contains one or two nitro groups per molecule or ring. Some examples of nitro-substituted aromatic molecules include nitrobenzene, the nitrotoluenes, picric acid, the nitronaphthalenes, nitrobiphenyls, and nitro derivatives of any of the polycyclic aromatic hydrocarbons described above, and derivatives thereof (e.g., inclusion of one or more hydroxyl, hydroxyalkyl, ether, or carboxamido groups). Some examples of nitro-substituted aromatic groups include those resulting from removal of a hydrogen atom from any of the foregoing exemplary molecules and replacing this with a bond to an atom of another molecule, a surface, or a macromolecule. For example, removal of a methyl hydrogen atom from a p-nitrotoluene molecule results in a p-nitrobenzyl group. In particular embodiments, the nitro-substituted aromatic molecule is o-, m-, or p-nitrobenzyl alcohol (NBA), 2,6-dinitrobenzyl alcohol, 3,4-dinitrobenzyl alcohol, a halo-substituted nitrobenzyl alcohol, or chloroamphenicol. In other embodiments, the nitro-substituted aromatic molecule is o-, m-, or p-nitrobenzyl amine, or derivatives thereof.

In a particular embodiment, the protective agent is a nitro-substituted aromatic molecule or group within the following generic structural formula:

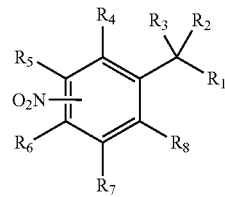

(12)

In formula (12) above, $R_1$, $R_2$, $R_3$, $R_4$, $R_5$, $R_6$, $R_7$, and $R_8$ can independently be selected from a hydrogen atom or hydrocarbon group. The hydrocarbon group can be saturated or unsaturated, and/or straight-chained or branched, and/or cyclic or acyclic, and can include, for example, one, two, three, four, five, six, seven, eight, nine, ten, eleven, twelve, or more carbon atoms (e.g., methyl, ethyl, n-propyl, isopropyl, n-butyl, isobutyl, t-butyl, pentyl, hexyl, heptyl, octyl, nonyl, decyl, and dodecyl groups). An unsaturated hydrocarbon group can contain at least one, two, three, or more carbon-carbon or carbon-nitrogen double and/or triplet bonds. In one embodiment, the hydrocarbon group is composed solely of carbon and hydrogen. In another embodiment, the hydrocarbon group includes one, two, three, or more heteroatoms, such as oxygen, nitrogen, sulfur, and/or halogen (e.g., fluoro, chloro, bromo, iodo) atoms. Since the protective agent molecules described herein are often directly or indirectly covalently linked to a fluorophore and/or biomolecule, a surface (i.e., of a bulk solid), or other molecule of interest, any one or more of the groups $R_1$, $R_2$, $R_3$, $R_4$, $R_5$, $R_6$, $R_7$, and $R_5$ can also represent a bond to another molecule or surface, or alternatively, a linking group with a bond to another molecule or a surface. Often, the group $R_1$ can be taken as a bond to an atom of a molecule, macromolecule, or surface.

In particular embodiments of formula (12), $R_1$, $R_2$, and $R_3$ are selected from nitrogen, oxygen, carbon, and hydrogen atoms with the proviso that at least one of them is either nitrogen or oxygen.

In more specific embodiments, $R_1$ is an unsaturated group that results in formula (12) being a nitrobenzyl alcohol, or derivative thereof; for example, wherein $R_1$ has the structure:

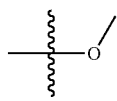
(13)

In more specific embodiments, $R_1$ is an unsaturated group that results in formula (12) being a nitrobenzyl amine, or derivative thereof; for example, wherein $R_1$ has the structure:

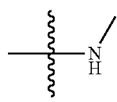
(14)

In more specific embodiments, $R_1$ is an unsaturated group that results in formula (12) being a nitrobenzyl ethane-1,2-diamine, or derivative thereof; for example, wherein $R_1$ has the structure:

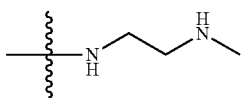
(15)

In more specific embodiments, $R_1$ is an unsaturated group that results in formula (12) being a 2-(nitrobenzylamino) ethanol, or derivative thereof; for example, wherein $R_1$ has the structure:

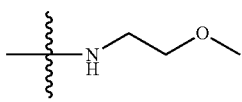
(16)

In a particular embodiment, the protective agent of formula (12) is $N^1$-(4-nitrobenzyl)ethane-1,2-diamine, which has the following formula:

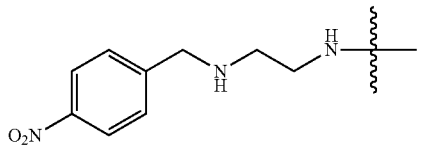
(17)

Formula (17) is also meant to include any derivative of $N^1$-(4-nitrobenzyl)ethane-1,2-diamine that retains protective agent abilities. Such a derivative can be, for example, a result of replacing either one or both of the amines with another heteroatom (i.e., oxygen, sulfur, or phosphorous), a sulfonamide group, or phosphate group. The $N^1$-(4-nitrobenzyl) ethane-1,2-diamine derivative can also be, for example, a result of replacing a hydrogen atom with a nitrogen atom or any of the foregoing groups. Formula (17) is also meant to include M-(4-nitrobenzyl)ethane-1,2-diamine or $N^1$-(4-nitrobenzyl)ethane-1,2-diamine derivative bound to an atom of another molecule (wherein the molecule may be, for example, a fluorophore, a linker, biomolecule, macromolecule, or surface). The $N^1$-(4-nitrobenzyl)ethane-1,2-diamine derivative results by replacement of one or more hydrogen atoms of $N^1$-(4-nitrobenzyl)ethane-1,2-diamine or derivative thereof with a bond (or with a linker having a bond) to another molecule or surface. The hydrogen atom being replaced with a bond can be, for example, from a C—H group, hydroxyl group, amino group, or other group.

In a particular embodiment, the protective agent is Chloramphenicol, which has the following structure:

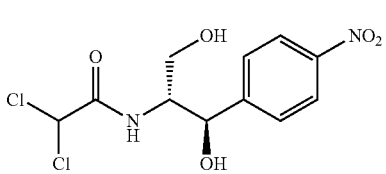
(18)

Formula (18) is also meant to include any derivative of Chloramphenicol that retains protective agent abilities. The Chloramphenicol derivative can be, for example, a result of replacing one or both OH groups by a hydrocarbon group (e.g., any of the hydrocarbon groups described above), an ether group (i.e., —OR group, where R is a hydrocarbon group or ester-activating group), an amino group (i.e., —$NR_6R_7$ group, where $R_6$ and $R_7$ are selected from hydrogen atoms and/or hydrocarbon groups), β-keto group, sulfonamide group, phosphate group, or chloro group. The Chloramphenicol derivative can also be, for example, a result of replacing the amide moiety with any of the foregoing groups. Formula (18) is also meant to include a Chloramphenicol or Chloramphenicol derivative group bound to an atom of another molecule (wherein the molecule may be, for example, a fluorophore, a linker, biomolecule, macromolecule, or surface). The Chloramphenicol group results by replacement of one or more hydrogen atoms of Chloramphenicol or derivative thereof with a bond (or with a linker having a bond) to another molecule or surface. The hydrogen atom being replaced with a bond can be, for example, from a C—H group, hydroxyl group, amino group, or other group. Alternatively, the Chloramphenicol group results by replacement of one or more hydroxyl groups, chloro groups, dichloromethyl group, or the amide group with a bond (or with a linker having a bond) to another molecule or surface.

In another embodiment, the protective agent is a conjugated polyene molecule or group. The conjugated polyene considered herein can be, for example, straight-chained or branched, and either cyclic or acyclic. In different embodiments, the conjugated polyene can contain, for example, two, three, four, five, six, seven, eight, nine, or ten conjugated carbon-carbon double bonds.

The conjugated polyene can, in addition, include one or more carbon-carbon triple bonds. In some embodiments, the protective agent contains two or more carbon-carbon triple bonds conjugated with each other. In such a case, the protective can be considered a polyyne.

In a particular embodiment, the polyene is a cyclic polyene, such as an annulene. The annulenes particularly considered herein are those containing greater than six carbon atoms and/or more than three conjugated carbon-carbon double bonds. The annulene can be aromatic or non-aromatic. Some examples of annulenes particularly considered herein include cyclooctatetraene (i.e., [8]annulene or COT), [10]annulene, [12]annulene, [14]annulene, [16]annulene, and [18]annulene. The annulene may or may not also include one or more carbon-carbon triple bonds. The protective agent may also be a cyclic system containing two, three, four, or more carbon-carbon triple bonds, which is herein referred to as an annulyne. The annulene or annulyne can also be functionalized with any number of hydrocarbon groups, heteroatom-functionalized forms thereof, and heteroatom groups. In particular embodiments, the annulene or annulyne is derivatized with one, two, three, or more carboxy groups (e.g., 1,2-dicarboxycyclooctatetraene).

Typically, the conjugated polyene, annulene, or annulyne considered herein as a protective agent is attached to an atom of another chemical entity (e.g., fluorophore, biomolecule, or surface) either directly via an atom of the polyene, annulene, or annulyne, or through a linker. Accordingly, any of the polyenes, annulenes, or annulynes described above also includes groups derived therefrom.

In another embodiment, the protective agent is a bicyclic, tricyclic, or higher cyclic ring system containing at least two, three, or four ring nitrogen atoms. Some examples of such bicyclic molecules include 1,4-diazacyclohexane, 1,4,7-triazacyclononane, and 1,4,7,10-tetraazacyclododecane. Some examples of such tricyclic molecules include 1,4-diazabicyclo[2.2.2]octane (DABCO), 1,4-diazabicyclo[2.2.1]heptane, 1,5-diazabicyclo[3.2.2]nonane, 1,5-diazabicyclo[3.3.2]decane, 1,5-diazabicyclo[3.3.3]undecane, 1,6-diazabicyclo[4.3.0]nonane, 1,6-diazabicyclo[4.4.0]decane, 1,6-diazabicyclo[4.3.3]dodecane, 1,6-diazabicyclo[4.4.3]tridecane, and 1,6-diazabicyclo[4.4.4]tetradecane. The bicyclic, tricyclic, or higher cyclic ring system may or may not be derivatized with one or more other heteroatoms (e.g., oxygen, sulfur, phosphorus, and halide atoms) and/or heteroatom groups (e.g., carbonyl, ester, carboxyl, amino, amido, and the like). The bicyclic, tricyclic, or higher cyclic ring system may or may not also contain alkenyl or alkynyl groups.

In yet another embodiment, the protective agent is a mercaptan (i.e., hydrocarbon group containing a —SH group). The mercaptan (i.e., thiol) can be a group on any of the hydrocarbon groups described above. For example, the thiol can be thiophenol, 1,4-benzenedithiol, 1,3,5-benzentrithiol, a thionaphthol, or a thioanthracenol (e.g., 9-thioanthracenol). In a particular embodiment, the thiol is a mercapto-substituted straight-chained alcohol, such as β-mercaptoethanol, 3-mercaptopropanol, 4-mercaptobutanol, 5-mercaptopentanol, 6-mercaptohexanol, 7-mercaptoheptanol, and 8-mercaptooctanol. In another particular embodiment, the thiol is a mercapto-substituted straight-chained amine, such as β-mercaptoethylamine, 3-mercaptopropylamine, 4-mercaptobutylamine, 5-mercaptopentylamine, 6-mercaptohexylamine, 7-mercaptoheptylamine, and 8-mercaptooctylamine. In the mercaptan compounds, the thiol group, hydroxyl group, and/or amino group can be substituted with one or more hydrocarbon groups, thereby resulting, respectively, in a thioether, ether, and secondary or tertiary amino group.

In still another embodiment, the protective agent is a phenolic derivative. Some examples of phenolic derivatives include the cresols, butylated phenols (e.g., butylated hydroxytoluene, i.e., BHT), naphthols, anthracenols (e.g., 9-anthracenol), and the like. In a particular embodiment, the phenolic derivative is a polyphenol molecule. Some examples of polyphenol molecules include dihydroquinone, catechol, resorcinol, 1,3,5-trihydroxybenzene, gallic acid and esters thereof (e.g., n-propyl gallate and gallic acid esters of glucose or other sugar), pyrogallol, the flavonoids, flavonols, flavones, catechins, flavanones, anthocyanidins, and isoflavonoids. The phenolic derivative can also be an etherified phenol, wherein the etherifying group can be, for example, a hydrocarbon group, particularly an alkyl group, such as a methyl, ethyl, or isopropyl group.

Figure 20:
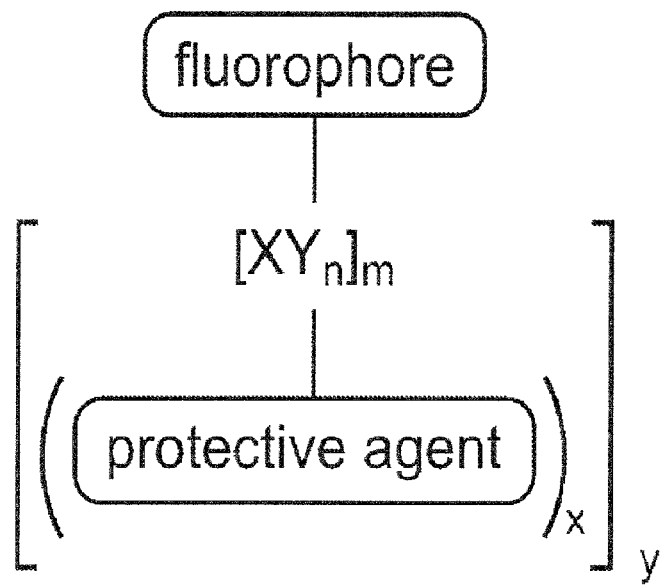
FIG. 20. Drawing encompassing various embodiments of the invention in which a protective agent is connected to a fluorophore via a 'linker', $[XY_n]_m$.
Figure 21:
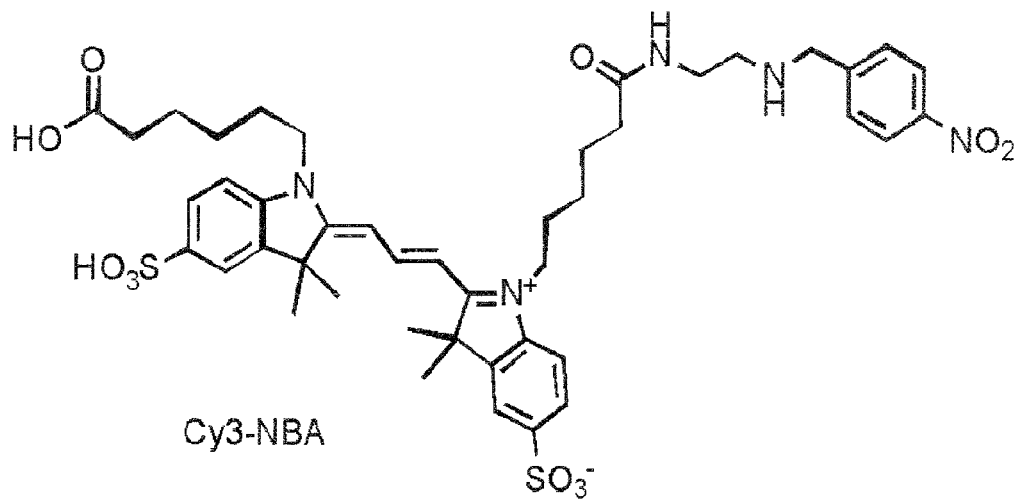
FIG. 21. Drawings showing some exemplary Cy3-NBA and Cy3-Trolox compositions of the invention.
Figure 21:
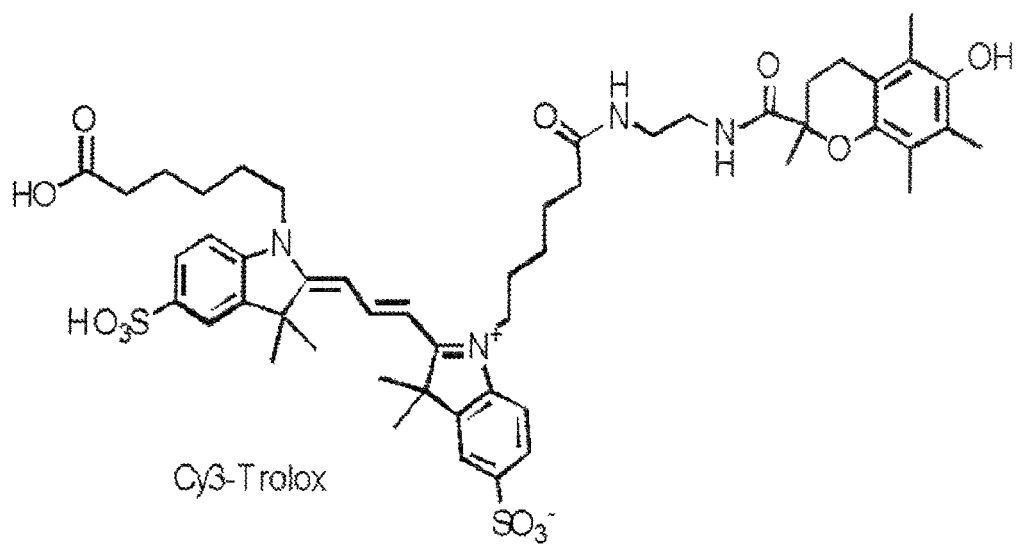
Figure 22:
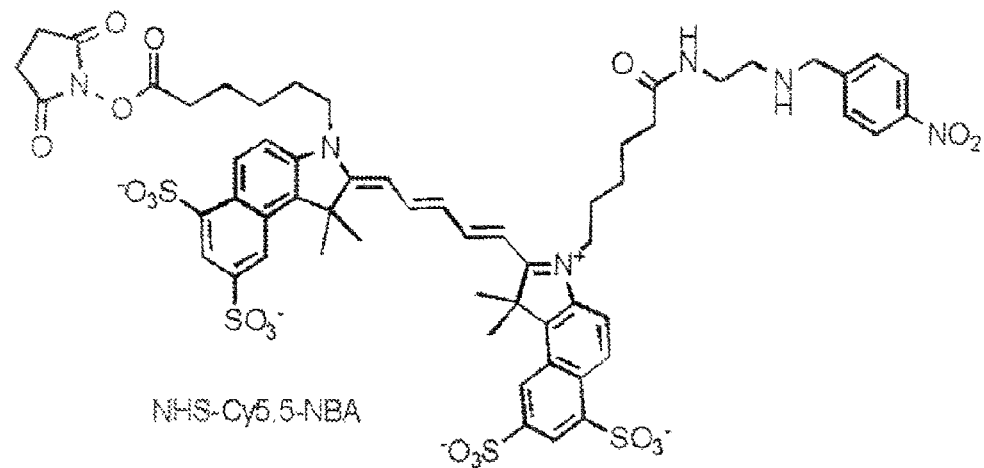
FIG. 22. Drawings showing some exemplary NHS-Cy5.5-NBA and NHS-Cy5.5-Trolox compositions of the invention.
Figure 22:
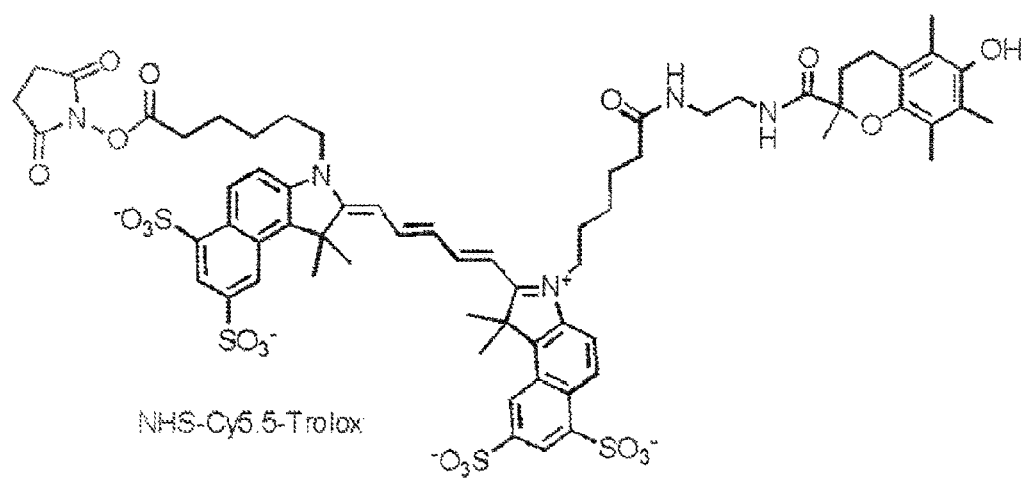
Figure 23A:
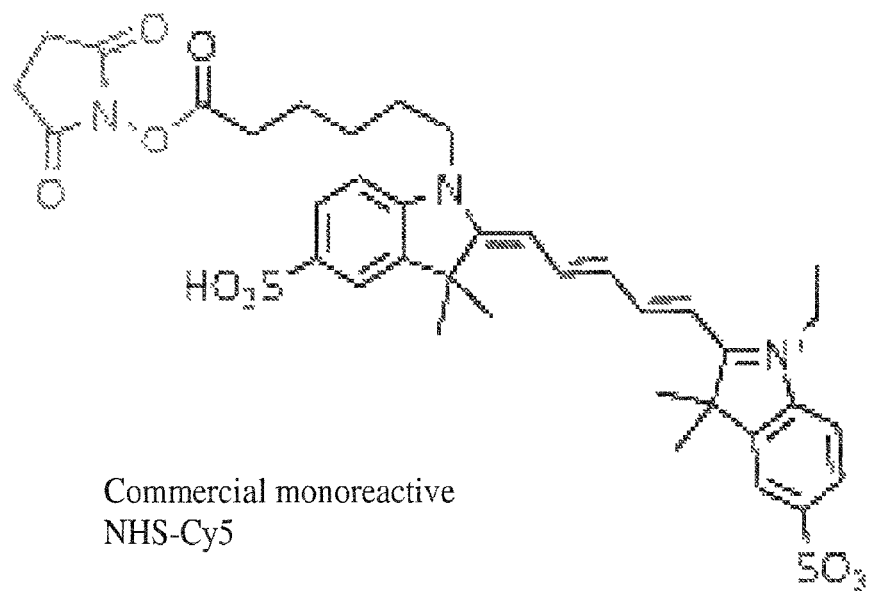
FIGS. 23A-23B. Drawings showing a commercial mono-reactive NHS-Cy5 composition, bis-reactive NHS-Cy5 composition, mono-reactive Mal-Cy5 composition, and bis-reactive Mal-Cy5 composition.
Figure 23A:
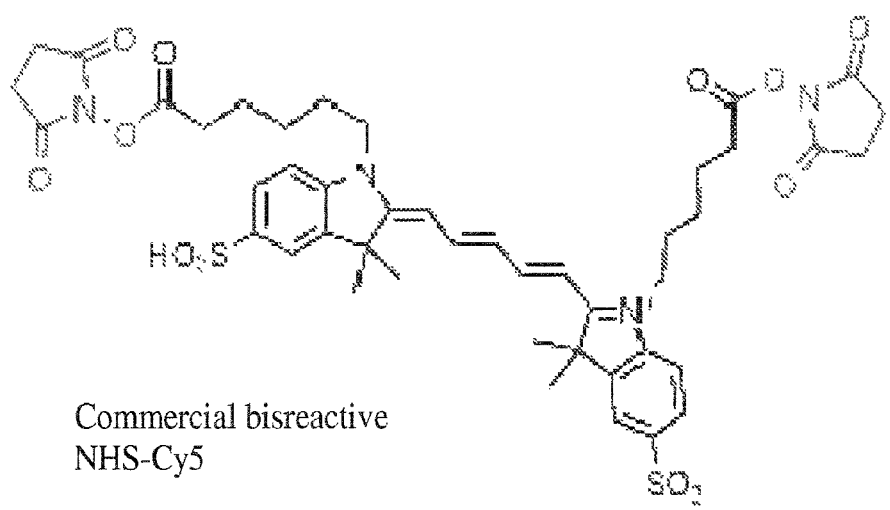
Figure 23B:
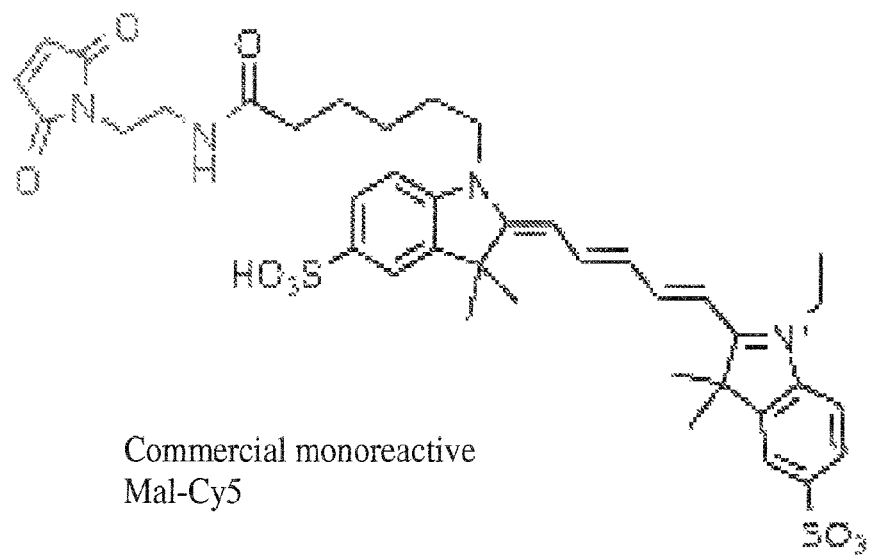
Figure 23B:
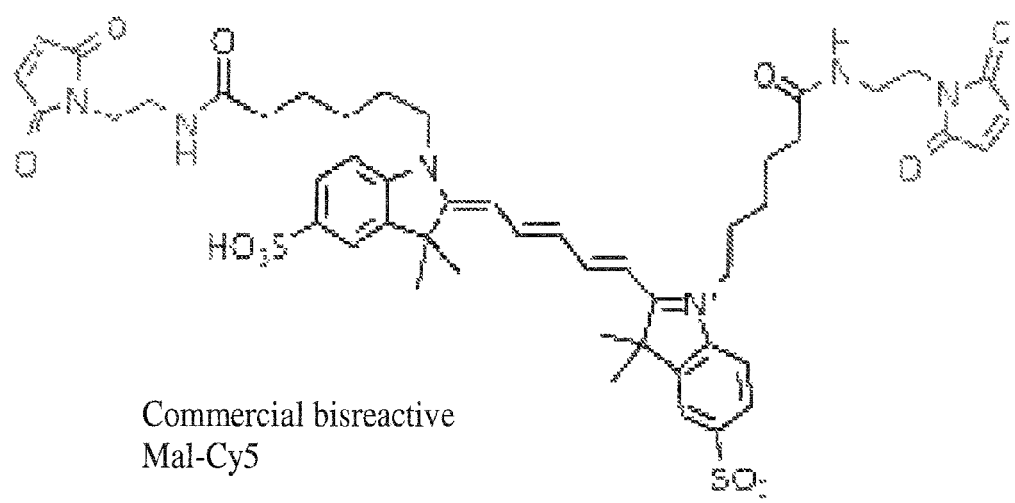
Figure 24A:
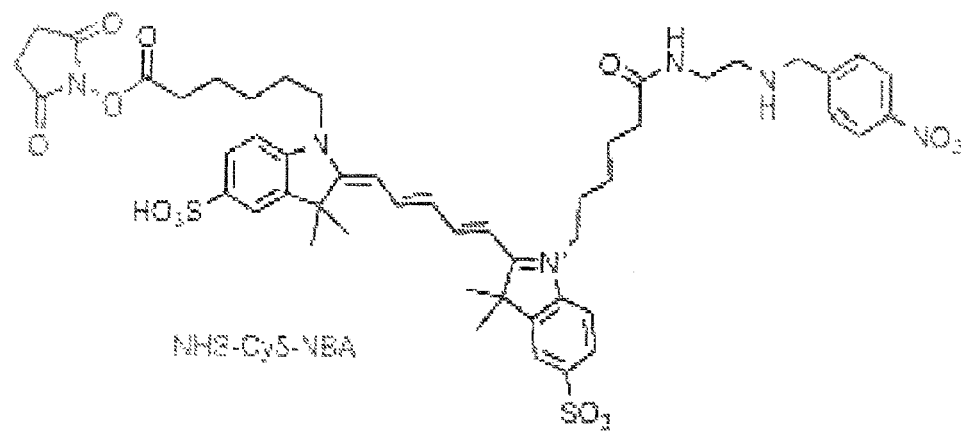
FIGS. 24A-24B. Drawings showing some exemplary NHS-Cy-NBA, NHS-Cy5-Trolox, Mal-Cy5-NBA, and Mal-Cy5-Trolox compositions of the invention.
Figure 24A:
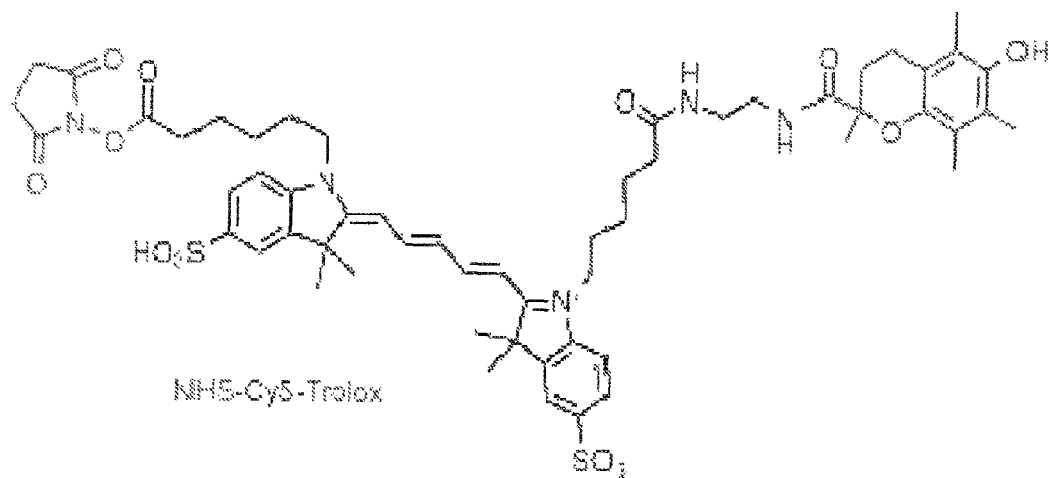
Figure 24B:
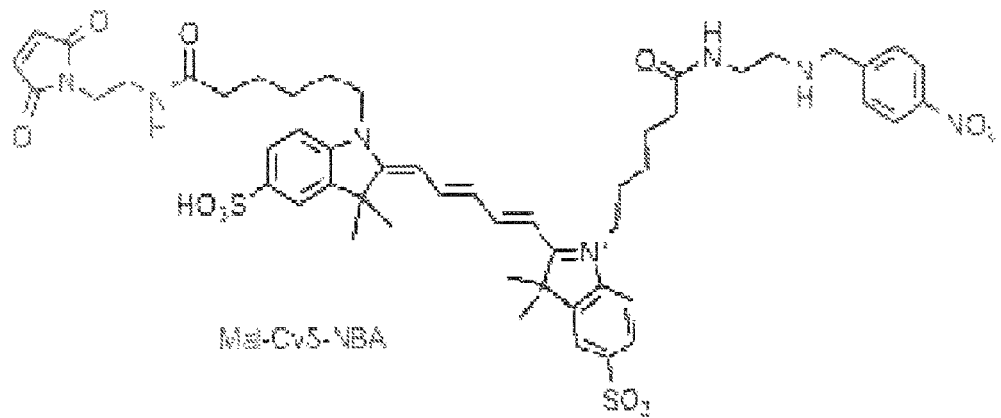
Figure 24B:
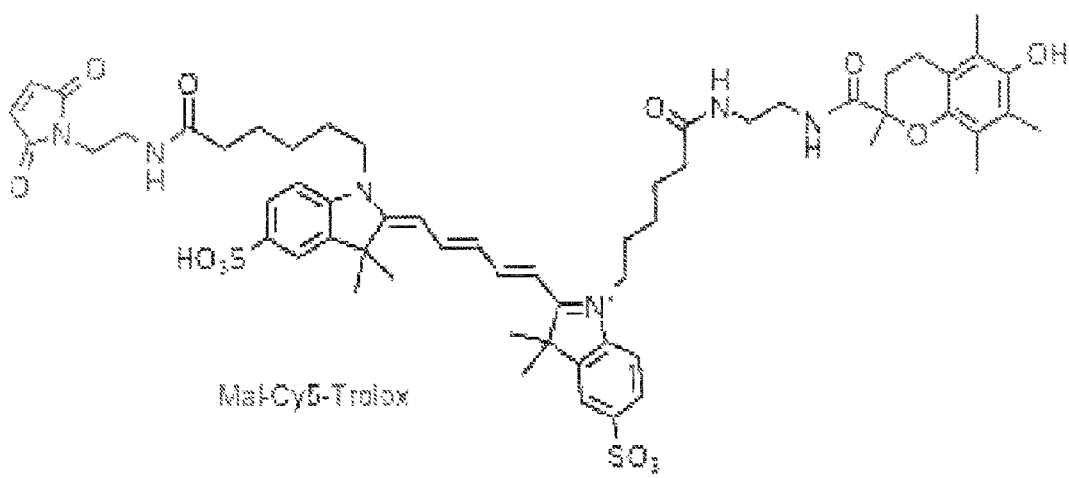
Figure 25A:
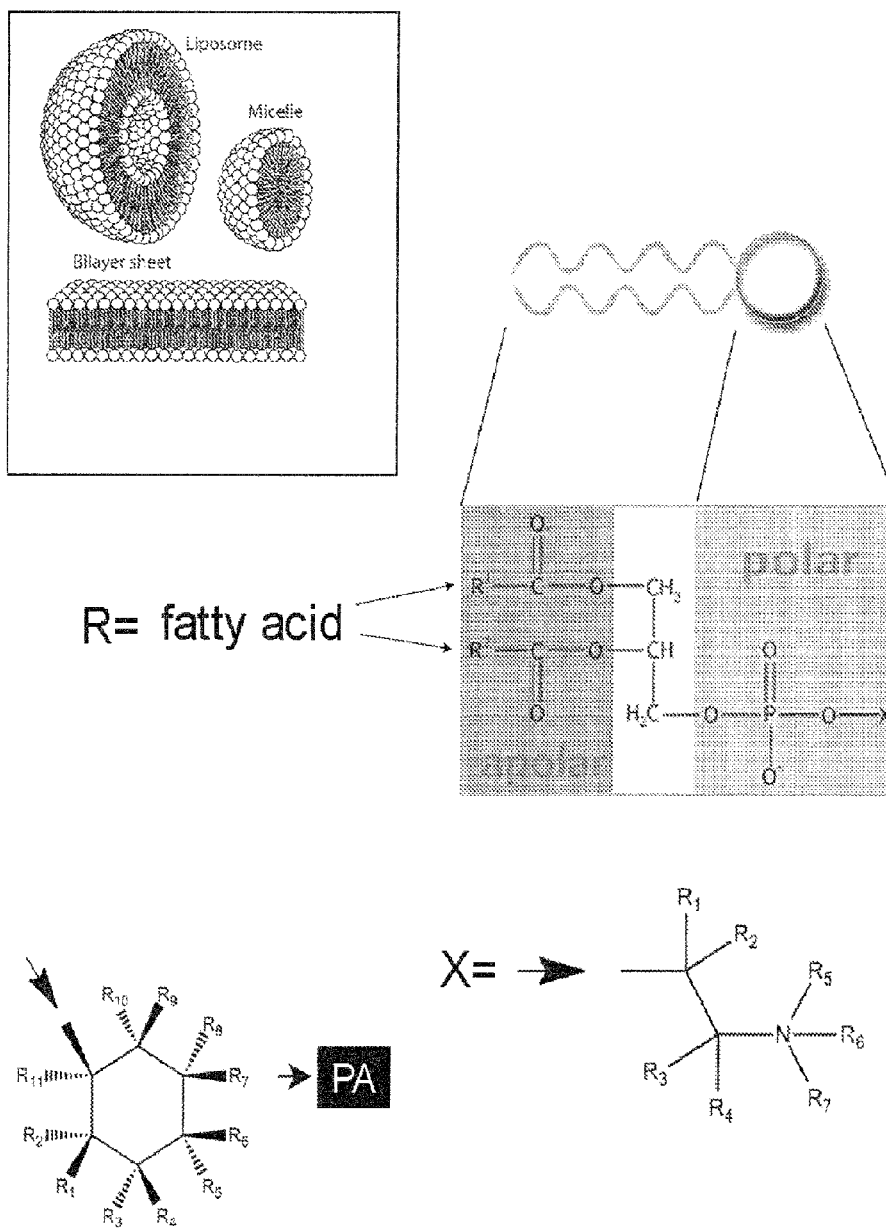
FIGS. 25A-25B. Drawings showing the attachment of one or more protective agents to membrane structures through reactive elements either naturally occurring or introduced into phospholipid head groups or detergents or sterol compounds such as cholesterol that intercalate/impregnate phospholipid bilayers and detergent micelles.
Figure 25B:
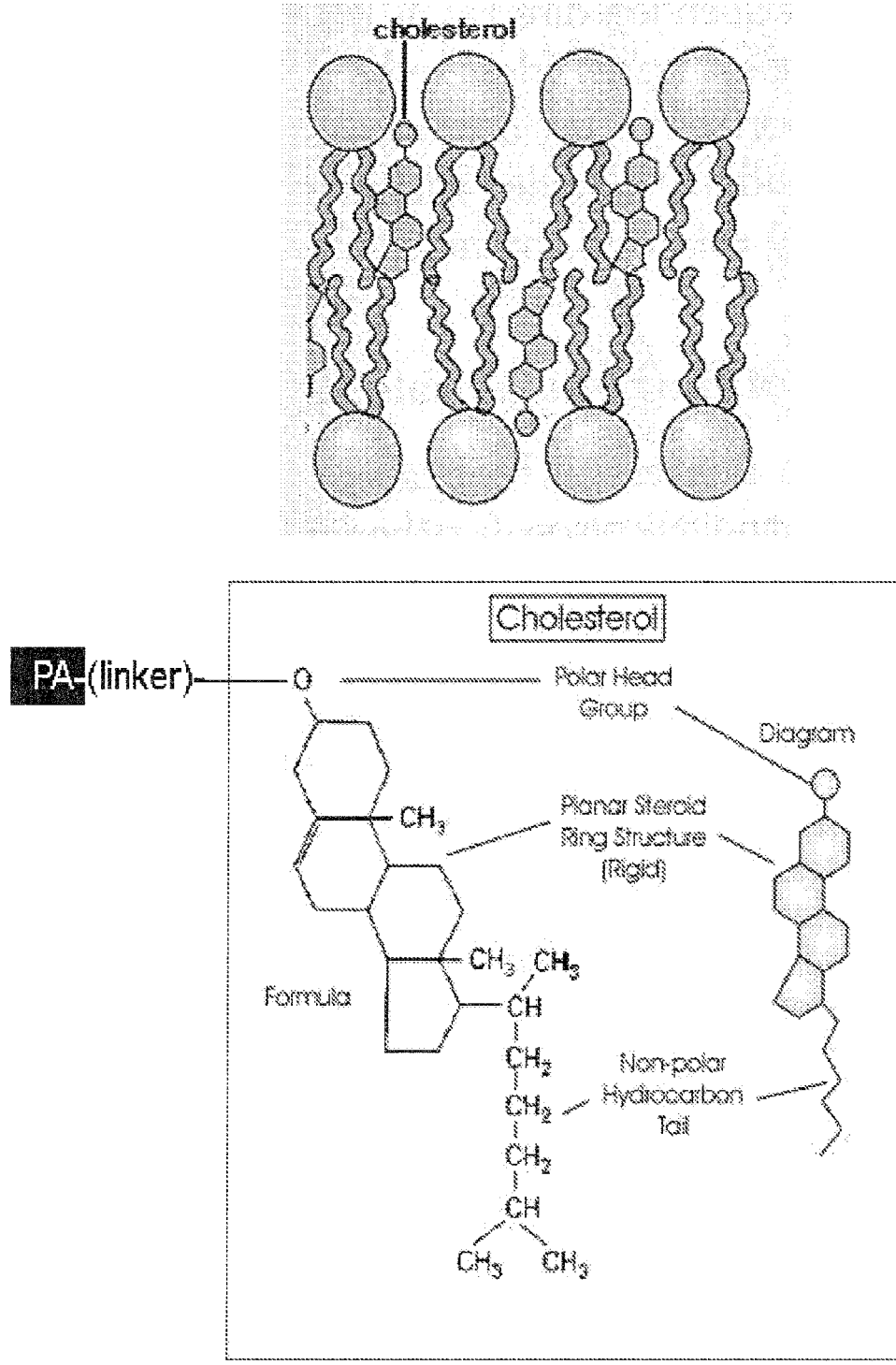
Figure 26A:
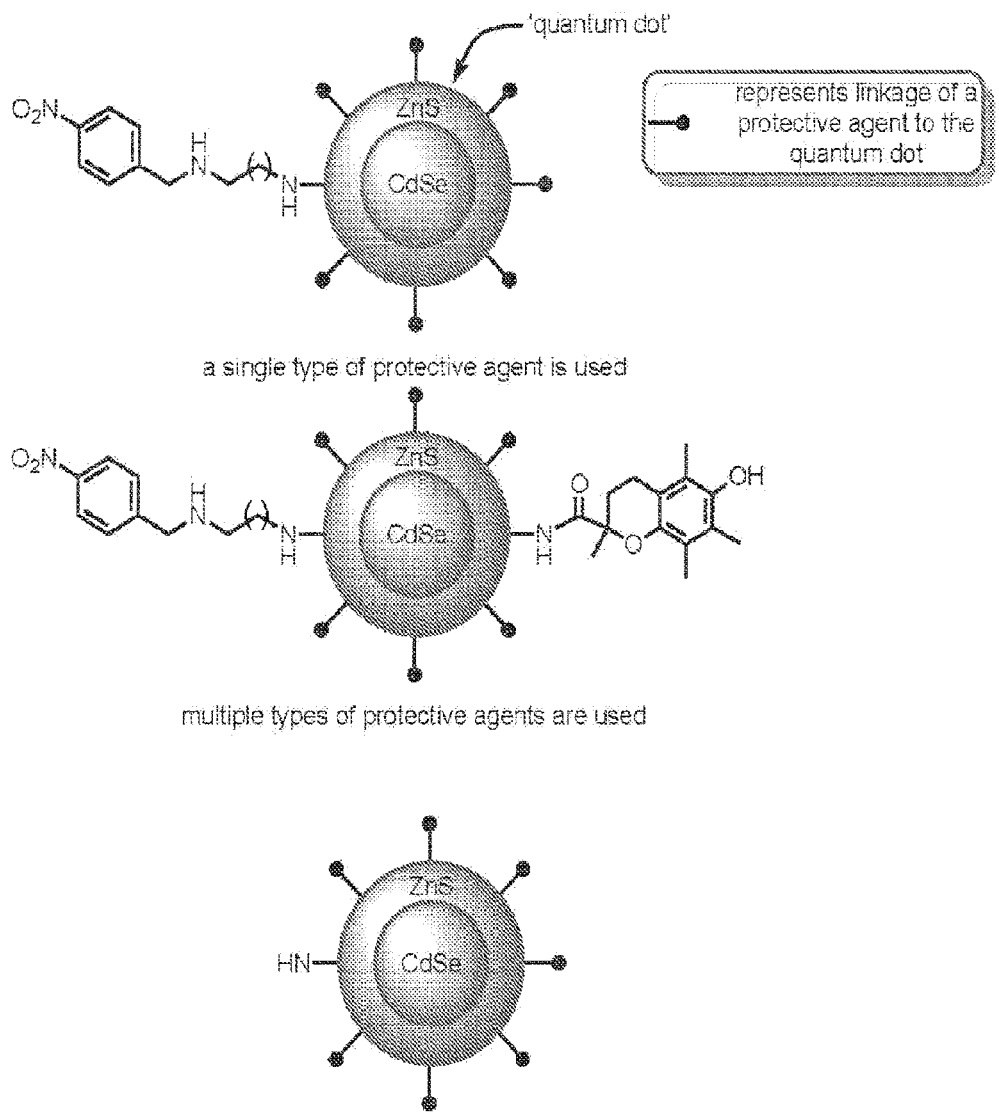
FIGS. 26A-26B. Drawing showing exemplary chemical strategies for the introduction of protective agents onto the exterior of quantum dot compounds. In the cases shown, the protective agent bound can be of a single type, or of multiple types.
Figure 26B:
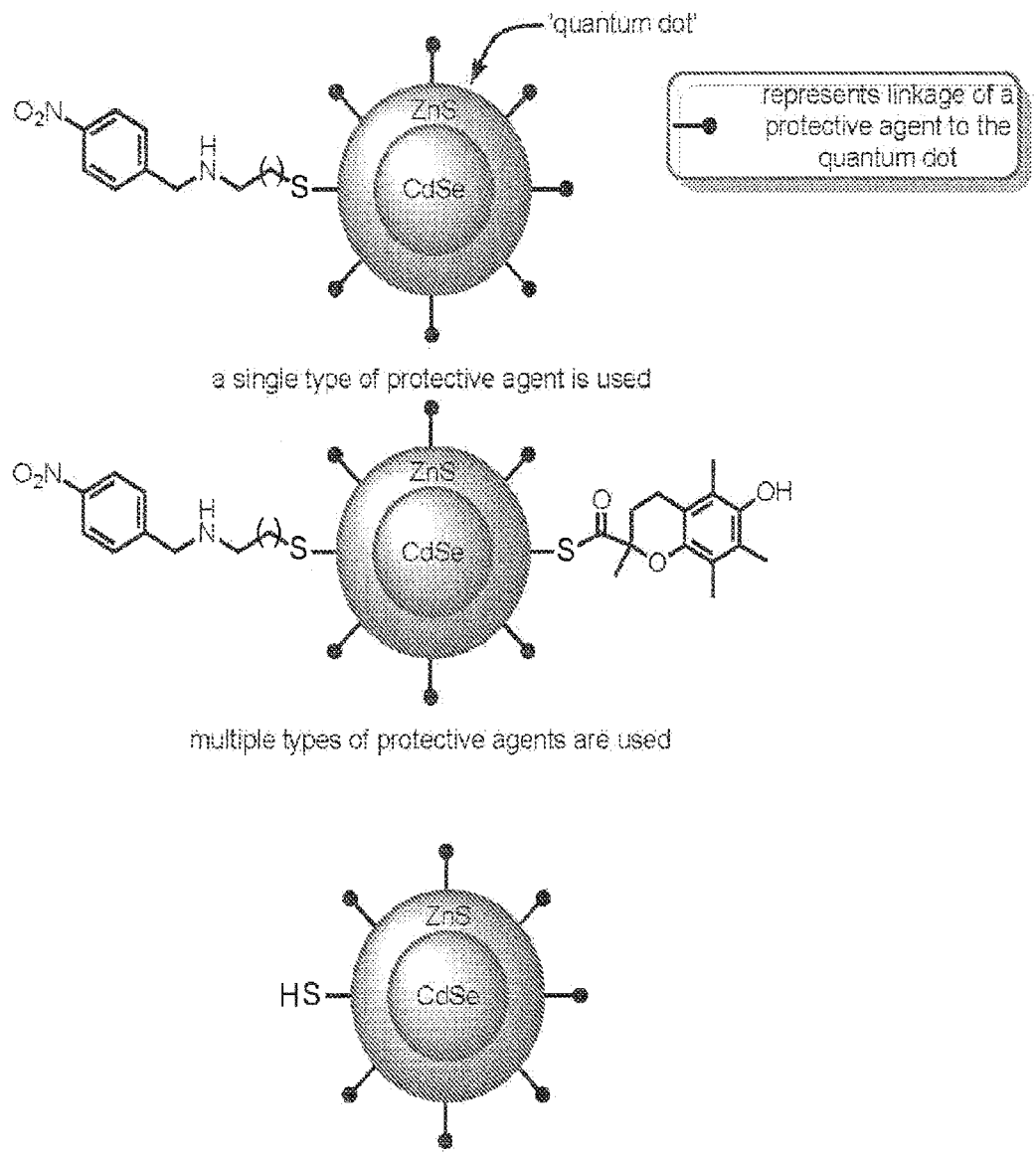
Figure 27:
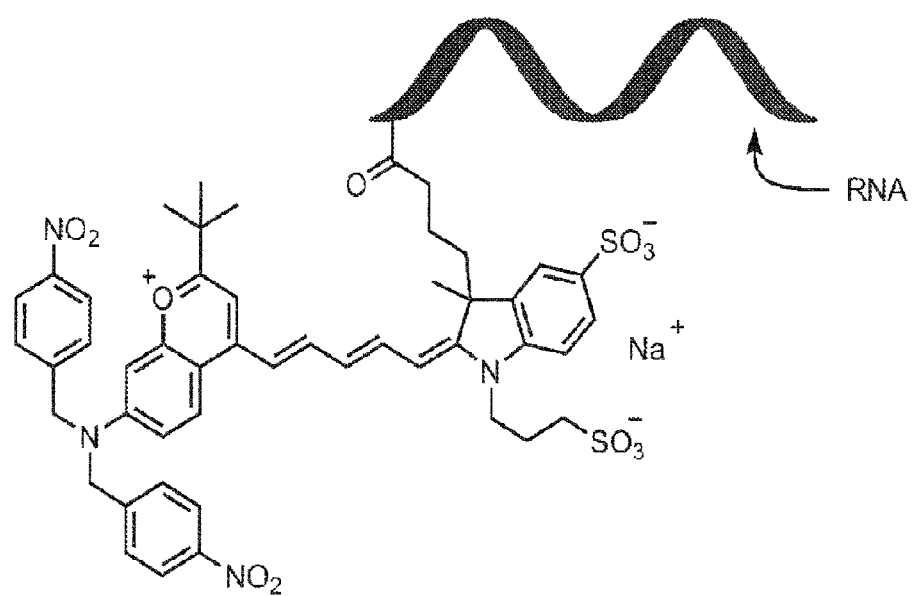
FIG. 27. Drawing showing an exemplary fluorophore-protecting agent conjugate covalently bound to a piece of RNA. Exemplary chemical structure of fluorophore-protective agent conjugate covalently attached to an RNA molecule through a specific reactive moiety present in the fluorophore.
Figure 28:
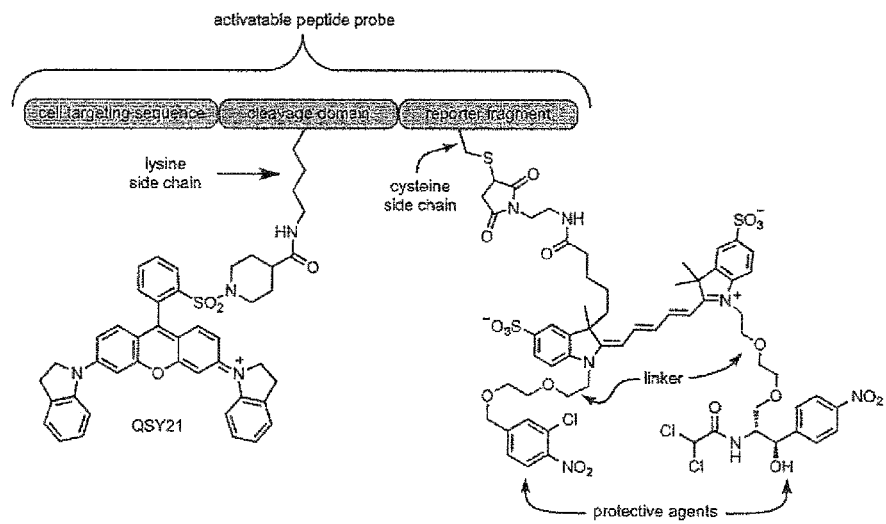
FIG. 28. Strategy whereby a fluorophore-protective agent conjugate is linked to a reporter fragment via a reactive sulfhydryl moiety in close proximity to a quenching agent-cleavage fragment domain. The utility of such probes is exemplified in Barnett, E. A., et al., *Proc. Nat. Acad. Sci.* 2009, 106, 9391-9396. The specific example shown is a peptide construct, but may also be applicable to DNA and/or RNA. Cleavage of the fluorophore-PA conjugate from the cleavage domain liberates the fluorophore-PA conjugate from proximity to the quencher, thereby producing a detectable FRET signal. By modifying the photophysical properties of the liberated fluorophore, the present invention improves one's ability to detect the cleavage reaction via fluorescence.

The nature and/or presence of the fluorescence modifier is not a requirement for fluorescence, however short the lifetime of fluorescence may be. Rather, incorporation of the fluorescence modifier enhances the photophysical properties of the fluorophore, including the lifetime of fluorescence. The drawing shown in FIG. 20 illustrates that the modifier can be connected to the fluorophore via a 'linker', $[XY_n]_m$, and that not only can there be more than one 'linker'-(fluorescence modifier) moiety per fluorophore, but there can also be more than one fluorescence modifier per linker. For example, the general structure can contain up to five modifiers per linker and each fluorophore can contain up to ten linkers. In addition, these molecules can be configured to include a handle such that they can be attached to reactive functional groups on biomolecules and/or other moieties where a fluorescent 'tag' is required.

In the linker shown in FIG. 20, each occurrence of X can be independently, for example, carbon, oxygen, nitrogen, sulfur, or phosphorous; each occurrence of Y can be independently, for example, hydrogen, carbon, oxygen, nitrogen, sulfur, phosphorous, an alkyl, acyl, aromatic, heteroaromatic, aryl, heteroaryl, alkyl(aryl), or alkyl(heteroaryl) group; each occurrence of n can be, independently, for example, an integer of 0, 1, 2, 3, 4, 5, 6, 7, 8, 9, or 10, or within a range therein; each occurrence of in can be, independently, for example, an integer from 0 to 20 or a subrange therein; each occurrence of x can be independently, for example, an integer of 1, 2, 3, 4, or 5, or within a range therein; and each occurrence of y can be independently, for example, an integer of 0, 1, 2, 3, 4, 5, 6, 7, 8, 9, or 10, or within a range therein.

As used herein, a "linker" is a chemical group that connects two, three, or more chemical groups. The linker can, for example, connect a fluorophore to a protective agent, and/or a fluorophore to a biomolecule or surface, and/or a protective agent to a biomolecule or surface. In different embodiments, the linker preferably contains precisely, at least, or no more than one, two, three, four, five, six, seven, eight, nine, ten, eleven, or twelve atom-lengths between linked groups. In one embodiment, the linker is a hydrocarbon linker, e.g., as derived from any of the hydrocarbon groups described above by replacement of two or more hydrogen atoms by a respective number of linking bonds. Some examples of hydrocarbon linkers include methylene, ethylene, trimethylene, tetramethylene, pentamethylene, hexamethylene, o-, m-, and p-phenylene, and vinylene. The hydrocarbon linker may or may not also include heteroatoms. Furthermore, the heteroatoms may or may not be linking atoms. In a particular embodiment, the hydrocarbon linker contains one, two, three, or more amino groups. Some examples of amino-containing linkers include ethylenediamine, 1,3-diaminopropane, 1,4-diaminobutane, 1,5-diaminopentane, 1,6-diaminohexane, diethylenetriamine, triethylenetetramine, and diaminobenzene linkers. In another particular embodiment, the hydrocarbon linker contains one, two, three, or more oxy atoms or hydroxy groups. Some examples of oxy-containing linkers include ethylene glycol, diethylene glycol, triethylene glycol, 2-hydroxypropane, 2,3-dihydroxybutane, dihydroxybenzene, and the polyethylene glycols (i.e., PEG) linkers. In other particular embodiments, the linkers include one, two, three, or more carbonyl groups. Some examples of such linkers include methyl dicarbonyl, ethyl-1,2-dicarbonyl, propyl-1,3-dicarbonyl, butyl-1,4-dicarbonyl, pentyl-1,5-dicarbonyl, and the like. The linker can also be, for example, a polysulfate chain, a mono or polyphosphate chain, an oligonucleotide, oligopeptide, oligosaccharide, nucleotide, nucleoside, nucleobase, dinucleotide, trinucleotide, tetranucleotide, amino acid, dipeptide, tripeptide, tetrapeptide, saccharide, disaccharide, trisaccharide, tetrasaccharide, lipid, or fatty acid.

In particular embodiments, the linker is a rigid linker that forces at least two linked groups to remain at fixed distances from each other or from another molecule. Such rigid linkers can be advantageous in keeping a protective agent group a fixed distance from a fluorophore, or two protective agent groups a fixed distance from each other, and/or a protective agent. A group or fluorophore a fixed distance from a biomolecule or surface. Some examples of rigid linkers are those containing aromatic or heteroaromatic rings, such as linkers that include benzene, styrene, divinylbenzene, biphenyl, triphenyl, or other aromatic rings and polycyclic ring systems. Generally, for the purposes of this application, a biomolecule (i.e., biomolecule of at least 1,000 Daltons, such as a nucleic acid, protein, or polysaccharide) is not considered a linker.

In a first embodiment, the invention is directed to compounds in which a fluorophore is attached to at least one, two, or more protective agent moieties. The fluorophore can be attached (e.g., covalently) to the protective agent groups by any of the linking methodologies known in the art. For example, a commercial mono-reactive fluorophore (e.g., NHS-Cy5) or bis-reactive fluorophore (e.g., bis-NHS-Cy5 or bis-maleimide-Cy5) can be used to link to one or more protective agent molecules containing appropriate reactive groups (e.g., amino, thiol, hydroxy, aldehydic, or ketonic groups). Alternatively, a protective agent molecule can be derivatized with one, two, or more reactive groups, and the reactive protective agent (e.g., NHS-Trolox) reacted with a fluorophore containing appropriate reactive groups (e.g., an amino-containing fluorophore).

In one embodiment, at least two protective agent groups are attached to a fluorophore, and the protective agent groups are within the same chemical class (e.g., two or three protective agent groups bound to the fluorophore are chromanol-derived groups or polyene groups), but may or may not be structurally the same. In another embodiment, at least two protective agent groups are attached to a fluorophore, and the protective agent groups are not within the same chemical class (e.g., one protective agent group is a chromanol-derived or polyene group, while another protective agent group is a nitro-substituted aromatic group, or a bicyclic, tricyclic, or higher cyclic ring system containing at least two, three, or four ring nitrogen atoms, or a phenolic derivative). In one embodiment, one, two, or more protective agent groups are bound directly to a fluorophore (i.e., without a linker). In another embodiment, one, two, or more protective agent groups are bound indirectly to a fluorophore via a linker group, such as any of the linker groups described above. By judicious selection of where the protective agent groups are linked on a fluorophore, the protective agent groups can be made to be a selected distance apart from each other and/or from the fluorophore. For example, the protective agent groups can be linked to the fluorophore such that they are precisely, at least, or no more than one, two, three, four, five, six, seven, eight, nine, ten, eleven, or twelve atom-lengths apart. In some embodiments, the protective agent groups enhance or modify a photophysical property of the fluorophore in a manner that cannot be achieved by each of the protective agent groups individually, i.e., when not paired. In other embodiments, the protective agent groups, in combination, exhibit a synergistic effect in enhancing or appropriately modifying a photophysical property of the fluorophore.

Some examples of fluorophores containing one or more reactive groups, as well as fluorophores containing a protective agent group, are shown in FIGS. 21-24. As shown, the fluorophore-protective agent composition can additionally contain one or more remaining reactive groups to bind to another molecule, e.g., another protective agent, a biomolecule, or a surface.

In an exemplary embodiment, the fluorophore-protective group composition has the following structure:

(19)

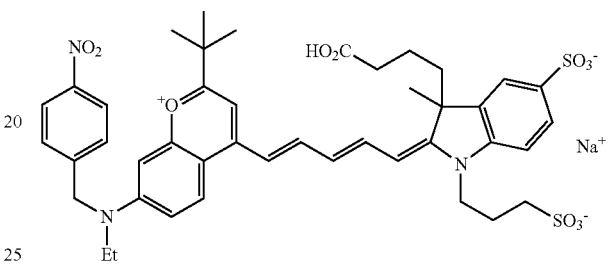

In an exemplary embodiment, the fluorophore-protective group composition has the following structure:

(20)

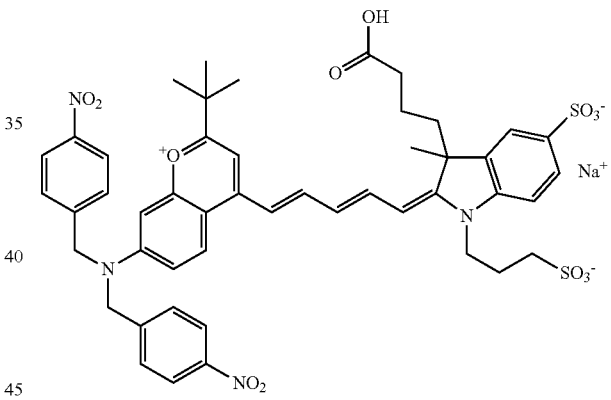

In an exemplary embodiment, the fluorophore-protective group composition has the following structure:

(21)

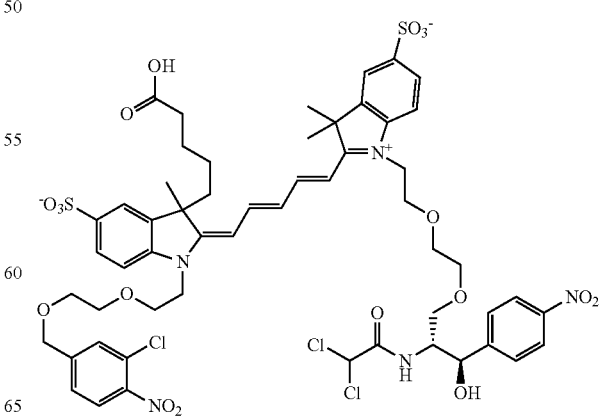

In an exemplary embodiment, the fluorophore-protective group composition has the following structure:
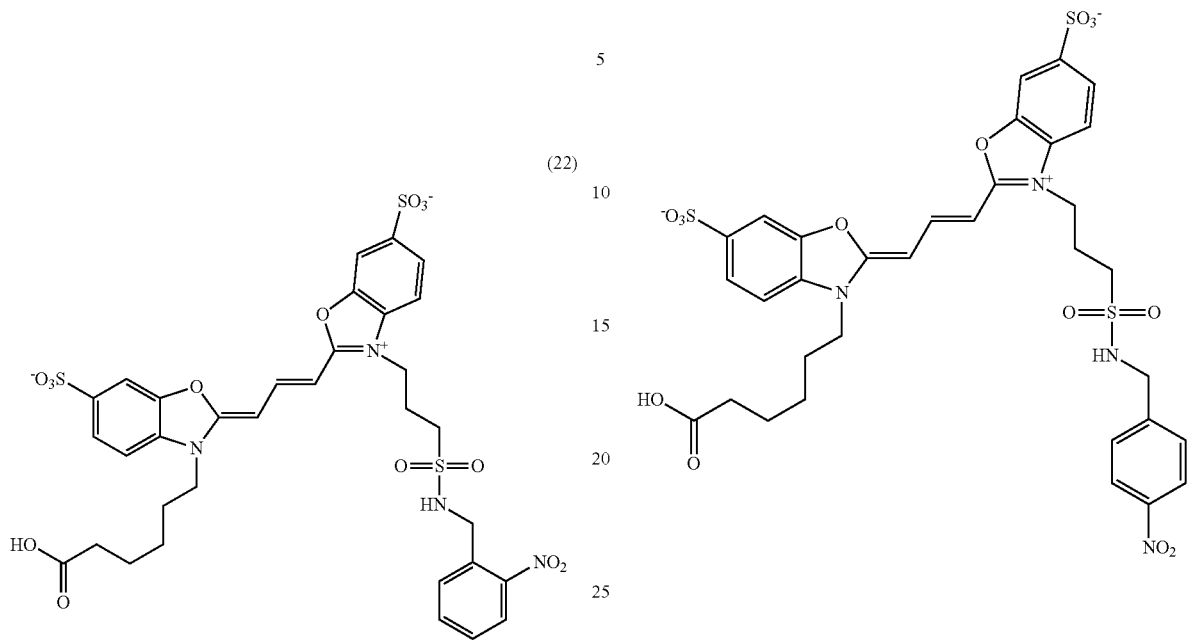
In an exemplary embodiment, the fluorophore-protective group composition has the following structure:
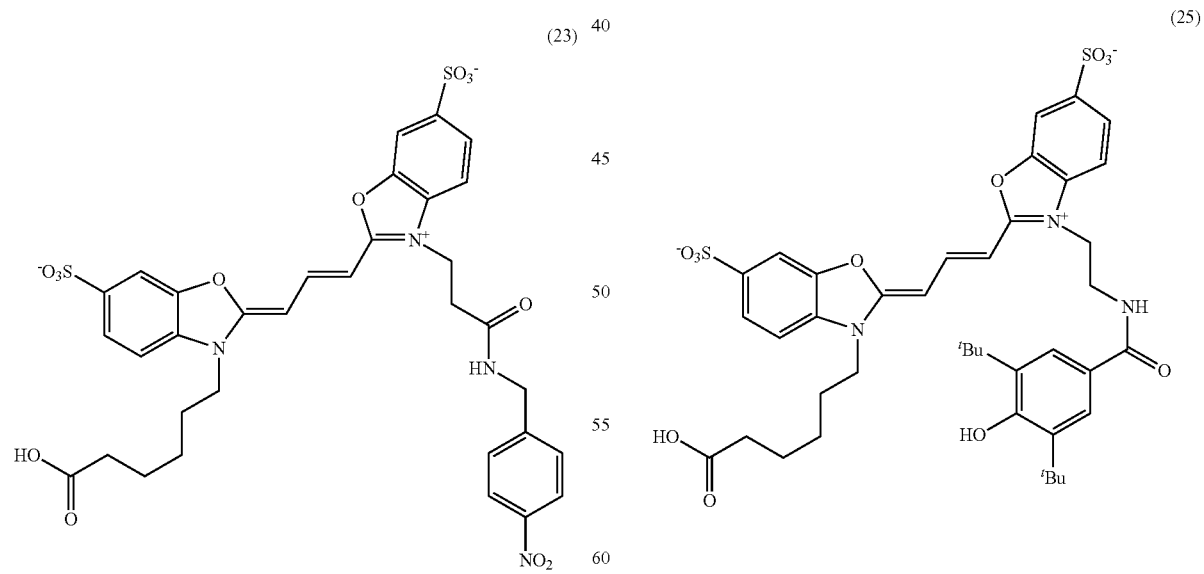
In an exemplary embodiment, the fluorophore-protective group composition has the following structure:

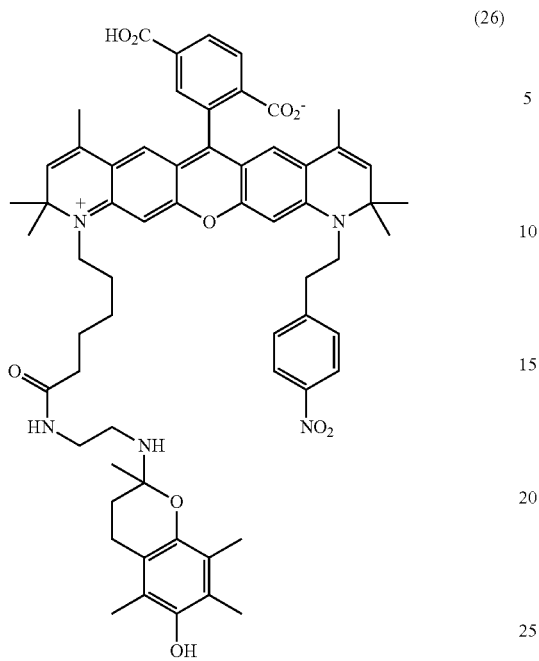
(26)
In an exemplary embodiment, the fluorophore-protective group composition has the following structure:
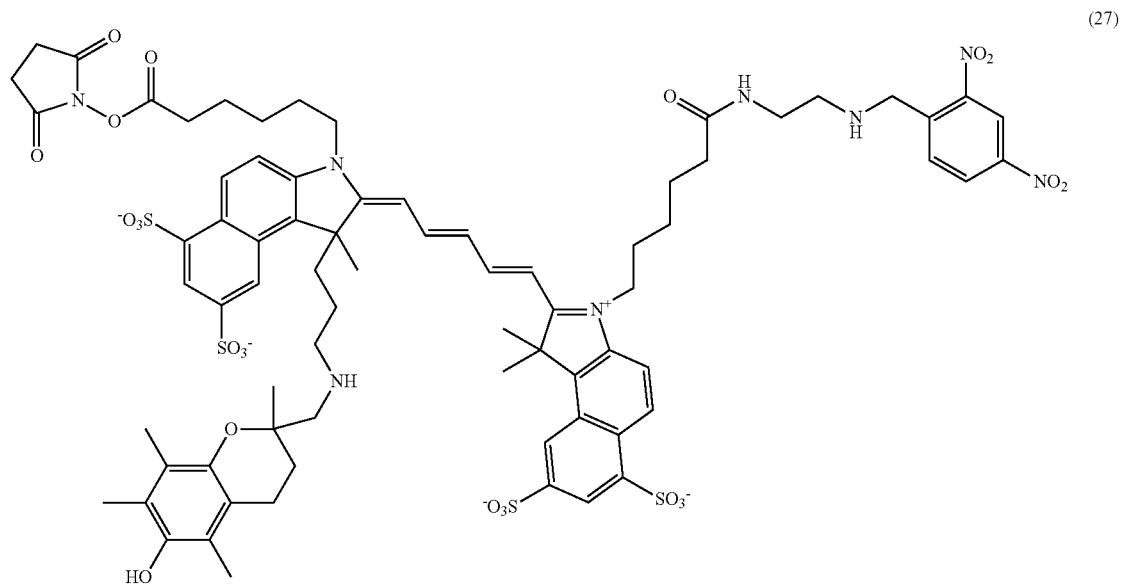
(27)
In an exemplary embodiment, the fluorophore-protective group composition has the following structure:

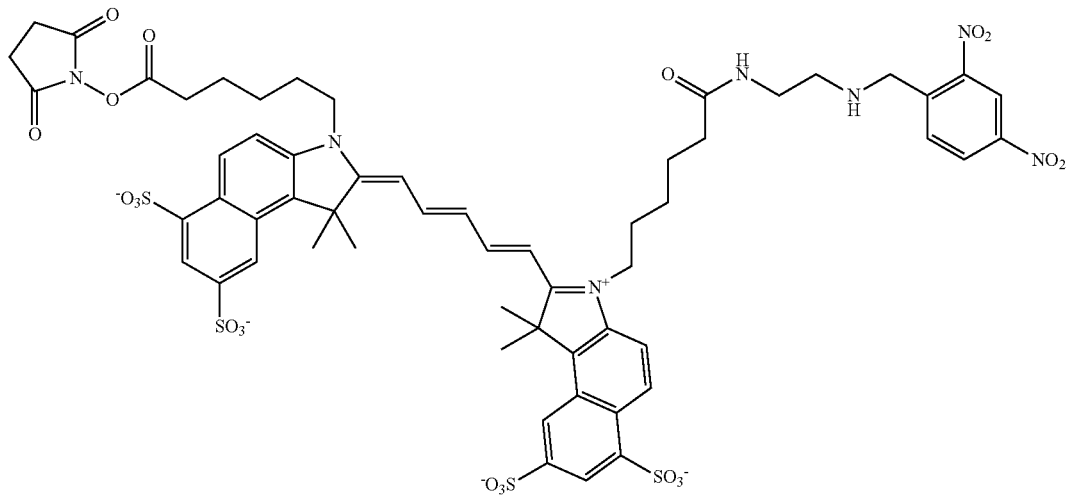

(28)

In another embodiment, the invention is directed to a composition in which a fluorophore and a protective agent molecule are not covalently linked directly or through a linker, but are in sufficient proximity such that the protective agent molecule has an effect on the photophysical properties of the fluorophore. More particularly, the fluorophore and protective agent are close enough to mediate radiative or collisional relaxation of the fluorophore from unwanted, unproductive (i.e., non-fluorescing) excited states or triplet dark states back to productive fluorescing states, such as the singlet excited state, which then relax with concomitant fluorescence emission. For each compound that mediates relaxation of the fluorophore, this benefit may be strongly distance dependent. For example, the ideal proximity of certain protective agents, such as NBA and Trolox, is within about 1-20 Angstroms. The ideal distance may vary substantially for other protective agent (e.g., 1, 2, 5, 10, 15, 20, 25, 30, 35, 40, 45, or 50 Angstroms, or a range thereof, may be ideal).

For example, a fluorophore and protective agent can each be linked to a biomolecule. The biomolecule can be, for example, a nucleic acid (e.g., a DNA or RNA strand), protein, polysaccharide, nucleoprotein, and the like. In particular embodiments, the fluorophore and protective agent are linked at separate specific locations of the biomolecule such that a specified distance separates the fluorophore and protective agent. For example, the fluorophore and protective agent may be on adjacent units of the biomolecule (e.g., adjacent nucleotide, peptide, or saccharide units), or separated by precisely, at least, or no more than one, two, three, four, five, six, seven, eight, nine, ten, eleven, twelve, thirteen, fourteen, fifteen, sixteen, seventeen, eighteen, nineteen, or twenty units. In the case of a nucleic acid, the fluorophore and protective agent can be independently attached to the base, phosphate, or sugar moiety. In the case of a protein, the fluorophore and protective agent can be independently attached to, for example, the amido backbone —NH group, or particular amino acid side chains (e.g., phenolic groups of tyrosine, or amino groups of lysine, arginine, histidine, asparagine, or glutamine, or thiol groups of cysteine, or hydroxy groups of serine or threonine, or carboxylic acid groups of aspartate or glutamate). It is also envisaged that a biomolecule is chemically tailored to contain certain chemical groups that specifically bind to (optionally, when activated) a fluorophore and/or protective agent.

A fluorophore and/or protective agent can also be site-specifically incorporated into a protein. For example, by use of orthogonal chemistries, site-specific incorporation of a fluorophore or protective agent can be accomplished by non-natural amino acid incorporation, post-translational modifying enzymes, or c-terminal ligation. (Reference is made to Muir T. Annu Rev. Biochem. Vol. 72 pg. 249-89 (2003); Ryu Y and Schultz P G. Nat. Methods Vol. 3(4) pg 263-5 (2006); Wang L, Xie J, Deniz, A A and Schultz P G J. Org. Chem. Vol 68(1) pg 174-6 (2003); Chin, J W, Cropp T A, Anderson J C, Mukherji M, Zhang Z, Schultz P G Science Vol. 299(5615) pg. 2045-7 (2003); Warren, J. D., et al. *J. Am. Chem. Soc.*, 2004, Vol. 126, pg. 6576-6578; Yin Y, Lin A J, Golan D E, Walsh C T. Nat. Protoc. Vol. 1(1) pg. 280-5 (2006), all of which are incorporated herein by reference in their entirety).

In a particular embodiment, the biomolecule on which the fluorophore and/or protective agent is attached is a fluorescent protein. The fluorescent protein can be, for example, a green fluorescent protein (GFP) and its mutated allelic forms (e.g., blue, cyan, and yellow fluorescent proteins) and red fluorescent protein (RFP), and genetic variants thereof. Another example of a fluorescent protein is mCherry and genetic variants thereof. Positions containing Tyrosine, Tryptophan, or Phenylalanine are preferred so that the introduction of non-natural, aromatic amino acid would have minimal perturbation to the system while having the maximal beneficial effect. Residues must also be within 1-20 Å to promote proximity effects. Specific residue to be targeted Tyr203 in the active site of the protein. Selection efforts may also be necessary to screen for secondary mutations that ensure folding and stability of the protein (Reference is made to Hiem R, Cubitt A B, Tsien R Nature Vol. 373(6516) pg. 663-4 (1995), which is incorporated herein by reference in its entirety).

As another example of a fluorophore and protective agent being in proximity without being linked is an embodiment in which either the fluorophore or protective agent is incorporated into a vesicle. The vesicle can be any vesicle known in the art capable of retaining molecules therein. In one embodiment, the vesicle is composed of any of the lipid bilayer membranes (e.g., micelles, liposomes, and proteoliposomes) known in the art. As is well known in the art, the units making up the lipid bilayer are typically amphiphilic. A common class of amphiphilic compounds useful for forming micelles and liposomes is the class of phospholipids; however, several other membrane units are known. Some subclasses of the phospholipids are the phosphatidylcholines and the phosphatidylethanolamines. In another embodiment, the vesicle is composed of any of the polymer membranes known in the art. Some polymer membranes include those based on polyethyleneoxides, polyesters, polyamines, polyethylenes, polystyrenes, polyurethanes, and block copolymers thereof. In particular embodiments, the protective agent is within a vesicle while the fluorophore is on the outside surface of the vesicle, or alternatively, the fluorophore is within a vesicle while the protective agent is on the outside surface of the vesicle. By being "within" the vesicle is meant that the fluorophore or protective agent molecule is floating within a liquid matrix within the vesicle, or the fluorophore or protective agent molecule is attached, either directly or via a linker, to the inner wall of the vesicle. By being "outside" the vesicle is generally meant that the fluorophore or protective agent molecule is attached, either directly or via a linker, to the outer surface of the vesicle. The bond between the fluorophore and/or protective agent and inner or outer surface of the vesicle can be covalent or non-covalent (i.e., electrostatic, van der Waals, or hydrogen bonds). The inner and/or outer surface of the vesicle can be appropriately functionalized for this purpose by methods known in the art. The vesicle can also be either unilamellar or multilamellar. In particular embodiments, both the fluorophore and protective agent are either within the vesicle or on the outer surface of the vesicle. At least one specific advantage of this type of configuration is for the study of integral- or membrane-associated biomolecule function, such as in the study of neurotransmitter or neurotransporter protein function in the nerve synapse as related to neurotransmitter re-uptake following synaptic transmission. The use of vesicles also permits the study of cell-derived membrane extract fractions that are not amenable to direct surface immobilization strategies.

In particular embodiments, the protective agent is directly attached to a lipid head group or within the lipid bilayer (e.g., by linking to a sterol, such as cholesterol) so that it is in close proximity to the fluorophore, yet not covalently attached to the fluorophore. In such an embodiment, the protective agent can be attached to the external or internal environment of the lipid vesicle. In a preferred embodiment, the vesicle surrounds the biomolecule of interest (e.g., a ribosome), thereby providing a protective and controlled environment for the biomolecule. The foregoing embodiment can be particularly useful in the imaging of the encapsulated biomolecule. Such embodiments may utilize one or numerous (e.g., hundreds) of protective agents that are the same or diverse. The vesicle may also be porous so that the protective agents can penetrate the interior in order to achieve high effective concentrations, yet exchange with the interior to maintain/replenish the protective agent concentration over time. Such encapsulation strategies can advantageously provide for a controlled microenvironment that could accommodate a wide range of biomolecules diverse in both composition and size. Alternatively, the protective agents could be attached or embedded into or onto a lipid bilayer that is not a vesicle or liposome. Such an approach may include nanodiscs (e.g., Bayburt T H, Sligar S G FEBS Lett. October 16. Epub (2009) or other similar lipid bilayer architecture. Alternatively, the protective agent could be encapsulated into or onto a virus capsid such that a fluorescently labeled biomolecule of interest either inside or outside the virus capsid benefits from the proximity of one or more protective agents. Viral capsid proteins are robust to mutation as demonstrated by phage display technologies (e.g., Smith G P Science Vol. 228(4705) pg. 1315-7 (1985) and variants able to pass screening procedures can be amplified (Smith G P Petrenko V A Chem. Rev. Vol. 97(2) pg. 391-410 (1997). Viral capsid proteins also assemble in close proximity so that the incorporation of non-natural amino acids (protective agents) could be densely packed.

The vesicle size is typically in the range of, e.g., about, at least, or no more than 0.1, 0.2, 0.3, 0.4, 0.5, 0.6, 0.7, 0.8, 0.9, 1, 2, 5, 10, 15, 20, 25, 30, 35, 40, 45, or 50 microns, or within a range therein. However, significantly smaller vesicles are possible (e.g., nanosomes), with sizes of, e.g., about, at least, or no more than 1, 2, 5, 10, 20, 30, 40, 50, 60, 70, 80, or 90 nm, or within a range therein.

As another example of a fluorophore and protective agent being in proximity without being linked is an embodiment in which a protective agent is placed on the surface of a quantum dot nanoparticle or other nanoparticle. The protective agent can reside on the surface of the quantum dot by any mode of attachment, e.g., covalent or non-covalent (i.e., by electrostatic, van der Waals, or hydrogen bonds) modes of attachment. In some embodiments, reactive groups suitable for the attachment of one or more protective agents is included either within or on the surface of the quantum dot, such as within the first passivation layer present in commercially available quantum dots (see, for example, FIG. 15).

The quantum dots, either during or after their formation, are often surface functionalized with hydrophilic or hydrophobic groups (e.g., surface capping groups, such as long chain thiols, carboxylates, or phosphates, or polymers). Long chain amphiphilic molecules generally produce an ordered capping surface on the quantum dot known in the art as a "self-assembled monolayer". Some examples of metal-binding polymers suitable for stabilizing or functionalizing quantum dot particles include the dextrans (e.g., carboxymethyl dextran), dextroses, celluloses and their derivatives, polyethylene oxides or glycols (PEGs), albumin, and the like.

As known in the art, the surface capping groups can be functionalized with one or more reactive groups (e.g., amino, carboxy, epoxy, aldehyde, alkyl halide, iodoacetamide, isocyanate, hydrazido, or semicarbazide groups) suitable for attaching to the fluorophore, protective agent, and/or another molecule, such as a biomolecule. The protective agent may thus be incorporated in a first, second, or third passivation shell or doped or impregnated in the core material. In some embodiments, the reactive group is capable of binding to a molecule without being activated in some manner, whereas in other embodiments the reactive group is activated in order to bind to the molecule. Alternatively, a functional group of the fluorophore, protective agent, and/or other molecule, such as a biomolecule, is activated or converted by a linking group to a group capable of reacting with a group on the surface of the quantum dot.

A bis-reactive linking molecule can also be used to link the surface of the quantum dot (or other type of nanoparticle or vesicle) with a fluorophore, protective agent, or other molecule, such as a biomolecule. For example, amino-amino coupling reagents can be employed to link an amino group of a passivation molecule or polymer, or vesicle membrane, with an amino group of a fluorophore, protective agent, or other molecule. Some examples of suitable amino-amino coupling reagents include diisocyanates, alkyl dihalides, dialdehydes, disuccinimidyl suberate (DSS), disuccinimidyl tartrate (DST), and disulfosuccinimidyl tartrate (sulfo-DST), all of which are commercially available. Or, for example, amino-thiol coupling agents can be employed to link a thiol group of a passivation molecule or polymer, or vesicle membrane, with an amino group of the fluorophore, protective agent, or other molecule. Some examples of suitable amino-thiol coupling reagents include succinimidyl 4-(N-maleimidomethyl)-cyclohexane-1-carboxylate (SMCC), and sulfosuccinimidyl 4-(N-maleimidomethyl)-cyclohexane-1-carboxylate (sulfo-SMCC).

Other linking chemistries are possible. For example, the quantum dot, other nanoparticle, or vesicle can be linked to a fluorophore, protective agent, biomolecule, or a surface, by use of known strong and selective interactions between certain pairs of biomolecules. For example, in one embodiment, an amino-functionalized nanoparticle or vesicle can be reacted with an amine-reactive biotinylation reagent to functionalize the nanoparticle or vesicle with biotin. Some examples of amine-reactive biotinylation reagents include the class of molecules containing biotin on one end and, for example, a succinimide ester, pentafluorophenyl ester, or alkyl halide group on the other end. The biotin group and amine-reactive group can be separated by any suitable spacer group of any length (e.g., 5-40 Å in length). Some examples of amine-reactive biotinylation reagents are available from Pierce under the EZ-Link® trade name, e.g., as NHS-biotin (containing a five-carbon ester linkage between biotin and NHS), sulfo-NHS-biotin, NHS-LC-biotin, and sulfo-NHS-LC-Biotin, NHS-LC-LC-biotin, sulfo-NHS-LC-LC-biotin, sulfo-NHS-SS-biotin, NHS-PEO$_4$-biotin, PFP-biotin, TFP-PEO-biotin, and the like, wherein "NHS" refers to a N-hydroxysuccinimide group, "LC" refers to a six-carbon amide-containing linkage inserted between the NHS group and biotin or between another LC group and biotin, "PEO" refers to an ethylene oxide group, wherein the associated subscript indicates the number of linked PEO units, "PFP" refers to a pentafluorophenyl group, "TFP" refers to a tetrafluorophenyl group, "sulfo" refers to a sulfonate ($SO_3^-Na^+$) group, and "SS" refers to a disulfide bond.

In another embodiment, a thiol-functionalized nanoparticle or vesicle can be reacted with a thiol-reactive biotinylation reagent to functionalize the nanoparticle or vesicle with biotin. Some examples of thiol-reactive biotinylation reagents include the class of molecules containing biotin on one end and, for example, a maleimido or alkyl halide group on the other end. The biotin group and thiol-reactive group can be separated by any suitable spacer group of any length, as above. Some examples of thiol-reactive biotinylation reagents are available from Pierce under the EZ-Link® trade name, e.g., as maleimide-PEO$_2$-biotin, biotin-BMCC (contains an end-maleimido group and one cyclohexyl, two amide linkages, and nine additional linking carbon atoms), PEO-iodoacetyl biotin, iodoacetyl-LC-biotin, biotin-HPDP (contains a pyridyl disulfide group), and the like.

The biotin-functionalized nanoparticle or vesicle can then be reacted with an avidin or streptavidin-functionalized fluorophore molecule, protective agent molecule, biomolecule, or surface, such that a nanoparticle or vesicle complex is produced which contains the nanoparticle or vesicle conjugated to the fluorophore and/or protective agent and/or biomolecule and/or surface via a biotin-avidin or biotin-streptavidin In an analogous embodiment, the nanoparticle or vesicle is conjugated to avidin or streptavidin and the avidin- or streptavidin-functionalized nanoparticle or vesicle reacted with a biotinylated fluorophore, protective agent, biomolecule, or surface, such that a nanoparticle or vesicle complex is produced which contains the nanoparticle or vesicle conjugated to the fluorophore and/or protective agent and/or biomolecule and/or surface via an avidin-biotin or streptavidin-biotin link. Similar embodiments are envisaged by use of antibody pairs, or by selective metal-ligand linkages, e.g., nickel-NTA linkage.

Figure 9A:
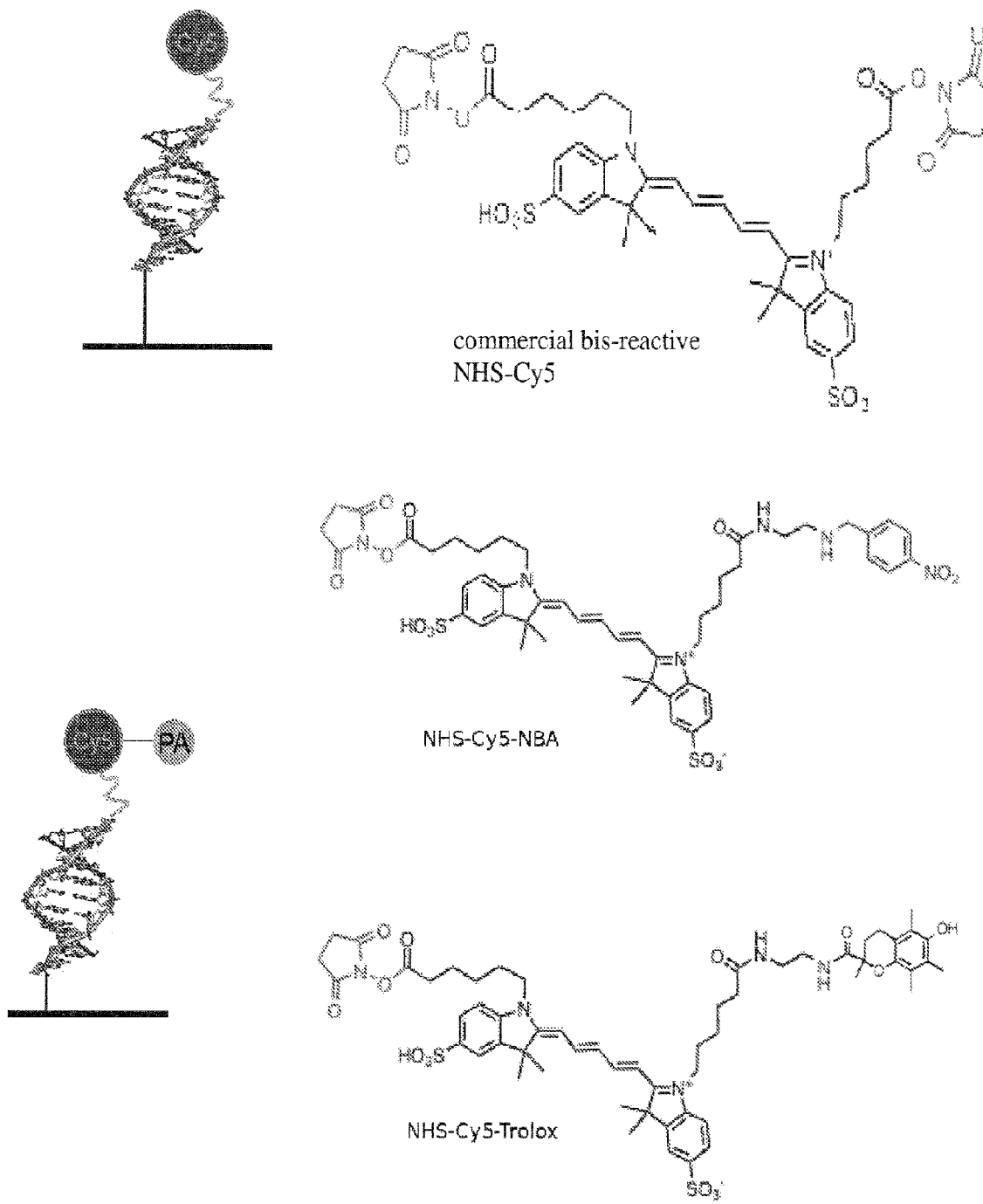
FIGS. 9A-9B. Experimental data taken as described in FIG. 8 here showing the lifetime of Cy5 fluorescence ($t_{on}$) is greatly improved (>10-fold) by its direct linkage to either NBA or Trolox. Cy5- and Cy5-PA fluorescence behaviors were interrogated in the context of its linkage to DNA as schematized using the single-molecule TIR scheme shown in FIG. 2. The specific dye molecules examined are shown. These data demonstrate that the same protective agents examined for the Cy3 fluorophore operate either through distinct mechanisms or to different extents on the Cy5 fluorophore.
Figure 9B:
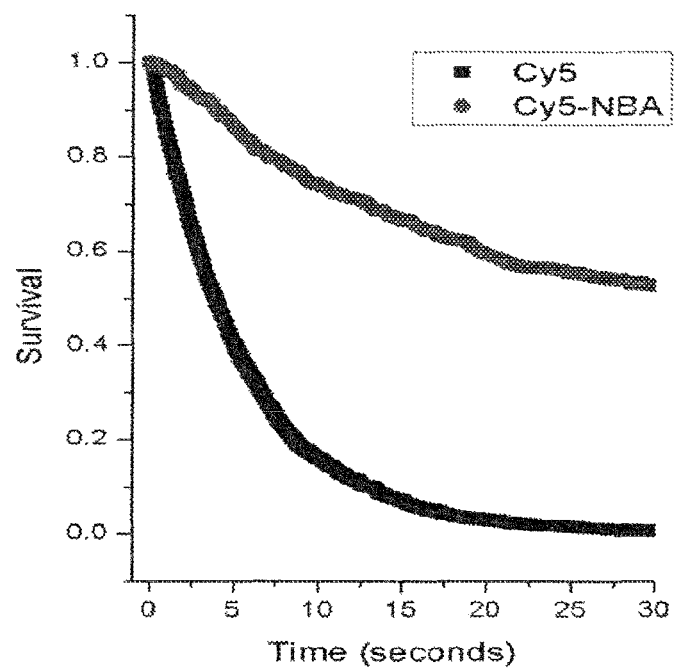
Figure 9B:
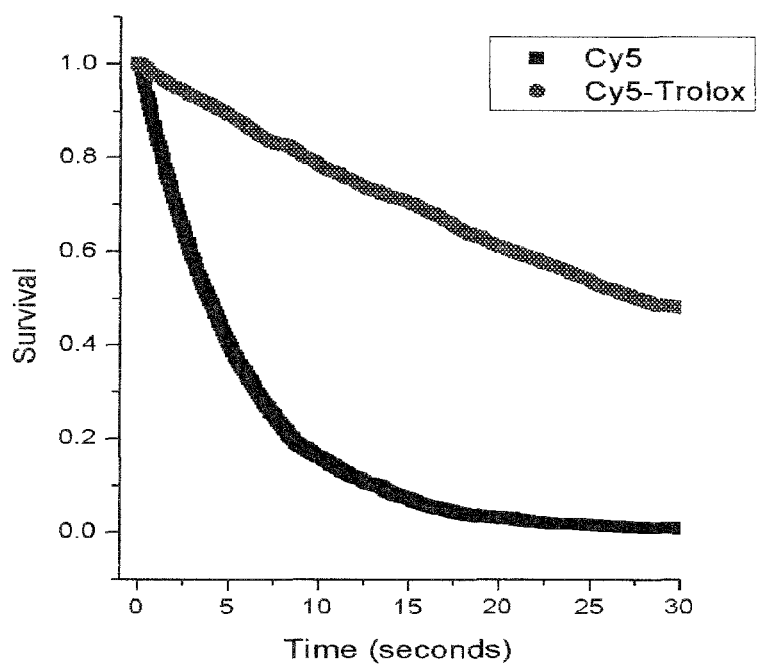
Figure 10A:
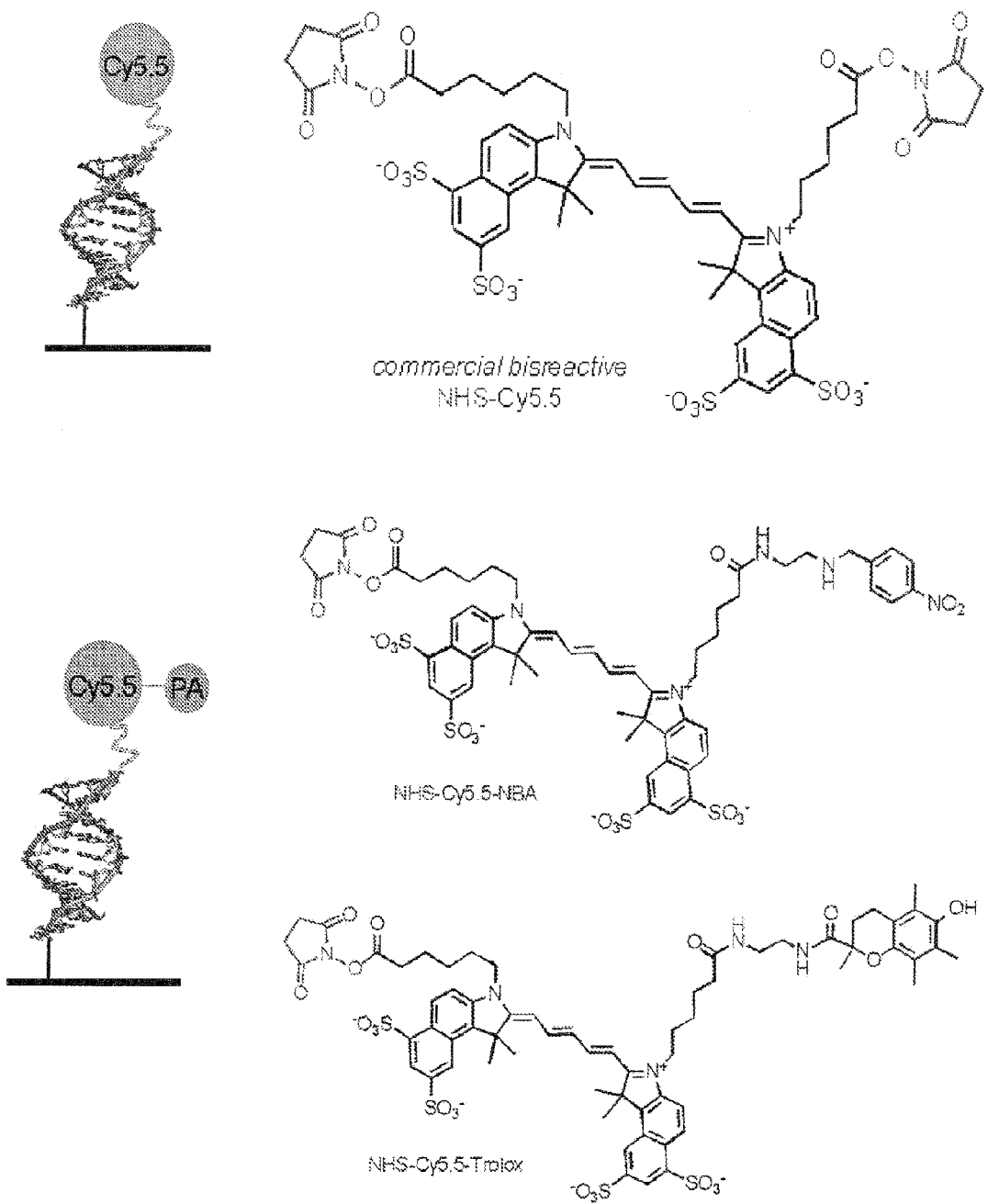
FIGS. 10A-10B. Experimental data taken as described in FIG. 8 showing the lifetime of Cy5.5 fluorescence ($t_{on}$) is greatly improved (>20-fold) by its direct linkage to either NBA or Trolox. Cy5.5 and Cy5.5-PA fluorescence behaviors were interrogated in the context of its linkage to DNA as schematized using the single-molecule TIR scheme shown in FIG. 2. The specific dye molecules examined are shown. In yet another example that distinct protective agents operate either through distinct mechanisms or to different extents on fluorophore species, Trolox and NBA are shown to improve the photophysical properties of the Cy5.5 fluorophore more substantially than both Cy3 and Cy5.
Figure 10B:
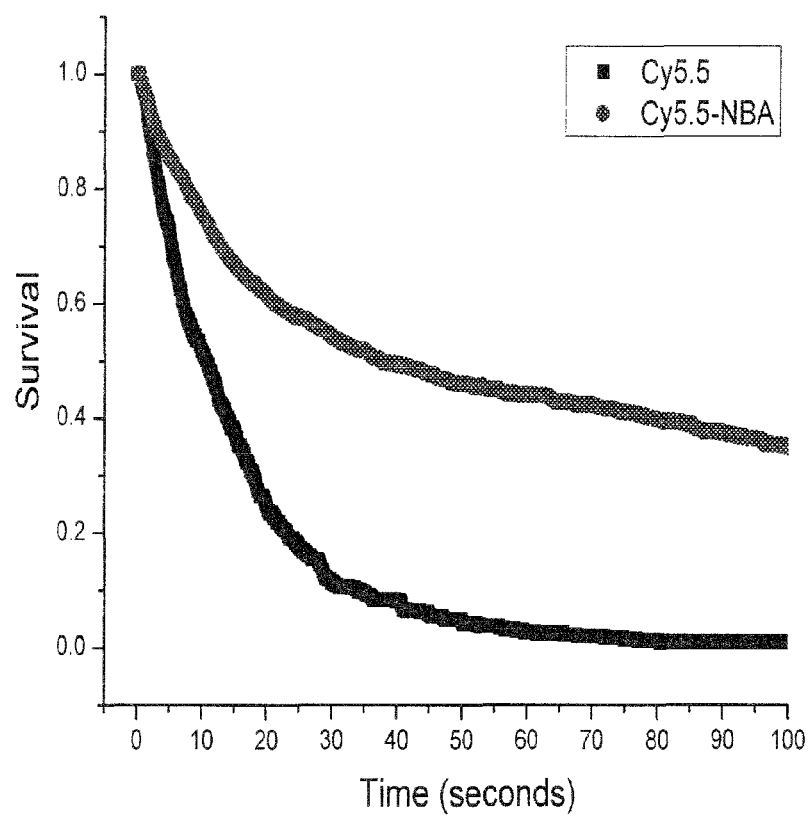
Figure 10B:
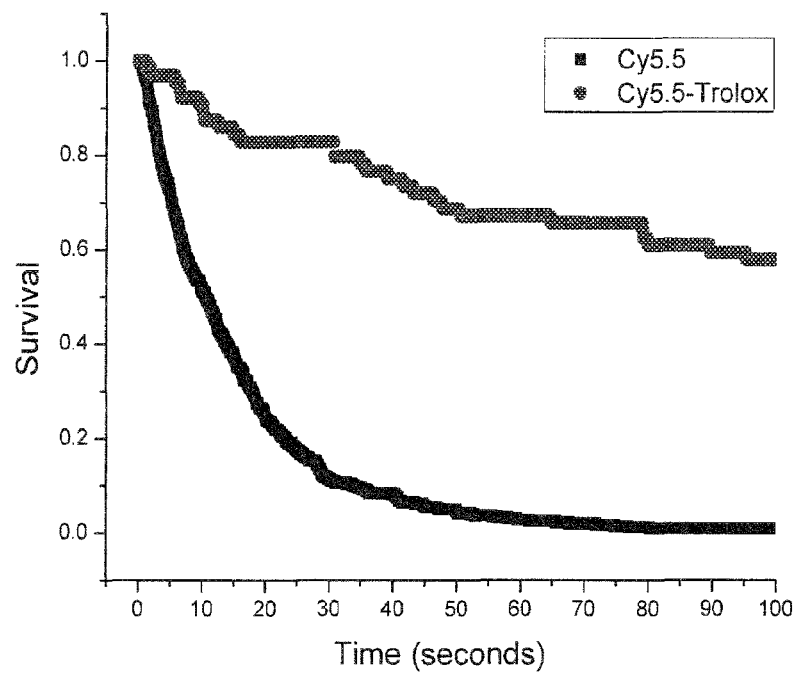
Figure 11A:
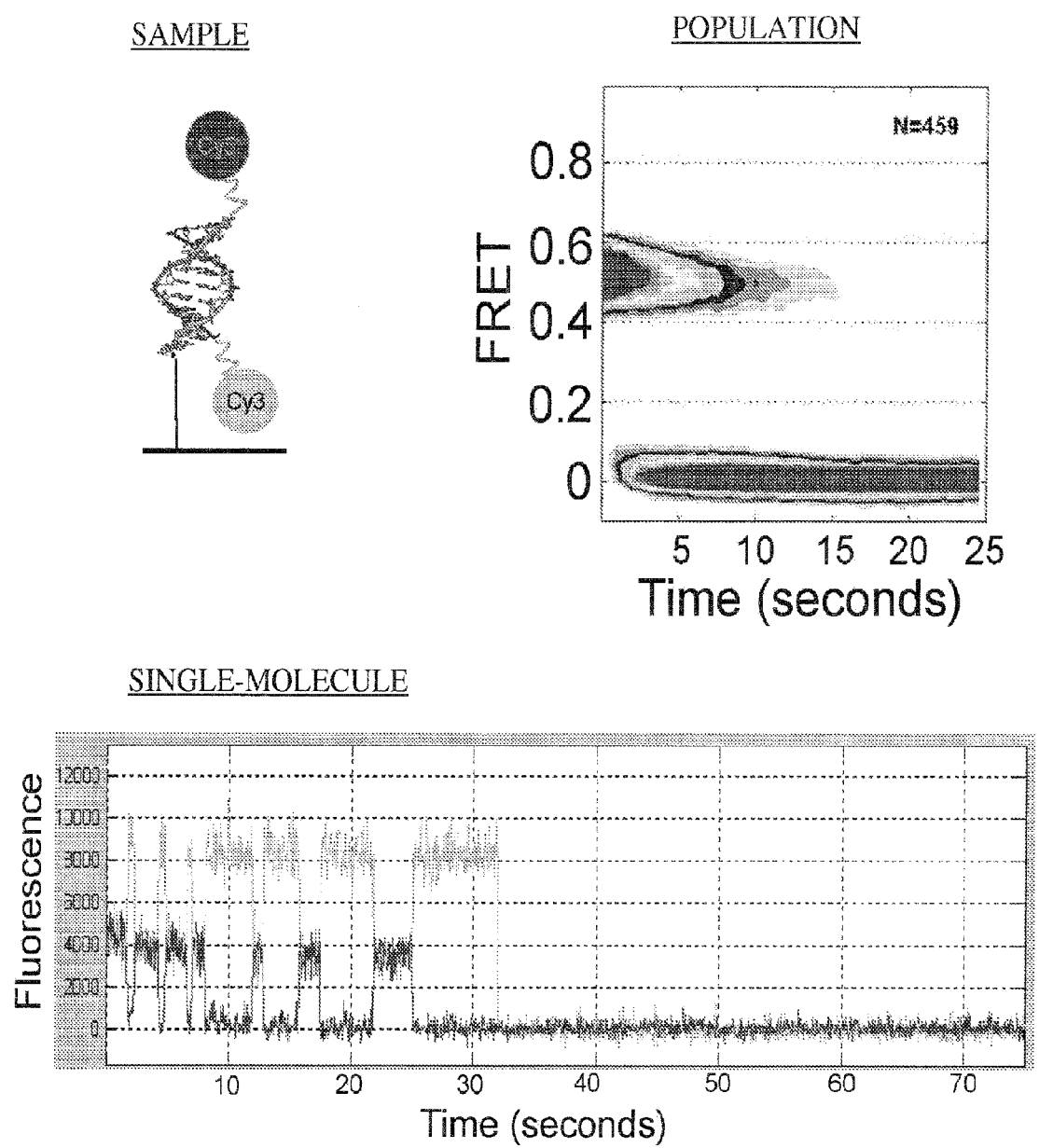
FIGS. 11A-11D. Experimental data demonstrating improvements in the informative FRET lifetime for the Cy3 and Cy5 pair. (Left panels) specific samples interrogated in which no protective agent is present, NBA is linked to Cy5, Trolox is linked Cy5 or a sample where distinct protective agents are linked to each fluorophore: NBA is linked to Cy5 and Trolox is linked Cy3. (Middle panels) Experimental single-molecule FRET data showing examples of Cy3 and Cy5 fluorescence. Experimental data showing the population FRET behaviors observed where each of the constructs containing fluorophore-PA conjugates has an extended FRET duration. In the sample where each fluorophore of the FRET pair is linked to a protective agent (bottom panels), the total lifetime of FRET is greatly improved over samples containing no protective agents (>20-fold) and significantly improved over samples where only the Cy5-fluorophore is linked to a protective agent (>2-fold) (note the time axes on the bottom panels represent a much longer imaging period than the others shown). By increasing the FRET duration and minimizing dark states, the information content of the experiment is substantially improved. By extending the FRET duration, more robust structural information can be obtained (as required for "Molecular EKG" imaging (Blanchard SC Curr Opin Struct. Biol Vol. 19(1) pg. 103-9 (2009)) and/or greater confidence in the localization of single-fluorophores when tracking blinking kinetics (as for super-resolution imaging).
Figure 11B:
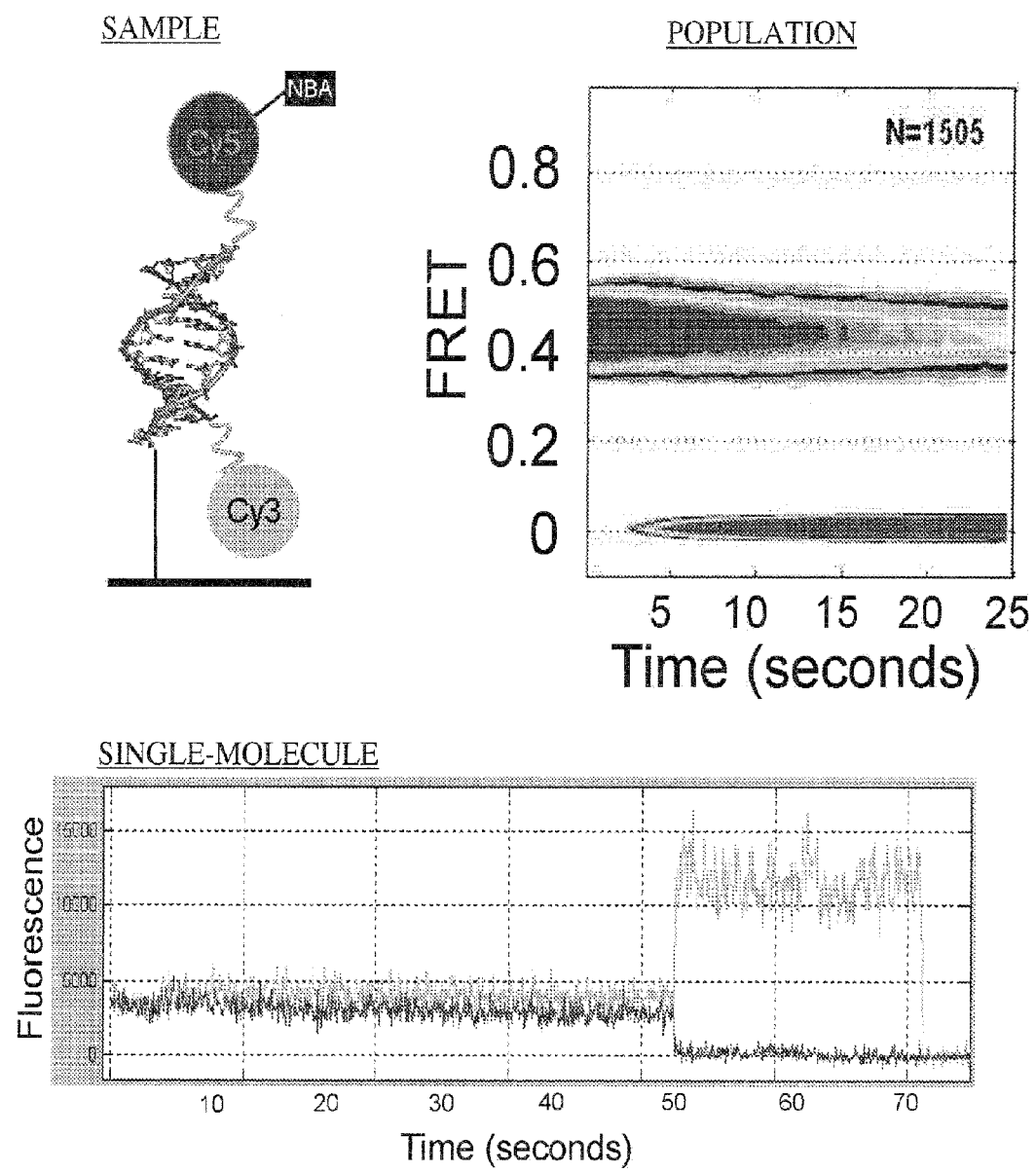
Figure 11C:
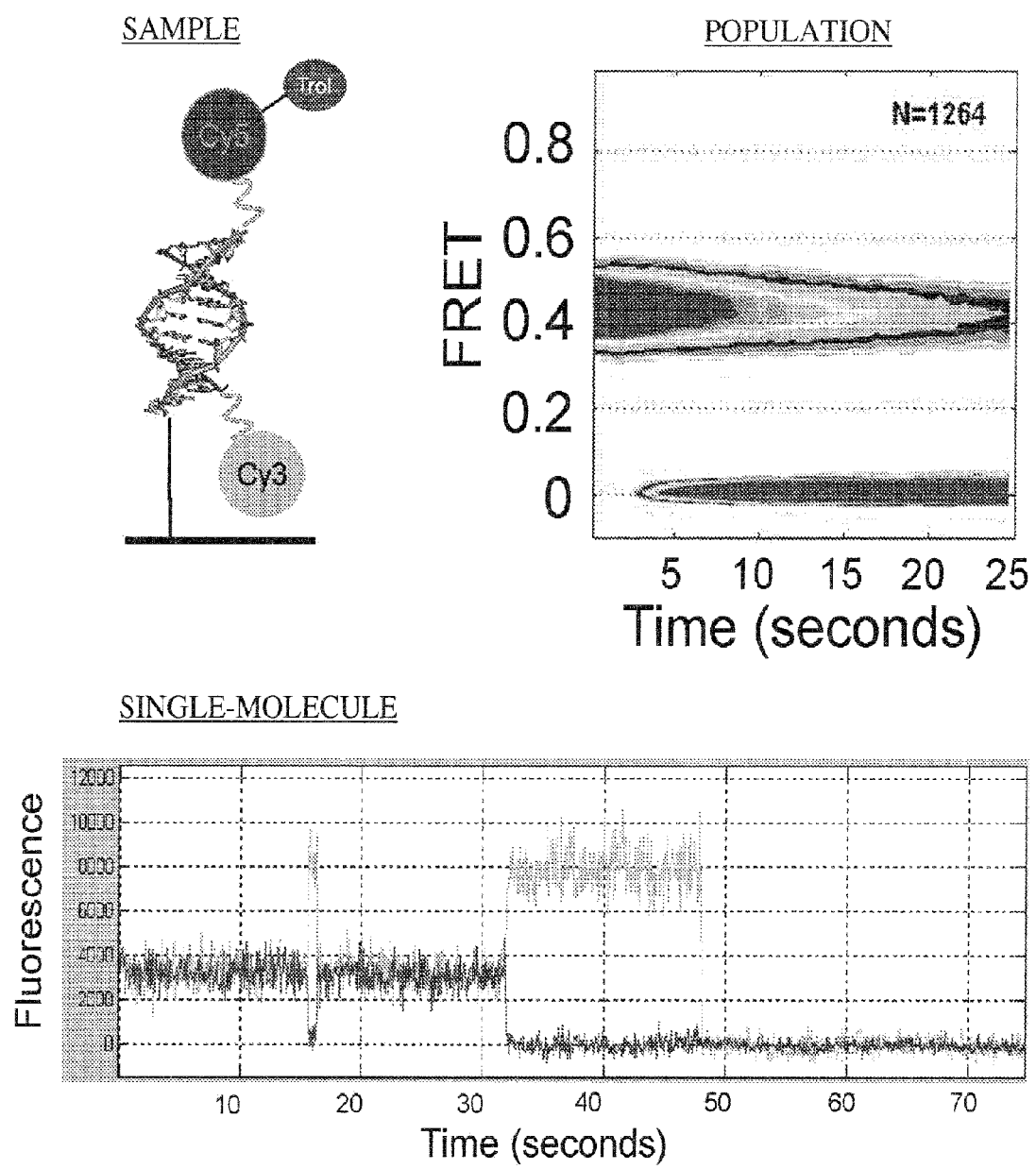
Figure 11D:
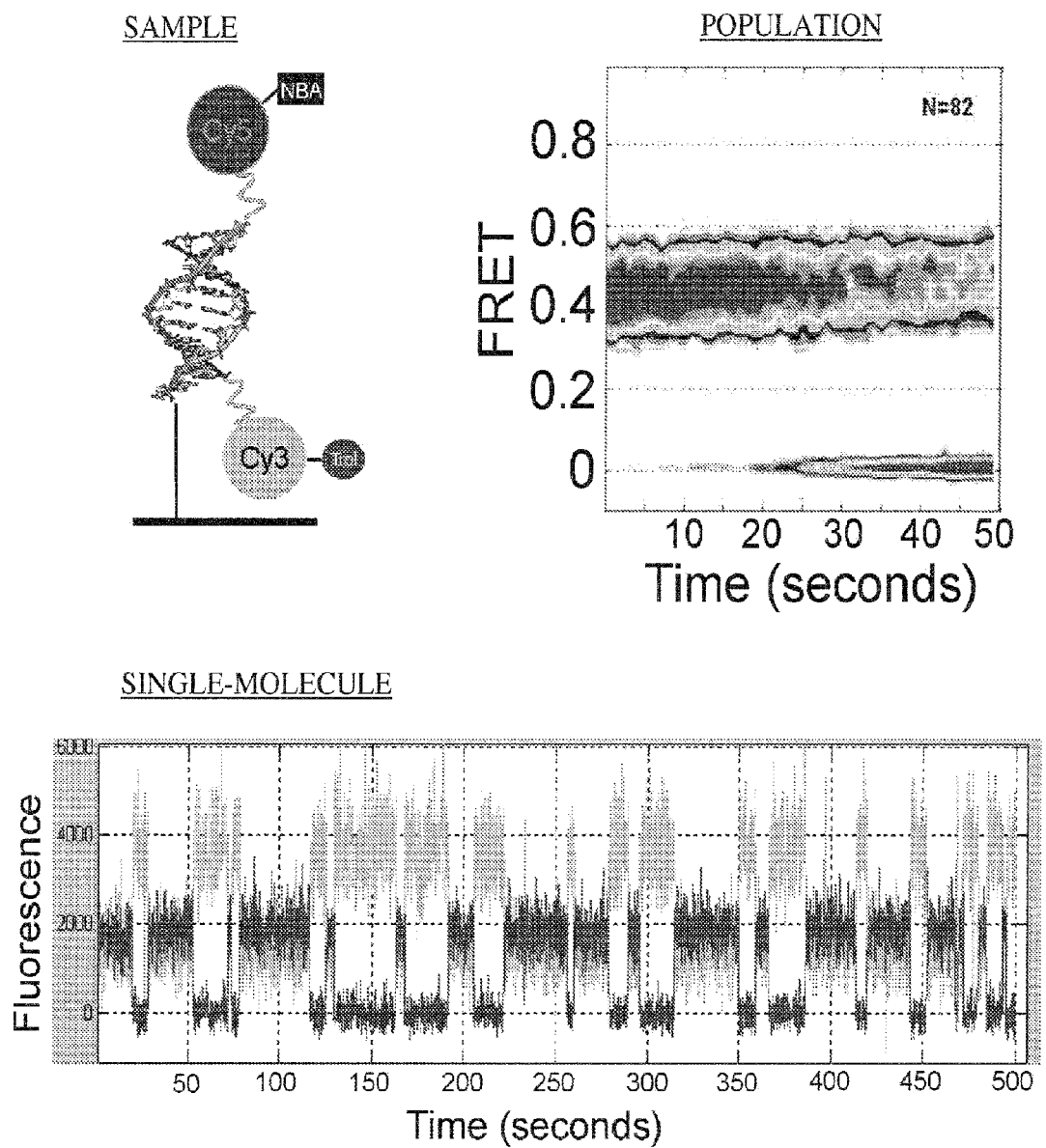

The fluorophore and protective agents may be linked together, either directly or via a linker, and the resulting fluorophore-protective agent composition attached to a molecule of interest, such as a biomolecule or biomolecule, or a surface of a bulk solid (e.g., FIGS. 9 and 10). Alternatively, the fluorophore and protective agents are not linked together, but separately attached to a biomolecule or surface of a bulk solid. The fluorophore-protective agent composition may also be attached to a molecule, such as a biomolecule or biomolecule, either directly or via a linker. In particular embodiments, the fluorophore-protective agent composition is attached to a molecule directly (i.e., without an intervening conjugating group) either via a fluorophore-molecule direct bond, a protective agent-molecule direct bond, or via an accessible atom of a linker that connects the fluorophore and protective agent. An advantage of the method described herein over conventional methods of the art is that, using the instant method, one can essentially take a commercially available bis-reactive dye and functionalize one end of it with a protective agent and then attach the other end to a biomolecule of interest. Another advantage of the method used herein is in the spatial uniformity that can be imparted between the fluorophore and molecule of interest. This is particularly advantageous in view of the great reliance on fluorophores for measuring various properties of a molecule (ex. distance between subunits by FRET). It is known that there is an inherent error introduced into such studies by having some kind of spacer (i.e., one of many variable lengths) in between the fluorophore and molecule of interest. However, in a preferred embodiment of the instant invention, one can significantly control for that error by consistently using the same spacer for each measurement. For example, in many commercial Cy-dyes, the spacer is typically a six-carbon chain terminating in a carboxylic acid. The molecule of interest is then attached to the fluorophore at the carboxylic acid. By leaving the linking length of the molecule essentially unchanged, any intrinsic error will also remain unchanged.

Figure 8A:
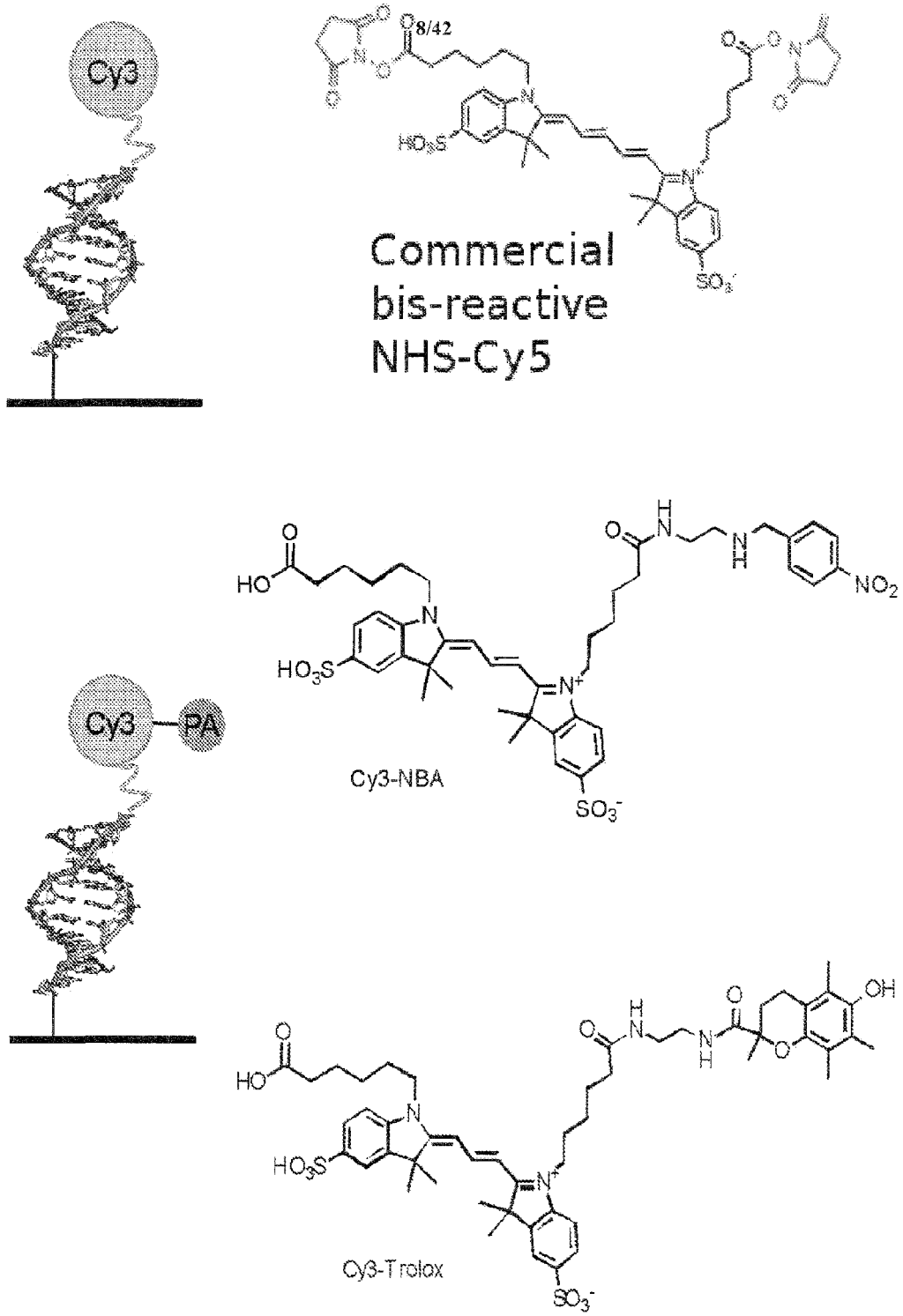
FIGS. 8A-8B. Experimental data showing two examples of linking a protective group to Cy3. Under direct excitation of Cy3, individual dwells in the fluorescent state were used to estimate time$_{on}$ ($t_{on}$), the lifetimes in the fluorescent state. This distribution was fit to an exponential decay process to demonstrate changes relative to Cy3 without a PA. Cy3 fluorescence ($t_{on}$) is only marginally affected by its direct linkage to NBA, while improved approximately 2.5-fold when directly linked to Trolox. Cy3- and Cy3-PA fluorescence behaviors were interrogated in the context of its linkage to DNA as schematized using the single-molecule TIR scheme show in FIG. 2. The specific dye molecules examined are shown. These data demonstrate that distinct protective agents operate either through distinct mechanisms or to different extents on the Cy3 fluorophore.
Figure 8B:
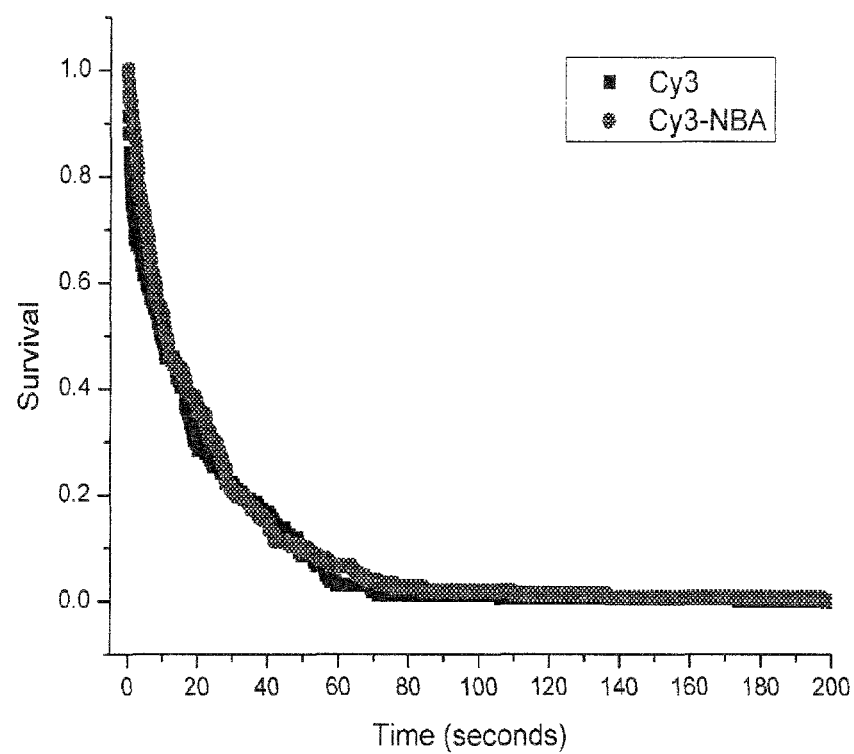
Figure 8B:
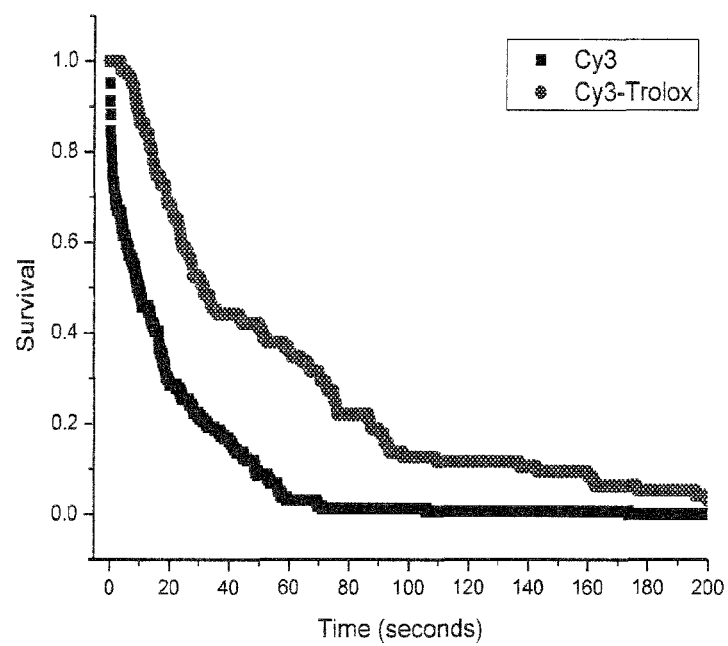

As used herein, a "surface" refers to the surface of a bulk solid material. The bulk solid material can be, for example, a particle (or bead) of an organic or inorganic polymeric composition. In one embodiment, the surface is inorganic, e.g., silica-based. In another embodiment, the surface is organic, e.g., polymer-based. In a particular embodiment, the fluorophore and/or protective agent and/or biomolecule is attached directly or via a linker to a surface using linking chemistry well known in the art (as schematized, for example, in FIGS. 2, 3, 4, 8, 9, 10, 11, 12, 13, 14, 15, and 17). In some embodiments, a fluorophore and protective agent are each attached to the surface proximally to each other. In other embodiments, a fluorophore-conjugated biomolecule and one, two, or more protective agents are each attached to a surface proximally to each other (FIGS. 13-16). In other embodiments, a protective agent-conjugated biomolecule and one, two, or more fluorophore molecules are each attached to a surface proximally to each other (FIGS. 13-16). In other embodiments, a biomolecule conjugated to one or more fluorophores and one or more protective agents is attached to a surface proximally to one or more fluorophores and/or protective agents and/or biomolecules conjugated to a fluorophore and/or protective agent. (FIG. 8, upper right and lower left panels). The particular embodiments shown in FIGS. 8 and 9 provide means of establishing proximity between the fluorescent species and the protective agent through non-covalent attachment strategies. Numerous other variations and strategies related to those shown in FIGS. 8 and 9 are possible.

The fluorophore compositions described herein can be used in any method or technology in which fluorophores are used. In a particular embodiment, the fluorophore compositions described herein are applied to fluorescence-based assay methods, such as PCR and ELISA assay methods. In more particular embodiments, the fluorophore compositions described herein are applied to FRET methods, and more particularly, smFRET methods. These methods are well known in the art. Particular reference is made to R. Dave, et al., *Biophysical Journal*, vol. 96, March 2009, pp. 2371-2381; Stryer L. Annu Rev. Biochem. Vol. 47 pg. 819-46 (1978); Forster T. (Ann Physik (1959); Roy R. Hohng S, Ha T. Nature Methods Vol. 5(6) pg. 507-516 (2008). Weiss S R Science Col. 283(5408) pg. 1676-83 (1999), all of which are incorporated herein in its entirety.

A significant advantage of the compositions described herein is that the position of one or more protective agents can be adjusted and fixed relative to one or more fluorophores. By this feature, one or more photophysical characteristics of the fluorophore can be suitably adjusted, optimized, or tuned to suit a particular application. Some photophysical characteristics include, for example, fluorescence lifetime, absorption and emission wavelength and extinction, stochastic blinking events, blinking frequency, and photobleaching characteristics. The characteristics being adjusted or optimized can be characteristics particularly relevant to non-assay applications, such as for photonic and photoswitching devices, including organic light emitting diodes (OLEDs). Significantly, the tunability feature of the instant fluorophore-protective agent compositions allows for altering (i.e., increasing or decreasing) the blinking rate of the fluorophore. For example, in certain applications, a faster blinking frequency is desired, while in other applications, a slower blinking frequency is desired, relative to the original blinking frequency (FIG. 11) (i.e., blinking frequency of the fluorophore when not in proximity to a protective agent). In other embodiments, the lifetimes of fluorescent and dark states can be tuned (as suggested by FIG. 1) by decreasing the effective rate of transition into or out of the triplet dark state.

In another embodiment, the invention is directed to applying any of the fluorophore compositions described above to methods for detecting a cellular process in a living cellular or multicellular organism. Such in vivo methods often include administering to the organism an effective amount of the fluorophore composition, and detecting the fluorophore in the organism. The organism being studied can be, for example, a mammal, a cell from a cell line (e.g., CHO cells or stem cells), a microbe (e.g., a bacterium or protozoan), or a mammalian or non-mammalian egg cell. Typically, the fluorophore composition to be administered possesses a portion (i.e., chemical group) that specifically and selectively targets a biological site or particular biomolecule in the mammal. Therefore, the fluorophore composition used in this manner functions as a targeting probe. These fluorophore compositions can also circumnavigate cell membrane permeability issues and the potential toxicity of protective agents in solution to a living cell. Furthermore, in some embodiments, the protective agent itself can function as a cell permeation enhancer. The specific application of this approach relates to the site-specific labeling of one or more target molecules in the cell by adding the fluorescent species to the cell medium or animal circulation. In both cases, crossing the cell membrane can be a limited aspect of the approach.

Examples have been set forth below for the purpose of illustration and to describe the best mode of the invention at the present time. However, the scope of this invention is not to be in any way limited by the examples set forth herein.

EXAMPLES

Experimental Materials and Methods

Preparation of Dye-Labeled/Protective Agent Linked Oligonucleotides

Figure 6:
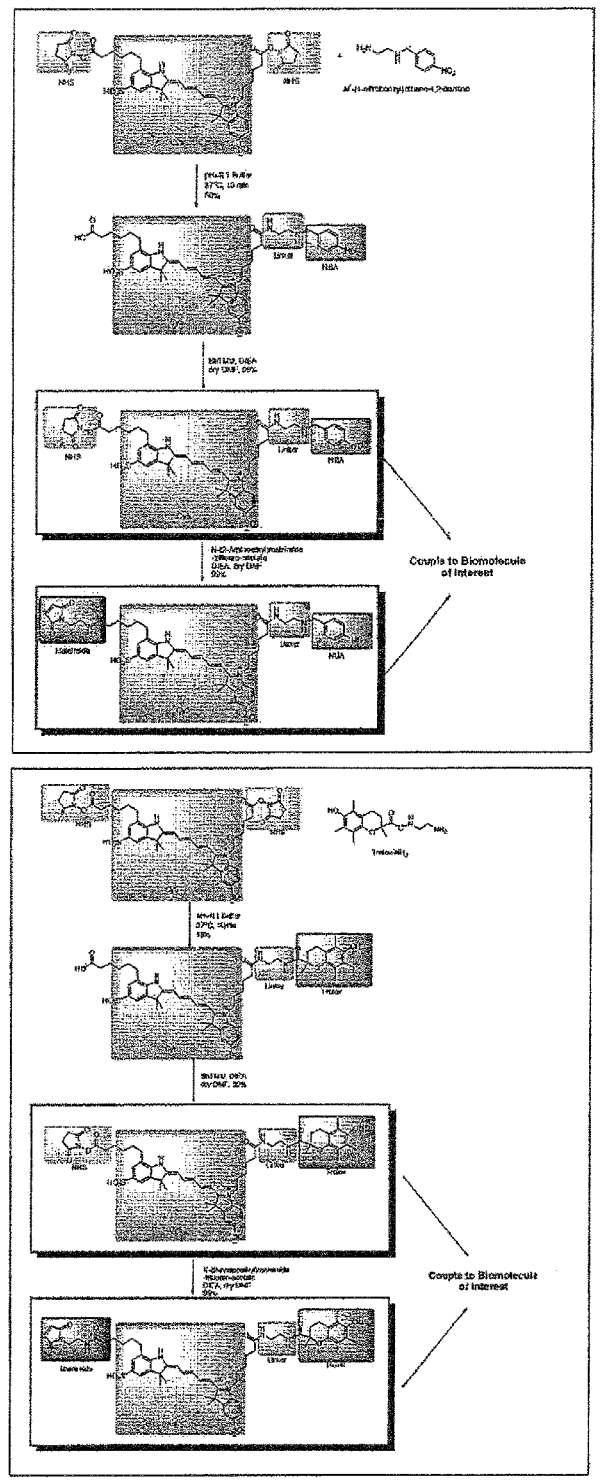
FIG. 6. Schemes for synthesizing Dye-Protective Agent conjugates from commercially available fluorophores. Here, after linking an amino modified protective agent (top panel NBA, bottom panel Trolox) to a bis-NHS functionalized dye (Cy5), a reactive group is regenerated (NHS or maleimide in this example) for downstream coupling to a biomolecule of interest.
Figure 7:
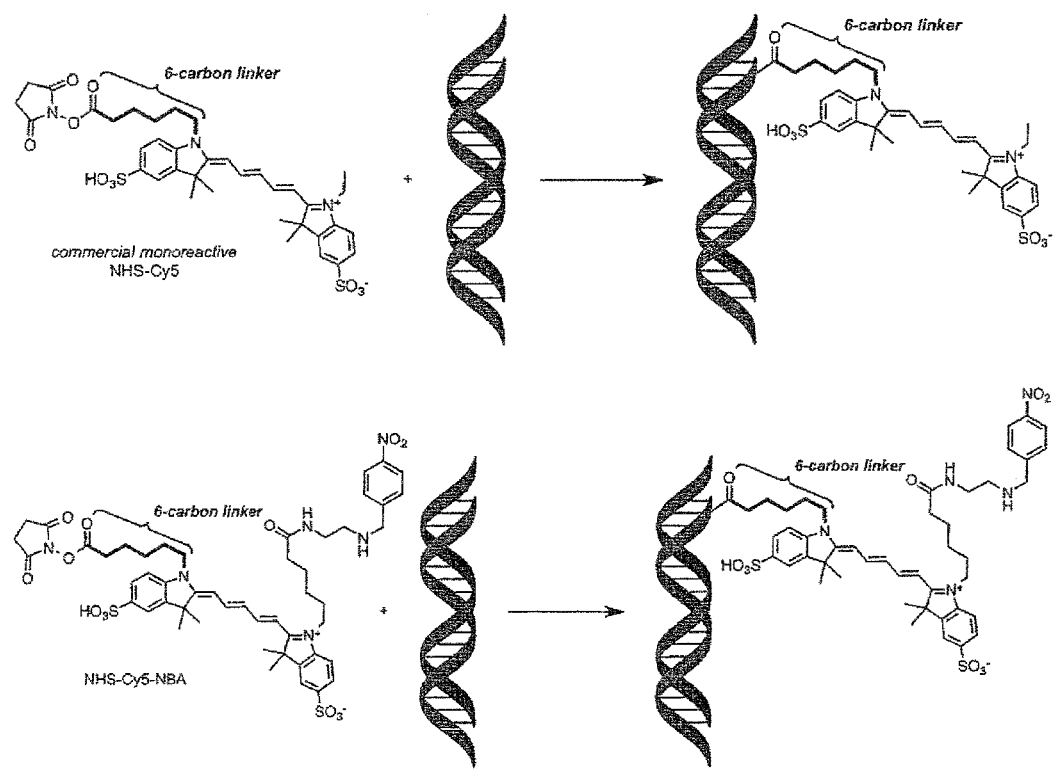
FIG. 7. Structures of exemplary fluorophores containing reactive coupling groups, and exemplary structures of fluorophore-protective agent (PA) compositions containing reactive coupling groups (NHS and maleimide groups for example) for coupling with another molecule. Commercial fluorophores are often sold with a standard linker that places the fluorophore at a set distance from the molecule to which it is attached. Fluorophore-PA molecules synthesized from commercially available agents are designed with the same linker in place, thus maintaining the same specific distance from the molecule to which it is attached. Using synthetic strategies, the length of this linker can be tailored according to experimental demand for either greater or less mobility. Drawings provide a description of how new protective agent-containing dyes can be attached to biomolecules in a manner consistent with currently marketed dyes. Such dyes might be adventitious because they retain the same distance between dye and biomolecule and therefore allow for historical distance measurements to remain accurate.

Cy3, 5 or 5.5 Bis NHS-Ester was first reacted with an equimolar amount of amine modified protective agent in 50 mM potassium borate pH8 for 10 minutes at 37 degrees. After quenching with 2 fold excess of potassium hydroxide, monoreacted dye was purified from unreacted and di-reacted dyes using a semipreparative HPLC C18 column in 10 mM triethylammonium acetate in a gradient from 25-100% acetonitrile. After evaporation of acetonitrile, the product was concentrated and buffer exchanged over a sep-pak C18 column and eluted in methanol before final lyophilization. Reactive functional groups are regenerated as shown in FIG. 6.

Two complimentary 12 or 21-nucleotide DNAs were chemically synthesized with one strand possessing a 5'-$C_6$-amino linker for dye linkage along with an additional 3'-biotin moiety attached via a 22 atom spacer (5'-/5AmMC6/GTC ATG GTC ATG/3BioTEG/-3' or 5'-/5AmM C6/CAT GAC CAT GAC CAT GAC CAG/3BioTEG/-3' IDT, Coralville, Iowa) and the complimentary strand being either 5'-/5AmM C6/CAT GAC CAT GAC-3' or 5'-CTG GTC ATG GTC ATG GTC ATG-3' with a $C_6$-amino linker incorporated at select positions within the sequence. Each DNA strand was individually labeled with either a commercially-available, N-hydroxysuccinimide (NHS) ester activated dye molecule Cy3, Cy5 or Cy5.5; GE Healthcare, Piscataway, N.J.), newly generated protective agent-linked compounds, or NHS modified protective agents through the following procedure:

Lyophilized DNAs were resuspended in distilled, deionized water and adjusted to 50 uM in 50 mM potassium borate buffer, pH 8.1, 200 mM KCl. Labeling was achieved by adding a 10-fold molar excess of NHS-reactive dye or NHS modified protective agents resuspended in Dimethyl sulfoxide (DMSO) in a 10 ul reaction at 37° C. for 10 minutes. All labeling reactions were quenched with 0.2 ul of 1M Tris pH 7.5 at 25° C. for 2 minutes. Labeled strands were hybridized by mixing the 2 in equimolar ratios, briefly heating to 75° C. for 12-mers and 95° C. for 21-mers followed by passive cooling to room temperature. Unbound dye was removed using 200 ul DEAE sepharose resin equilibrated with 10 mM Tris Acetate pH 7.5, 200 mM ammonium chloride. Hybrids were diluted in column buffer for binding, then after extensive washing to liberate free dye, the DNA was eluted with 10 mM Tris Acetate pH 7.5, 1M ammonium chloride. Labeled fractions were pooled by visualization using a Kodak Gel Logic 440 imaging station (~200 ul total), diluted to 1 ml with Buffer A (1.7M Ammonium Sulfate, 10 mM Ammonium Acetate pH 5.85) and applied over an FPLC phenyl 5PW column (Tosoh Bioscience) using a 60 min gradient from buffer A to B (10% Methanol, 10 mM Ammonium Acetate pH 5.85). The peak of interest was collected and diluted as needed for single-molecule imaging experiments.

Single-Molecule Imaging and Experimental Conditions

All experiments were performed using a laboratory built, prism-based TIRF apparatus as previously described at specified illumination intensities in Tris-polymix buffer (50 mM Tris-OAc pH 7.5, 100 mM KCl, 5 mM $NH_4OAc$, 0.5 mM $Ca(OAc)_2$, 15 mM $Mg(OAc)_2$, 0.1 mM EDTA, 50 mM β-Mercaptoethanol, 5 mM putrescine, and 1 mM spermidine) containing 2 unit/μl Glucose Oxidase (Sigma-Aldrich, St. Louis, Mo.), 20 units/μl catalase (Sigma-Aldrich, St. Louis, Mo.) and 0.1% v/v glucose unless stated otherwise (Munro J B Altman R B, O'Connor N, Blanchard S C, Mol. Cell Vol. 25 pg. 505-517 (2007). Biotinylated DNA molecules were immobilized via a biotin-streptavidin interaction within microfluidic channels constructed on quartz slides (Blanchard S C, Kim H D, Gonzalez R L, Puglisi J D, Chu S PNAS Vol. 101(35) pg. 12893-8 (2004). Fluorescence from surface-immobilized molecules, illuminated via the evanescent wave generated by total internal reflection of 532 nm (Laser Quantum, Cheshire, U.K.) and/or 635 nm (Coherent, Auburn, Calif.) laser sources, was collected using a 1.2 NA 60× water-immersion objective (Nikon, Melville, N.Y.) and imaged onto a Cascade 128B CCD (Roper Scientific, Tucson, Ariz.). Data were acquired using Metamorph software (Universal Imaging Corporation, Downingtown, Pa.) collecting at a frame rate of 25/sec (40 millisecond time resolution). For direct 635 nm illumination experiments, data were collected at a frame rate of 10/sec (100 millisecond time resolution).

Kinetic Analysis of smFRET Time Traces

The photophysical properties of dyes were investigated by extracting single-molecule time traces from the acquired CCD images using in-house designed software in Matlab (Natick, Mass.) as previously described Munro J B Altman R B, O'Connor N, Blanchard S C, Mol. Cell. Vol. 25 pg. 505-517 (2007). FRET efficiencies ($E_{FRET}$) for each trace were calculated according to the equation:

$$E_{FRET} = \frac{I_{acceptor}}{I_{donor} + I_{acceptor}};$$

where $I_{acceptor}$ and $I_{donor}$ correspond to Cy5 and Cy3 fluorescence intensity, respectively, after correcting for background intensity and cross talk between the donor and acceptor fluorescence signals. In the analysis of smFRET data, only those molecules yielding both donor and acceptor fluorescence were considered for analysis. In fluorescence and FRET imaging experiments, molecules yielding a signal-to-noise (S/N) ratio less than 6:1 were excluded from analysis. Unless otherwise stated, S/N is defined as the total fluorescence intensity (donor+acceptor)/standard deviation of background fluorescence after photobleaching. The kinetic parameters of blinking and photobleaching were extracted from smFRET trajectories by idealizing fluorescence and FRET data to specific kinetic models using a segmental k-means algorithm implemented in QuB as previously reported (Munro J B Altman R B, O'Connor N, Blanchard S C, Mol. Cell. Vol. 25 pg. 505-517 (2007); Dave, R et al., *Biophysical Journal*, vol. 96, March 2009, pp. 2371-2381 Single-molecule data obtained from individual DNA molecules were fit to a two-state kinetic model yielding a series of dwells in the non-zero and zero-fluorescence/FRET states. Because under all smFRET conditions tested the vast majority (>85%) of FRET trajectories were limited by acceptor photobleaching, only dwells prior to the last acceptor fluorophore dark state were examined. For direct and FRET-based illumination experiments, individual dwells in non-zero and zero fluorescent/FRET states were used to estimate $t_{on}$, the lifetime of the fluorescence state. From these parameters, the lifetimes that each single-molecule was observed in the fluorescent state was estimated by fitting each distribution to exponential decay processes using the Origin software package.

FIG. 8 presents experimental data showing two examples of linking a protective group to Cy3. Under direct excitation of Cy3, individual dwells in the fluorescent state were used to estimate time$_{on}$ ($t_{on}$), the lifetimes in the fluorescent state. This distribution was fit to an exponential decay process to demonstrate changes relative to Cy3 without a PA. Cy3 fluorescence ($t_{on}$) is only marginally affected by its direct linkage to NBA, while improved approximately 2.5-fold when directly linked to Trolox. Cy3- and Cy3-PA fluorescence behaviors were interrogated in the context of its linkage to DNA as schematized using the single-molecule TIR scheme show in FIG. 2. The specific dye molecules examined are shown. These data demonstrate that distinct protective agents operate either through distinct mechanisms or to different extents on the Cy3 fluorophore.

FIG. 9 presents experimental data taken as described in FIG. 8 showing the lifetime of Cy5 fluorescence ($t_{on}$) is greatly improved (>10-fold) by its direct linkage to either NBA or Trolox. Cy5- and Cy5-PA fluorescence behaviors were interrogated in the context of its linkage to DNA as schematized using the single-molecule TIR scheme shown in FIG. 2. The specific dye molecules examined are shown. These data demonstrate that the same protective agents examined for the Cy3 fluorophore operate either through distinct mechanisms or to different extents on the Cy5 fluorophore.

FIG. 10 presents experimental data taken as described in FIG. 8 showing the lifetime of Cy5.5 fluorescence ($t_{on}$) is greatly improved (>20-fold) by its direct linkage to either NBA or Trolox. Cy5.5 and Cy5.5-PA fluorescence behaviors were interrogated in the context of its linkage to DNA as schematized using the single-molecule TIR scheme shown in FIG. 2. The specific dye molecules examined are shown. In yet another example that distinct protective agents operate either through distinct mechanisms or to different extents on fluorophore species, Trolox and NBA are shown to improve the photophysical properties of the Cy5.5 fluorophore more substantially than both Cy3 and Cy5.

FIG. 11 presents experimental data demonstrating improvements in the informative FRET lifetime for the Cy3 and Cy5 pair. (Left panels) specific samples interrogated in which no protective agent is present, NBA is linked to Cy5, Trolox is linked Cy5 or a sample where distinct protective agents are linked to each fluorophore: NBA is linked to Cy5 and Trolox is linked Cy3. (Middle panels) Experimental single-molecule FRET data showing examples of Cy3 and Cy5 fluorescence. Experimental data showing the population FRET behaviors observed where each of the constructs containing fluorophore-PA conjugates has an extended FRET duration. In the sample where each fluorophore of the FRET pair is linked to a protective agent (bottom panels), the total lifetime of FRET is greatly improved over samples containing no protective agents (>20-fold) and significantly improved over samples where only the Cy5-fluorophore is linked to a protective agent (>2-fold) (note the time axes on the bottom panels represent a much longer imaging period than the others shown). By increasing the FRET duration and minimizing dark states, the information content of the experiment is substantially improved. By extending the FRET duration, more robust structural information can be obtained (as required for "Molecular EKG" imaging (Blanchard S C Curr Opin Struct. Biol Vol. 19(1) pg. 103-9 (2009)) and/or greater confidence in the localization of single-fluorophores when tracking blinking kinetics (as for super-resolution imaging).

Figure 12A:
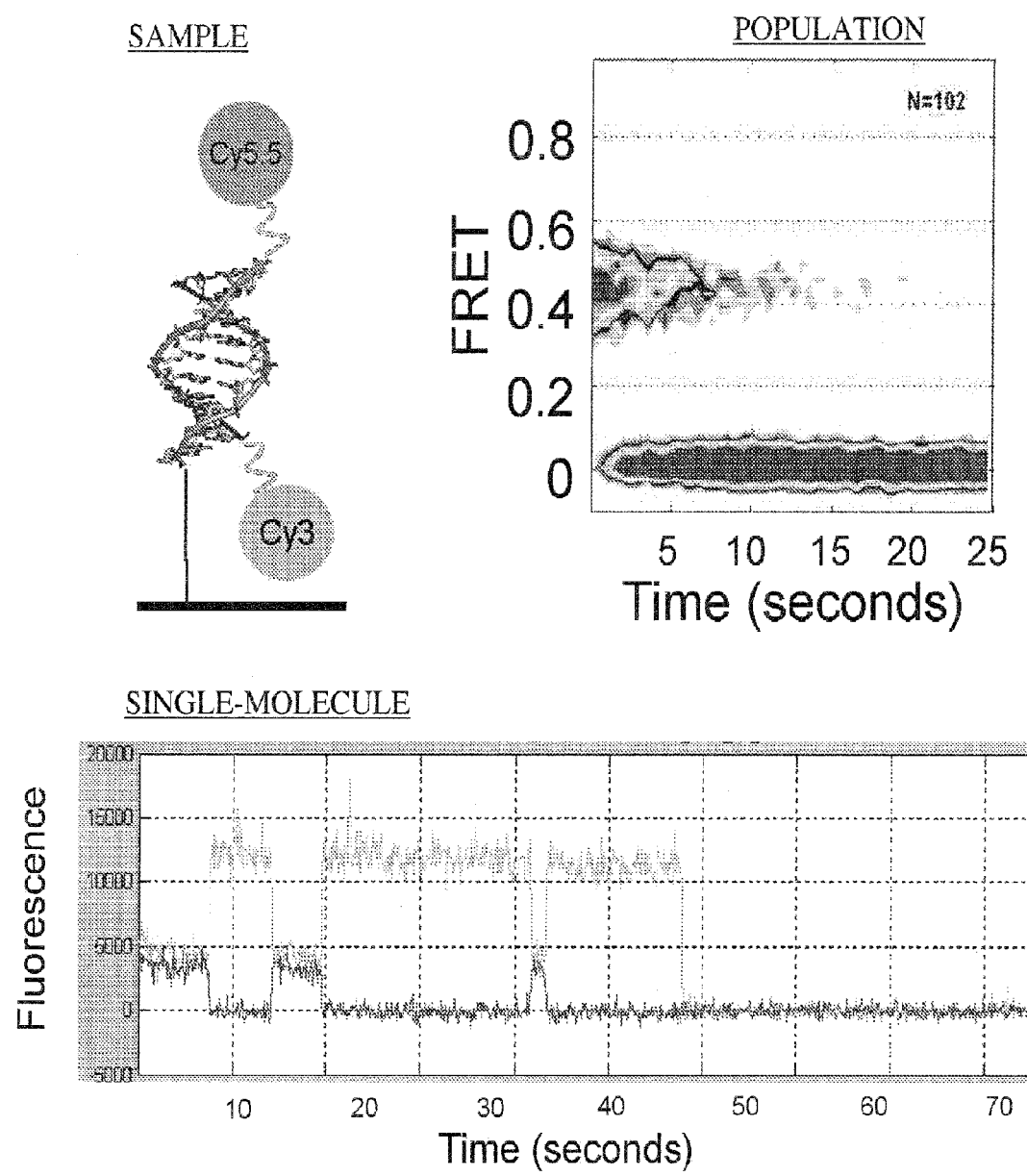
FIGS. 12A-12C. Experimental data demonstrating another example of the improvement in FRET lifetimes between a different FRET pair. In this case Cy3 and Cy5.5 are interrogated as described in FIG. 11. Population histograms (right panels) reveal an increase in the lifetime of fretting molecules when either of two protective agents are linked to the Cy5.5 acceptor dye. Significantly, these data demonstrate another example showing that protective agents linked to the acceptor fluorophore, Cy5.5 greatly extend the total period of FRET observation compared to the case when no protective agents are present (>5-fold).
Figure 12B:
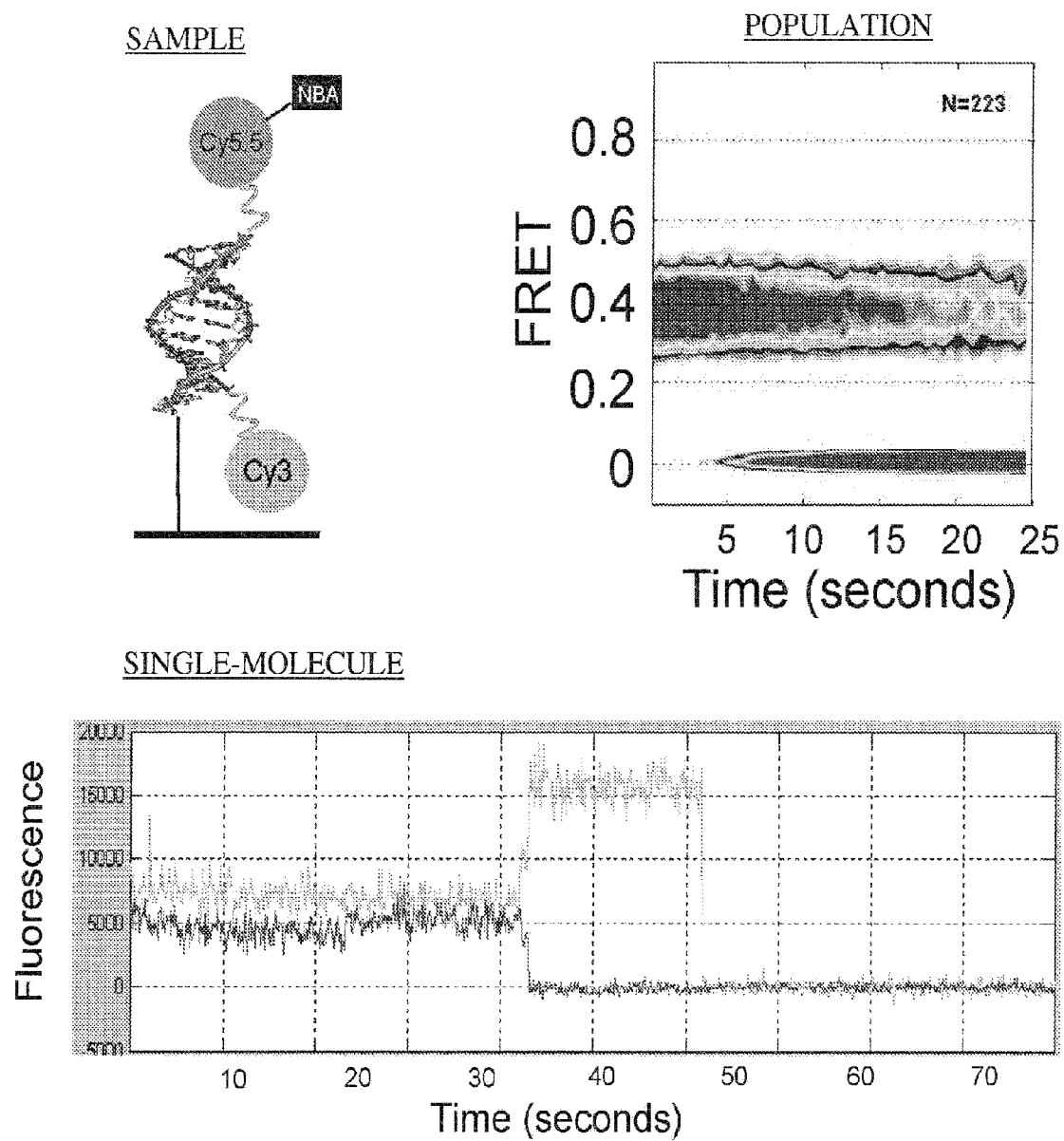
Figure 12C:
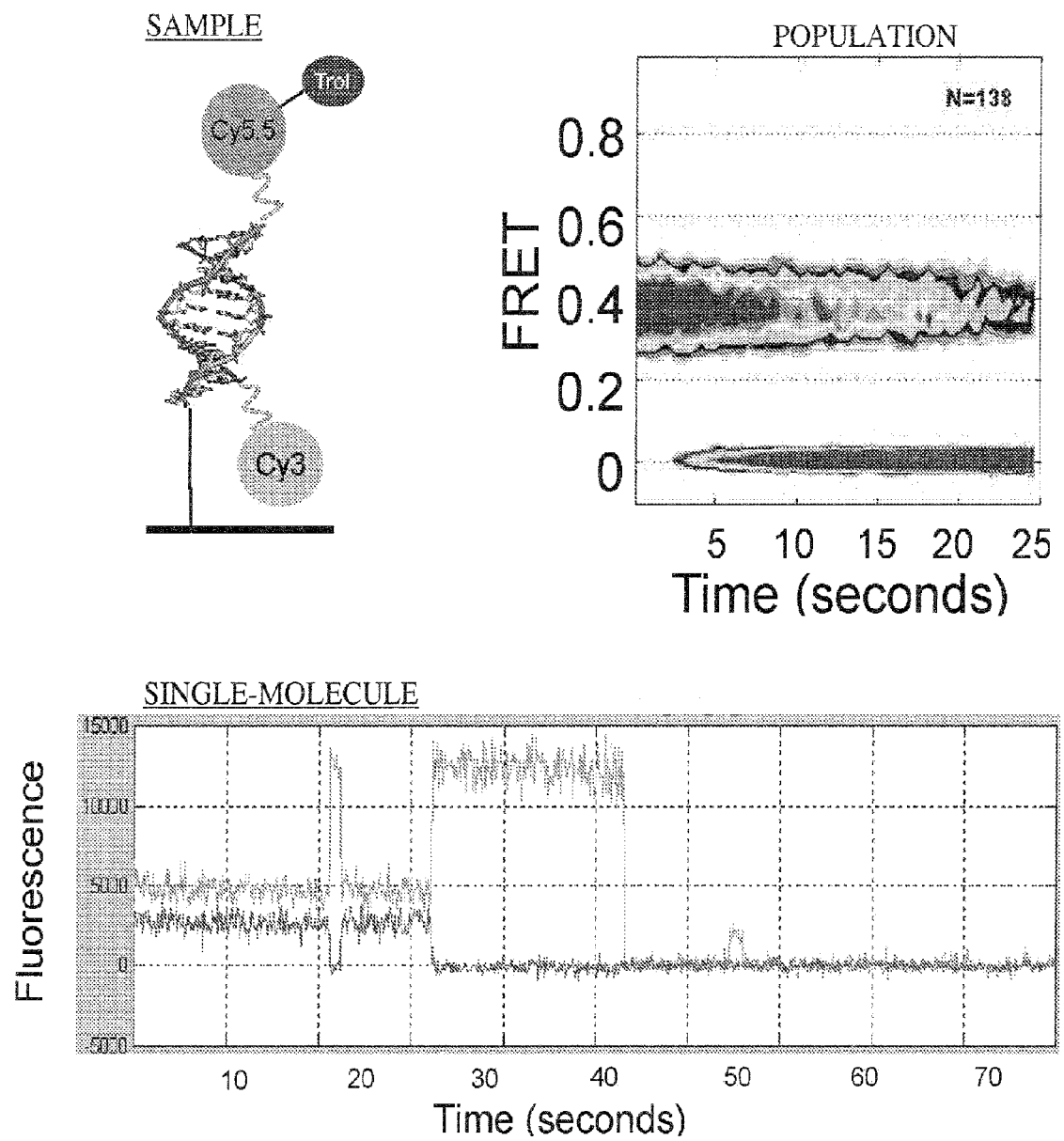

FIG. 12 presents experimental data demonstrating another example of the improvement in FRET lifetimes between a different FRET pair. In this case Cy3 and Cy5.5 are interrogated as described in FIG. 11. Population histograms (right panels) reveal an increase in the lifetime of fretting molecules when either of two protective agents are linked to the Cy5.5 acceptor dye. Significantly, these data demonstrate another example showing that protective agents linked to the acceptor fluorophore, Cy5.5 greatly extend the total period of FRET observation compared to the case when no protective agents are present (>5-fold).

Figure 13A:
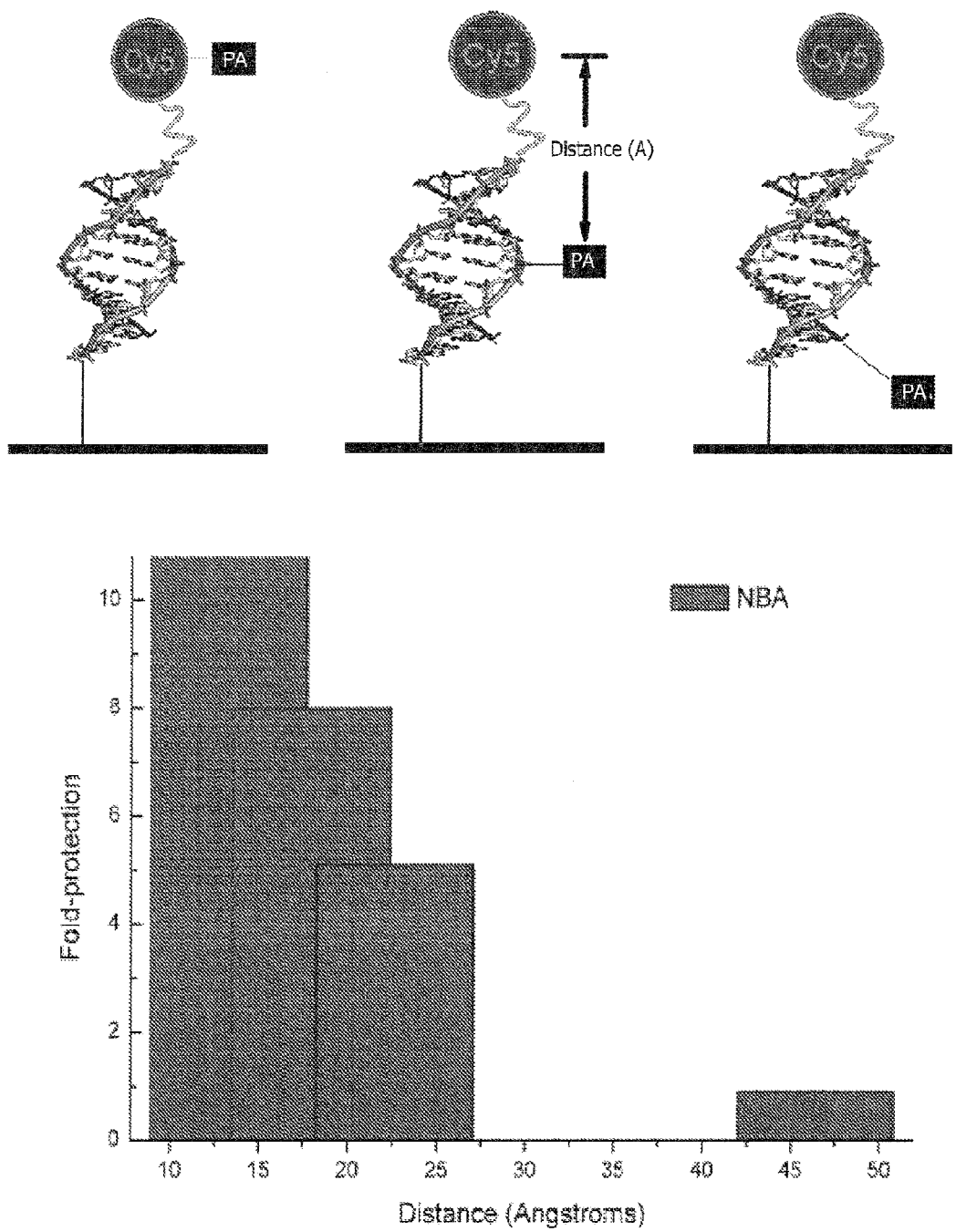
FIGS. 13A-13B. Experimental data showing the distance dependence of protective agent affects on fluorophore performance using Cy5-labeled DNA as a specific example. Protective agents NBA (left panel) or Trolox (right panel) were linked to 21-mer DNA oligonucleotides either directly through an NHS activating group on Cy5, or proximal to the fluorophore through a modified amine at the C6 position of internally designated bases. Under direct excitation of Cy5, individual dwells in the fluorescent state were used to estimate $t_{on}$, the lifetimes in the fluorescent state. This distribution was fit to a double exponential decay process and the time constants were divided by that of a no-PA control to obtain the fold protection for each individual distance. These data demonstrate that the PA need not be directly attached to the fluorophore species in order to mediate control over the fluorophore photophysics.
Figure 13B:
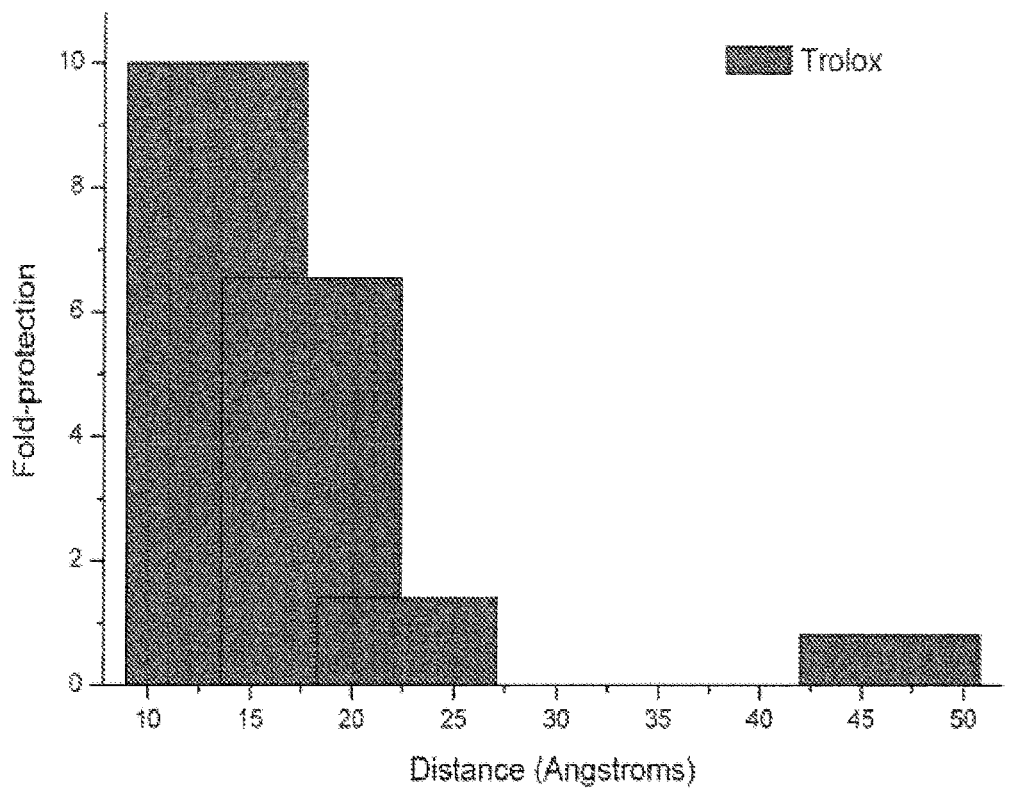

FIG. 13 presents experimental data showing the distance dependence of protective agent affects on fluorophore performance using Cy5-labeled DNA as a specific example. Protective agents NBA (left panel) or Trolox (right panel) were linked to 21-mer DNA oligonucleotides either directly through an NHS activating group on Cy5, or proximal to the fluorophore through a modified amine at the C6 position of internally designated bases. Under direct excitation of Cy5, individual dwells in the fluorescent state were used to estimate $t_{on}$, the lifetimes in the fluorescent state. This distribution was fit to a double exponential decay process and the time constants were divided by that of a no-PA control to obtain the fold protection for each individual distance. These data demonstrate that the PA need not be directly attached to the fluorophore species in order to mediate control over the fluorophore photophysics.

In particular, FIG. 13 includes drawings and charts depicting how proximity of the protective agent to the fluorophore mediates protection in a distance-dependent fashion. Exemplary proximity relationships for Cy5-NBA and Cy5-Trolox are shown, where either protective agent was moved away from the fluorophore by linking it through a DNA oligonucleotide spacer. Triplet state quenchers NBA (left panel) or Trolox (right panel) were linked to 21-mer DNA oligonucleotides either directly through an NHS activating group on Cy5, or proximal to the fluorophore through a modified amine at the C6 position of internally designated bases. Under direct excitation of Cy5, individual dwells in the fluorescent state were used to estimate "time on" (i.e., $t_{on}$), the lifetime in the fluorescent state. This distribution was fit to a double exponential decay process and the time constants were divided by that of a no-TSQ control to obtain the fold protection for each individual distance.

Figure 14:
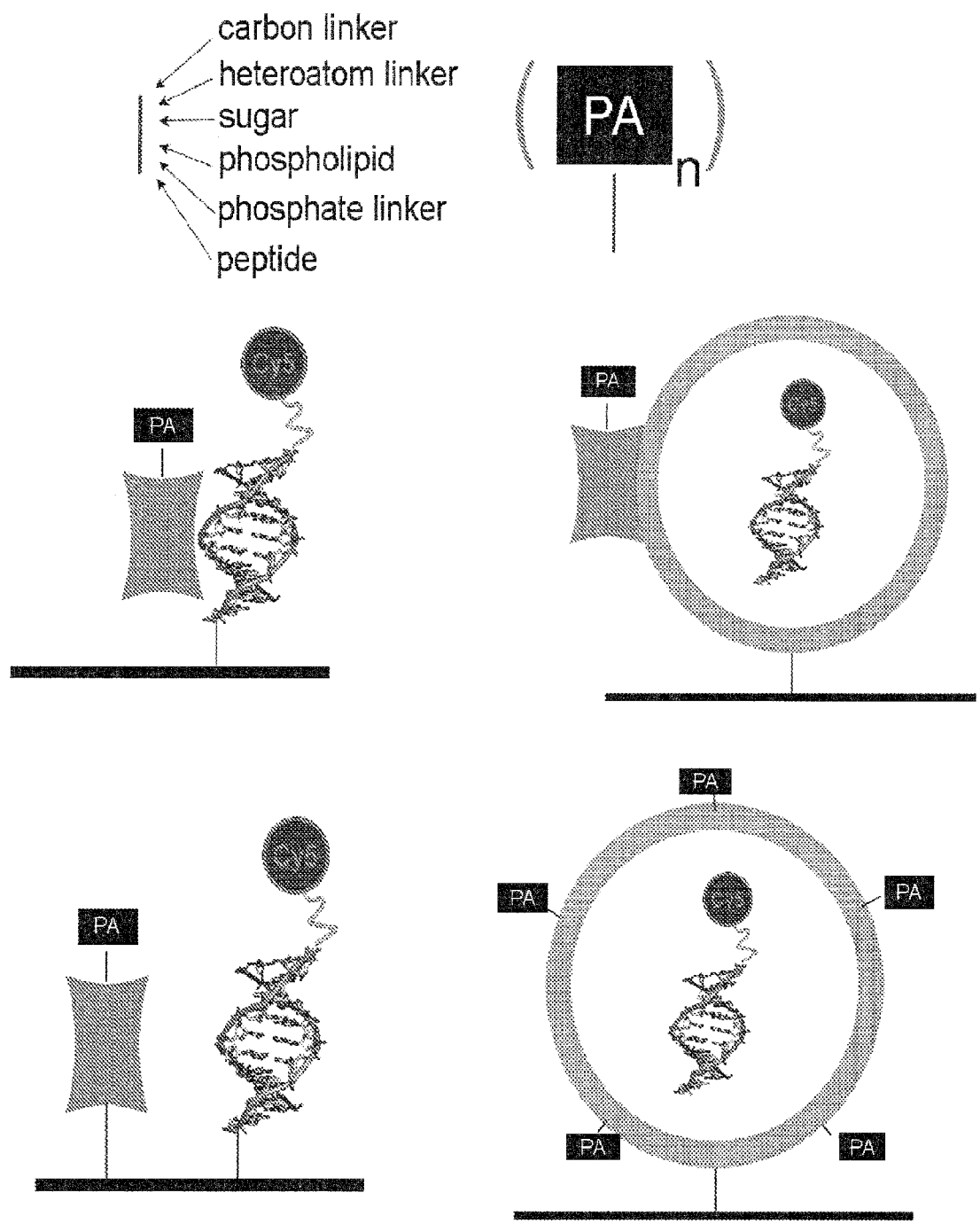
FIG. 14. Drawings depicting some exemplary specific, non-covalent geometries and means for establishing close proximity between fluorescent molecules and one or more protective agents using Cy5-labeled DNA as a specific example (Upper left panel) proximity of one or more protective agents to a fluorescing species by its attachment to a nearby secondary molecule or chemical post (purple block). (Upper right panel) proximity of one or more protective agents to a fluorescing species by its attachment to a secondary molecule that non-covalently associates with a lipid structure encapsulating the fluorescing species. (Lower left panel) proximity of one or more protective agents to a fluorescing species by its attachment to a secondary molecule that non-covalently associates with the fluorescing species. (Lower right panel) proximity of one or more protective agents to a membrane-encapsulated fluorescing species achieved through their attachment to, or embedding within, the inner or outer leaflet of a lipid vesicle, liposome or nanosome.

FIG. 14 presents drawings depicting some exemplary specific, non-covalent geometries and means for establishing close proximity between fluorescent molecules and one or more protective agents using Cy5-labeled DNA as a specific example (Upper left panel) proximity of one or more protective agents to a fluorescing species by its attachment to a nearby secondary molecule or chemical post (purple block). (Upper right panel) proximity of one or more protective agents to a fluorescing species by its attachment to a secondary molecule that non-covalently associates with a lipid structure encapsulating the fluorescing species. (Lower left panel)

proximity of one or more protective agents to a fluorescing species by its attachment to a secondary molecule that non-covalently associates with the fluorescing species. (Lower right panel) proximity of one or more protective agents to a membrane-encapsulated fluorescing species achieved through their attachment to, or embedding within, the inner or outer leaflet of a lipid vesicle, liposome or nanosome.

Figure 15:
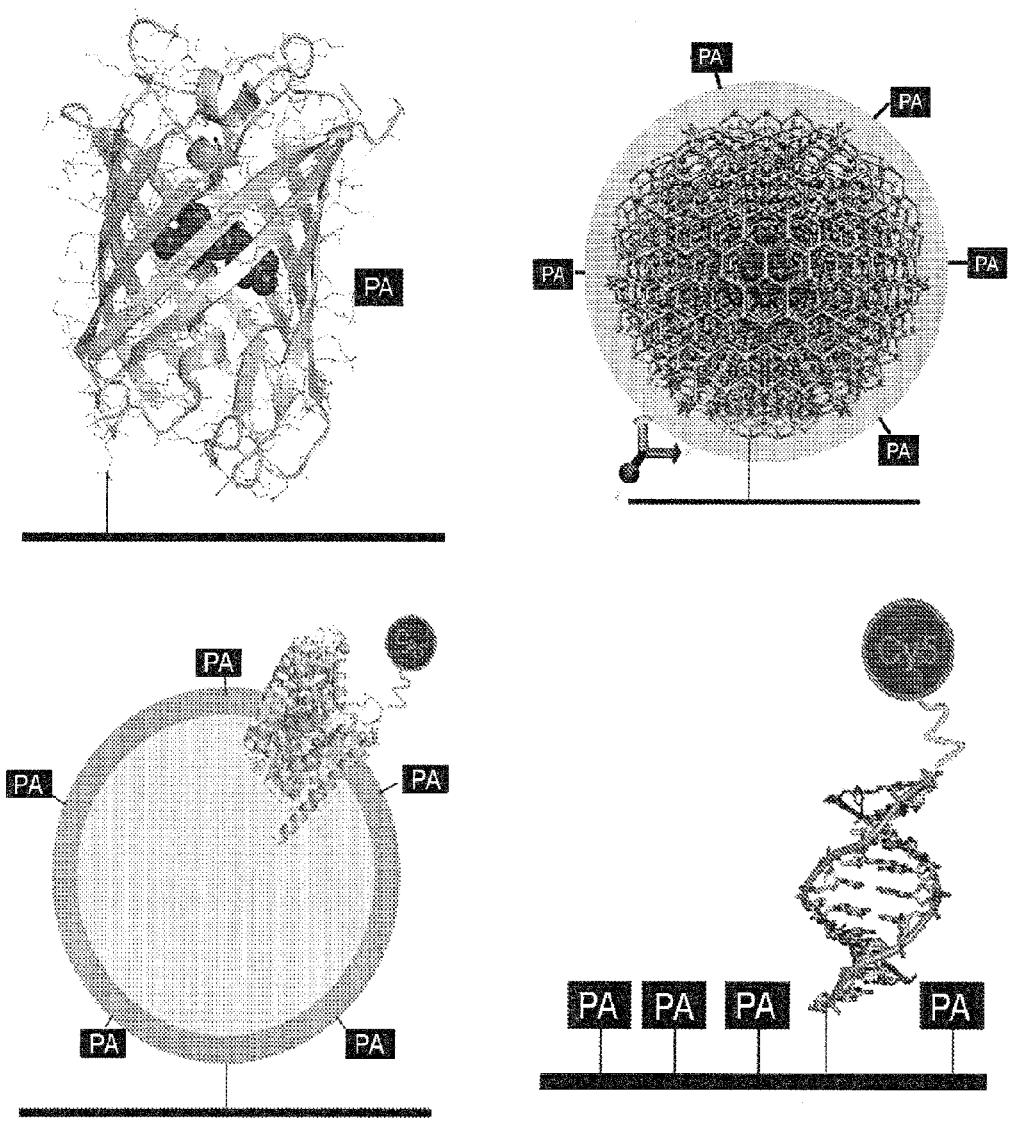
FIG. 15. Drawings depicting some exemplary strategies for achieving proximity of one or more protective agents to a fluorescing species (Upper left panel) protective agents either chemically linked to natural amino acid side chains located on the surface of a fluorescent protein or by way of non-natural amino acid incorporation at the level of protein synthesis. (Upper right panel) one or more protective agents linked to the outer shell layer(s) of a quantum dot by way of impregnation or covalent attachment. (Lower left panel) proximity of one or more protective agents to a membrane-bound fluorescing species achieved through the attachment to, or embedded within, the inner or outer leaflet of a lipid vesicle, liposome or nanosome. (Lower right panel) proximity of one or more protective agents to a fluorescence species via embedding or impregnating the solid support to which the fluorescent species is located proximally.

FIG. 15 presents drawings depicting some exemplary strategies for achieving proximity of one or more protective agents to a fluorescing species (Upper left panel) protective agents either chemically linked to natural amino acid side chains located on the surface of a fluorescent protein or by way of non-natural amino acid incorporation at the level of protein synthesis. (Upper right panel) one or more protective agents linked to the outer shell layer(s) of a quantum dot by way of impregnation or covalent attachment. (Lower left panel) proximity of one or more protective agents to a membrane-bound fluorescing species achieved through the attachment to, or embedded within, the inner or outer leaflet of a lipid vesicle, liposome or nanosome. (Lower right panel) proximity of one or more protective agents to a fluorescence species via embedding or impregnating the solid support to which the fluorescent species is located proximally.

Figure 16:
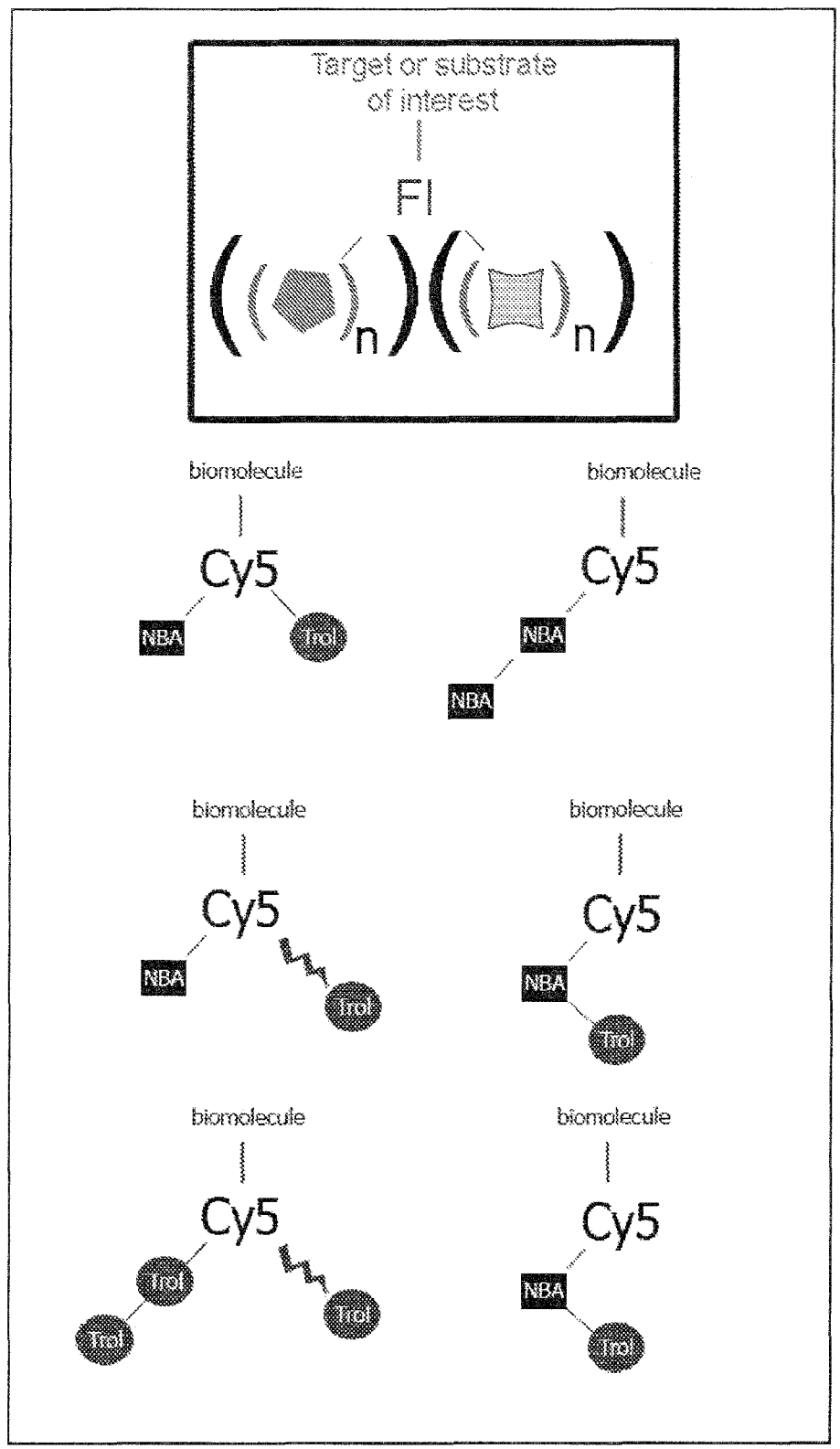
FIG. 16. Drawings depicting some exemplary strategies for achieving proximity of more than one protective agent to a fluorescing species that is attached to a target or substrate of interest as well as specific examples of Cy5-PA linkages.

FIG. 16 presents drawings depicting some exemplary strategies for achieving proximity of more than one protective agent to a fluorescing species that is attached to a target or substrate of interest as well as specific examples of Cy5-PA linkages.

Figure 17A:
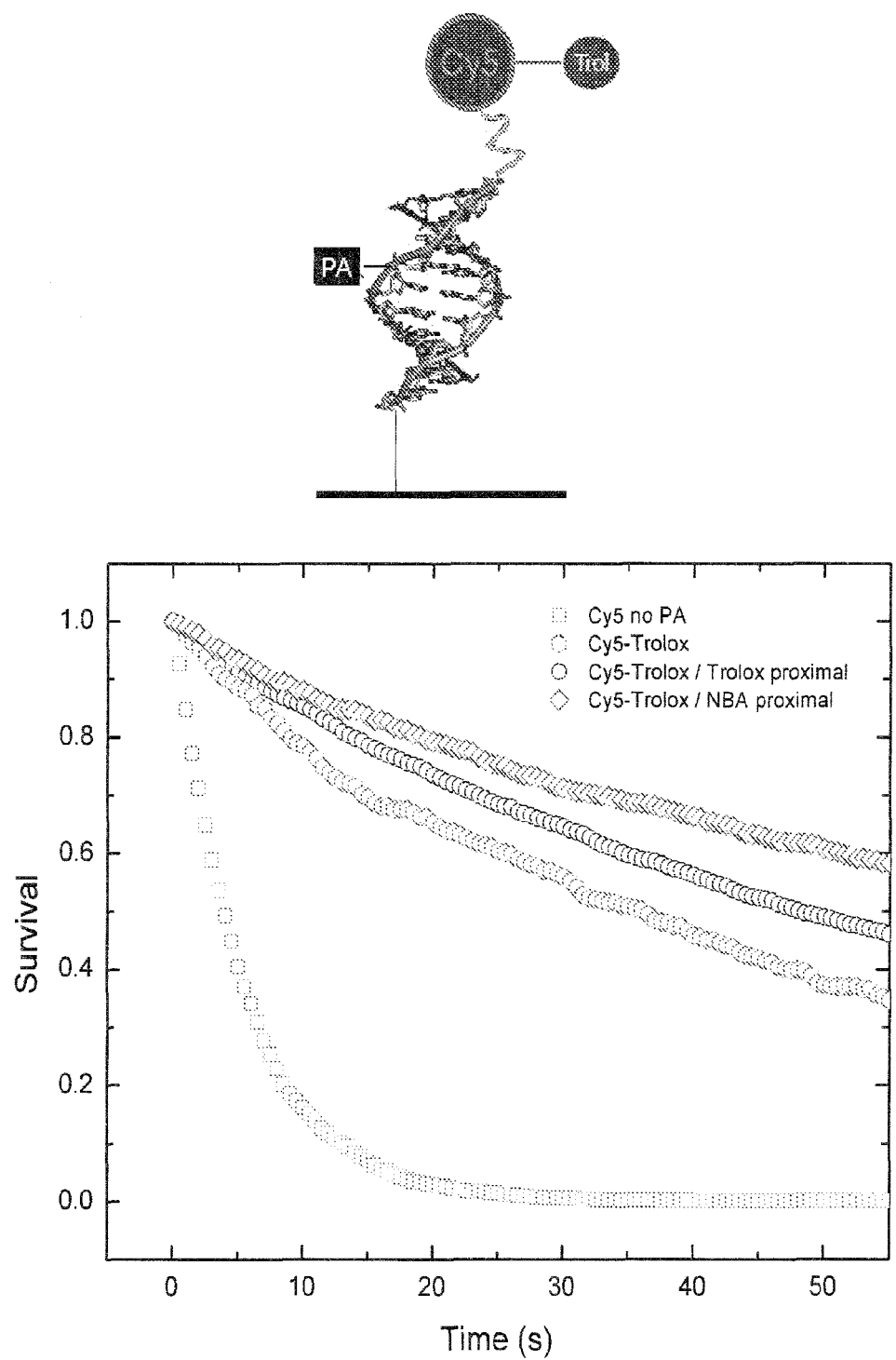
FIGS. 17A-17B. Experimental data demonstrating the utility of achieving proximity of more than one protective agent to a fluorescing species using Cy5-labeled DNA as an example.
Figure 17B:
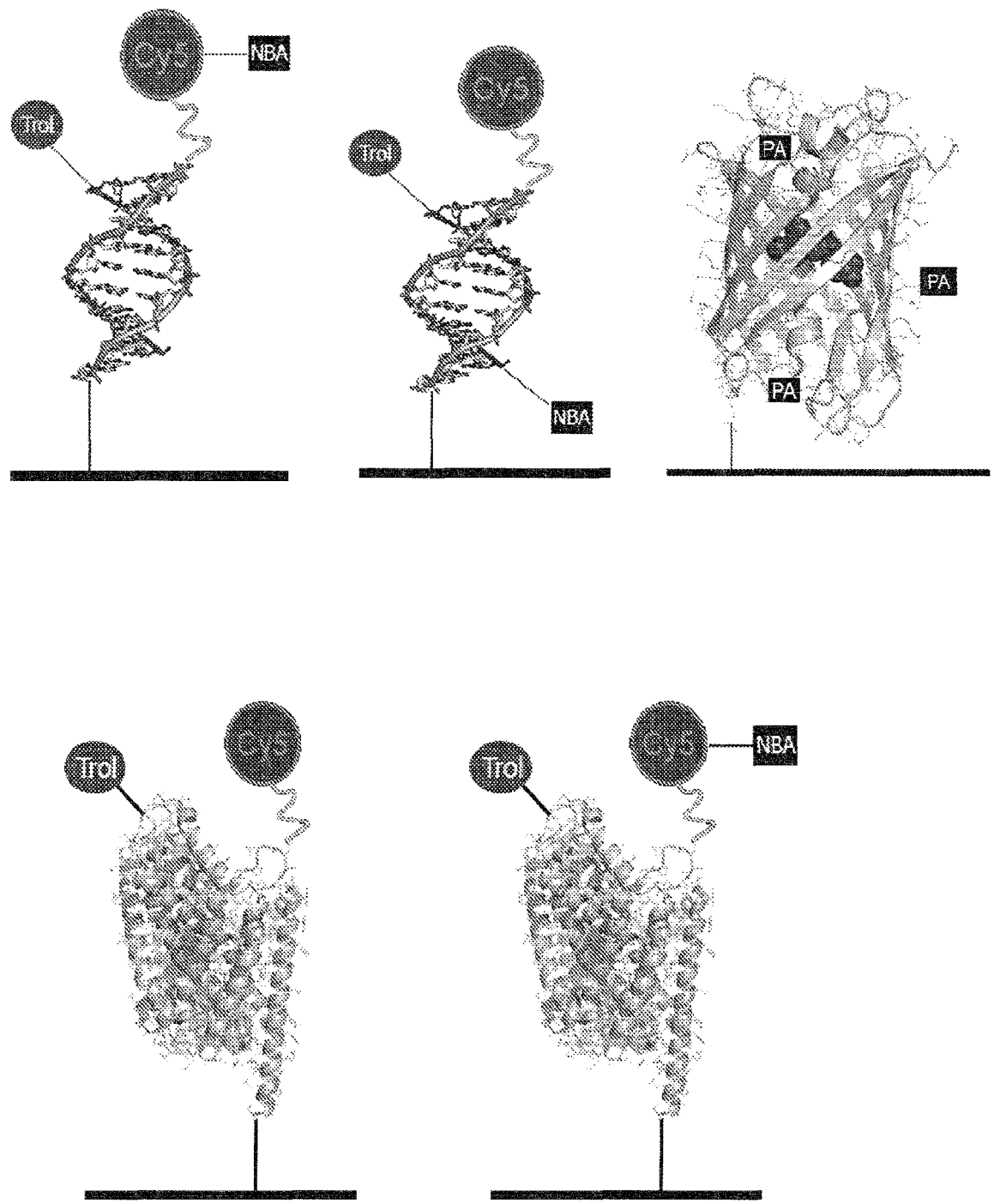

FIG. 17 presents experimental data demonstrating the utility of achieving proximity of more than one protective agent to a fluorescing species using Cy5-labeled DNA as an example. As shown in FIG. 9, the Cy5-Trolox conjugate (orange) is greatly improved in lifetime over the no-PA Cy5 control (>10-fold). By adding a second protective agent (either NBA and Trolox) in proximity (within 30 Å) of the Cy5-Trolox fluorophore, an additional improvement in fluorophore lifetime ($t_{on}$) is observed. In the case of a Trolox (purple), the additional improvement is >1.3-fold. In the case of NBA (green) the additional improvement is >2-fold. Thus, the total improvement achieved was >20-fold over the parent compound. Drawings depicting other exemplary strategies for achieving proximity of more than one protective agent to a fluorescing species.

Figure 18:
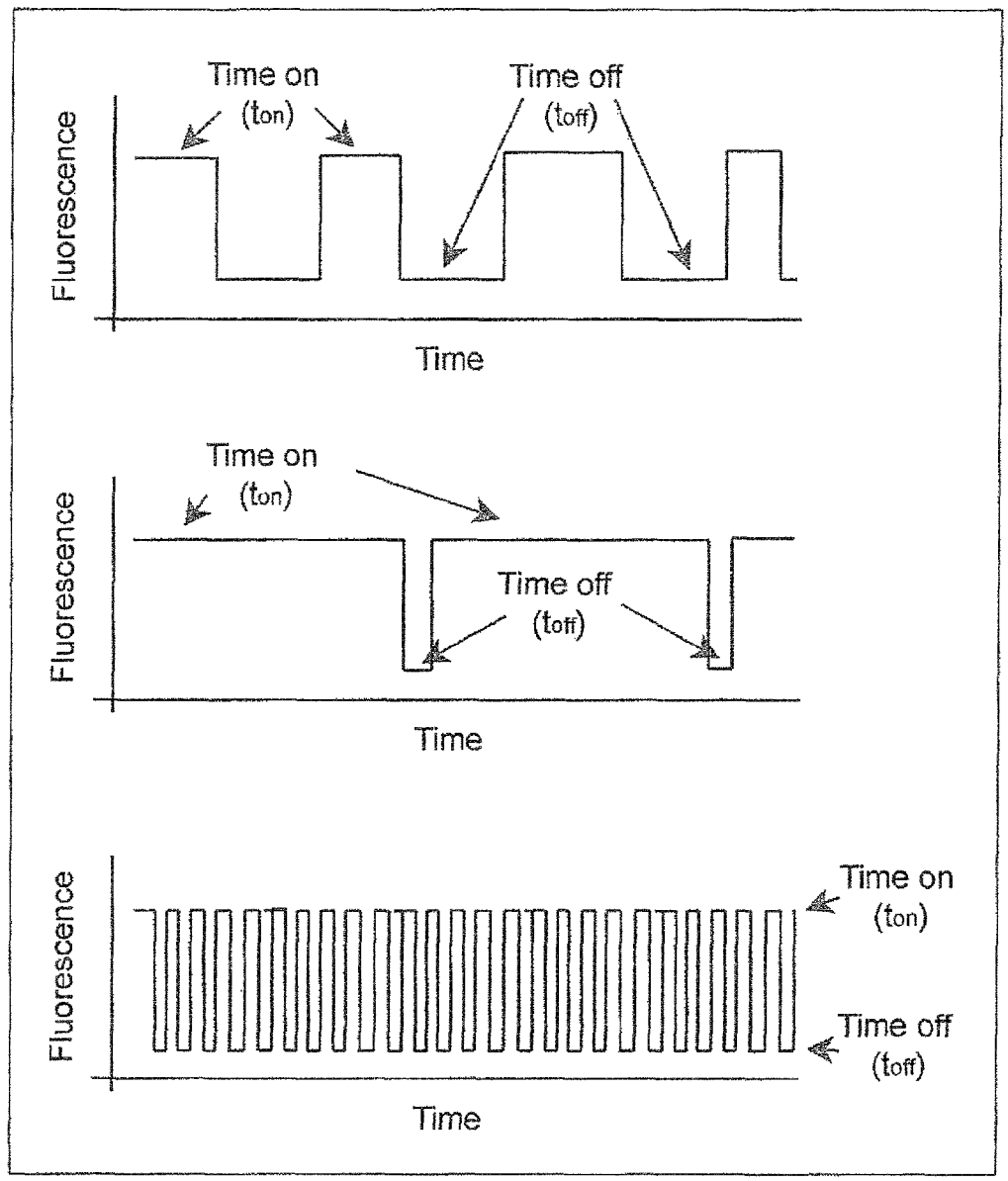
FIG. 18. Schematic representation of the tuning of fluorescence behavior. The relevant parameters are the lifetimes in fluorescing states (Time on, $t_{on}$) and non-fluorescing states (Time off, $t_{off}$) and the fluorescence intensities. The present invention describes how one can change the intrinsic fluorescent properties of a fluorescing species by controlling fluorophore proximity to one or more protective agents. Such strategies can be used to achieve long-lasting fluorescing states and shorter dark states or shorter-lived fluorescent and dark states depending on the specific PAs employed and their proximity to the fluorescent species. Similar strategies may also be used to control the quantum yield (brightness) of a fluorophore under a given illumination intensity.

FIG. 18 shows a schematic representation of the tuning of fluorescence behavior. The relevant parameters are the lifetimes in fluorescing states (Time on, $t_{on}$) and non-fluorescing states (Time off, $t_{off}$) and the fluorescence intensities. The present invention describes how one can change the intrinsic fluorescent properties of a fluorescing species by controlling fluorophore proximity to one or more protective agents. Such strategies can be used to achieve long-lasting fluorescing states and shorter dark states or shorter-lived fluorescent and dark states depending on the specific PAs employed and their proximity to the fluorescent species. Similar strategies may also be used to control the quantum yield (brightness) of a fluorophore under a given illumination intensity.

The lifetimes in either state are determined by stochastic processes that depend on intrinsic and extrinsic factors. The characteristic switching behaviors of fluorescing species may be unwanted in the case of single-molecule FRET imaging of a biological process, where non-fluorescing states may be uninformative. Alternatively, the characteristic switching behaviors of fluorescing species may be leveraged for determining that only one fluorophore is under observation (identified by single-step photobleaching), for determining the location of a single fluorophore through FIONA and super-resolution imaging techniques (Yildez A et al. *Science* Vol 300(5628) pg. 2061-5 (2003); Churchman L S et al. Biophys 3 Vol. 90(2) pg. 668-71 (2006); and Bates M et al. Science Vol. 317(5845) pg. 1749-53 (2007)), or for other imaging or computational purposes. In cases where switching behaviors are not wanted such as "molecular EKG" approaches (Blanchard S C Curr Opin Struct. Biol Vol. 19(1) pg. 103-9 (2009)), $t_{on}$ can be maximized by using one or more PAs and PA linkage strategies that extend the lifetime of fluorescence, while simultaneously $t_{off}$ should be minimized (center panel). In cases where switching behaviors are desired such as FIONA and super-resolution imaging, rapid switching may be beneficial to the experiment in which case one or more PAs and PA linkage strategies should be employed to control the frequency of switching behavior and the total time that switching behaviors are observed. In the case of super-resolution imaging, fast switching for extended periods can greatly reduce the total time needed to perform the experiment and to obtain high-resolution data.

Figure 19:
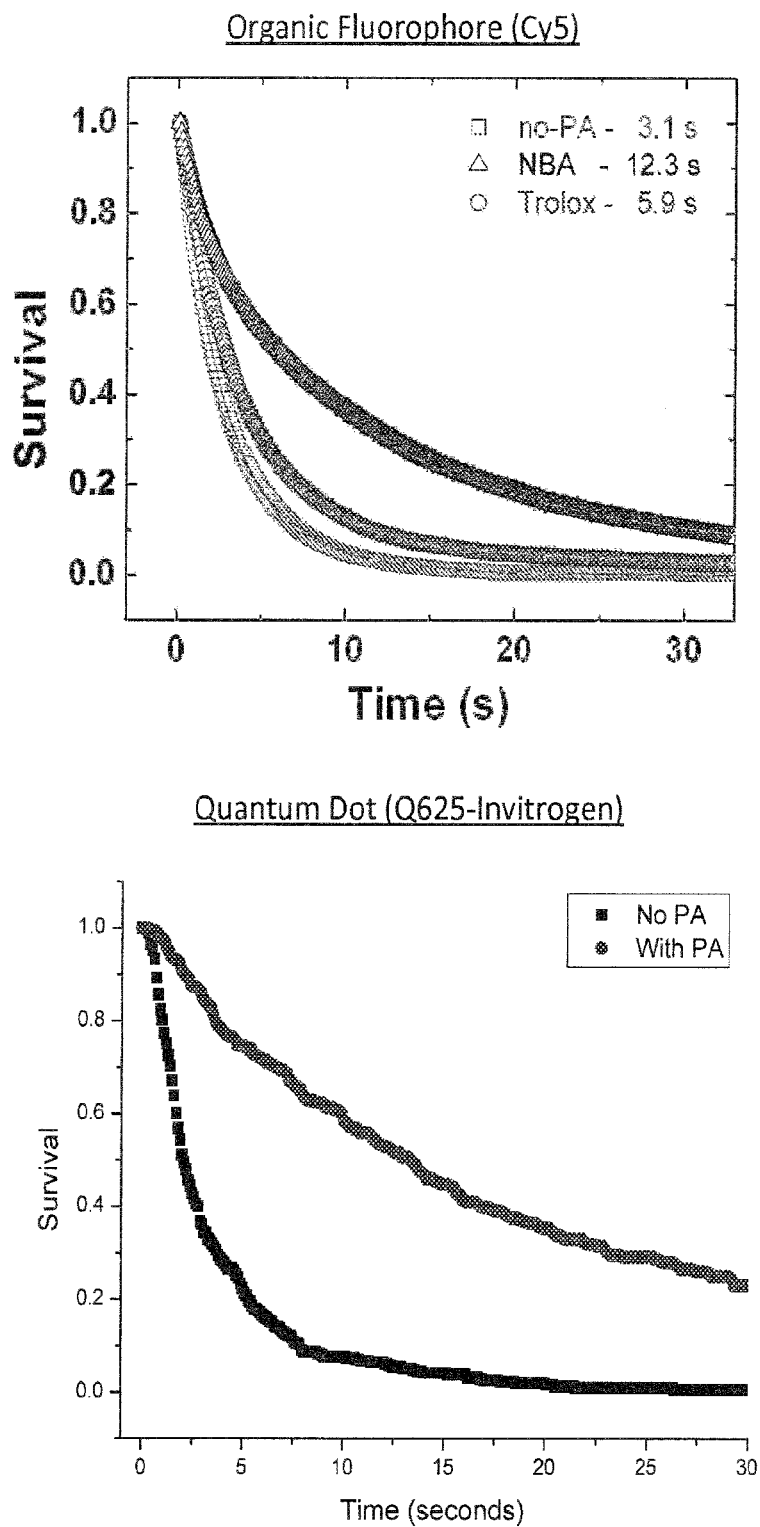
FIG. 19. Experimental data showing that under conditions similar to those found in the cell (buffers saturated (1-2 mM) with molecular oxygen ($O_2$)) fluorophore-PA proximity extends the lifetime of fluorescence ($t_{on}$). (Upper panel) Specific, exemplary fluorophore-PA conjugates under direct excitation (namely Cy5-trolox and Cy5-NBA) (Lower panel) Quantum dots bathed in a solution of 1 mM Trolox, COT and NBA. In each case the distribution of fluorescence lifetimes (ton) were fit to an exponential process.

FIG. 19 presents experimental data showing that under conditions similar to those found in the cell (buffers saturated (1-2 mM) with molecular oxygen (OD) fluorophore-PA proximity extends the lifetime of fluorescence ($t_{on}$). (Upper panel) Specific, exemplary fluorophore-PA conjugates under direct excitation (namely Cy5-trolox and Cy5-NBA) (Lower panel) Quantum dots bathed in a solution of 1 mM Trolox, COT and NBA. In each case the distribution of fluorescence lifetimes (ton) were fit to an exponential process.

Reaction Procedures for the Synthesis of Dye-Protective Agent Constructs:

Analytical Equipment:

HPLC: All separations involved a mobile phase of 10 mM triethylammonium acetate in water, pH 8.1 (solvent A)/acetonitrile (solvent B). Preparative, semipreparative, and analytical HPLC separations were performed using a Varian Prep-Star solvent delivery system equipped with a Varian 335 ProStar PDA detector and Varian Pursuit XRS C-18 10µ column, 250 mm in length and 21.2 mm in diameter (semi-prep), or Pursuit XRS C-18 3µ column 250 mm in length and 4.6 mm in diameter (analytical). Separations were performed at flow rates of 20 mL/min for semiprep and 1 mL/min for analytical with PDA monitoring from 215 to 900 nm. Unless otherwise mentioned, all separations were run with the following gradient: 0-2.5 min (25% B); 2.5-12.5 min (25-95% B); 12.5-15 min (95%). All separations were complete after 15 min. All retention times (rt) are for the analytical column following purification.

ESMS: Electrospray mass spectroscopy analysis was obtained on a Waters SQ mass spectrometer.

Exemplary reaction of a bis-(NHS) reactive cyanine dye with a protective agent.

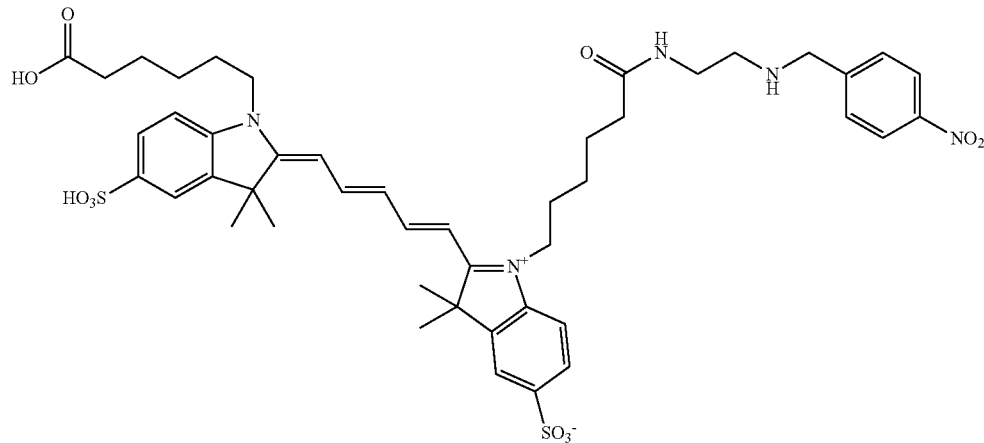

To a solution of water (130 µL) and 500 mM aqueous potassium borate (20 µL) was added bis-NHS-Cy5 (1 mg, 1.1 µmol) in DMSO (50 µL), immediately followed by NBA-NH$_2$ (2.5 µL of a 500 mM solution in DMSO). The resulting reaction was vortexed and then sat at 37° C. for 10 min at which point it was quenched by the addition of 250 mM aqueous potassium hydroxide (10 µL). The entire reaction mixture was then injected directly onto the HPLC for purification (rt)=6.15 min. The desired compound (NBA-Cy5-COOH) was obtained as a dark blue powder following lyophilization.

Exemplary Activation of a Protective Agent-Dye-Acid as an NHS Ester.

To a solution of NBA-Cy5-COOH (10 nmol) in dry DMF (10 µL) was added SbTMU (90 nmol) in dry DMF (25 µL) followed by diisopropylethylamine (DIEA, 80 nmol). The reaction was vortexed and then sat at ambient temperature for 30 min at which point ethyl acetate (1.2 mL) was added to affect an immediate precipitation. The mixture was centrifuged and the supernatant was decanted. The remaining pellet was triturated with ethyl acetate (×2), each time removing the supernatant after centrifugation. The crude product was a single peak by HPLC (rt=9.96 min) and was used without further purification.

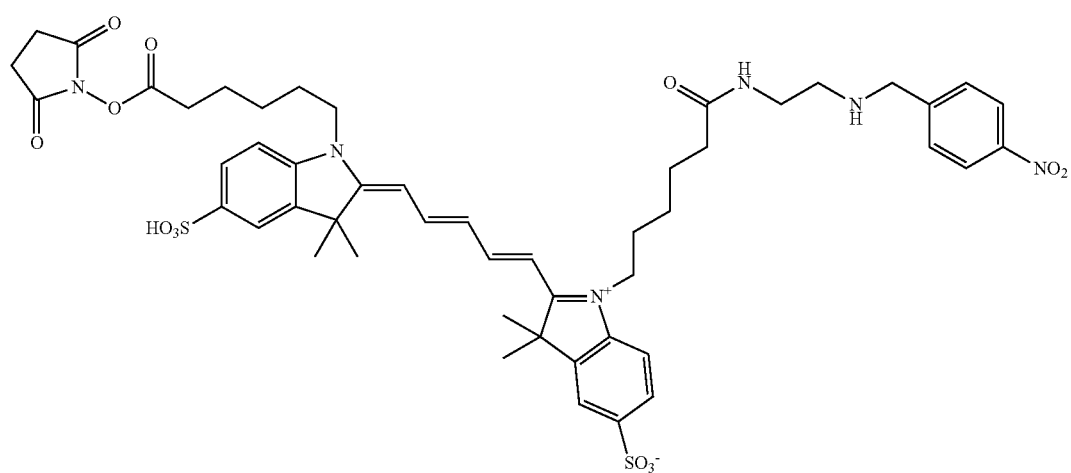

Exemplary Activation of a Protective Agent-Dye-Acid as a Maleimide.

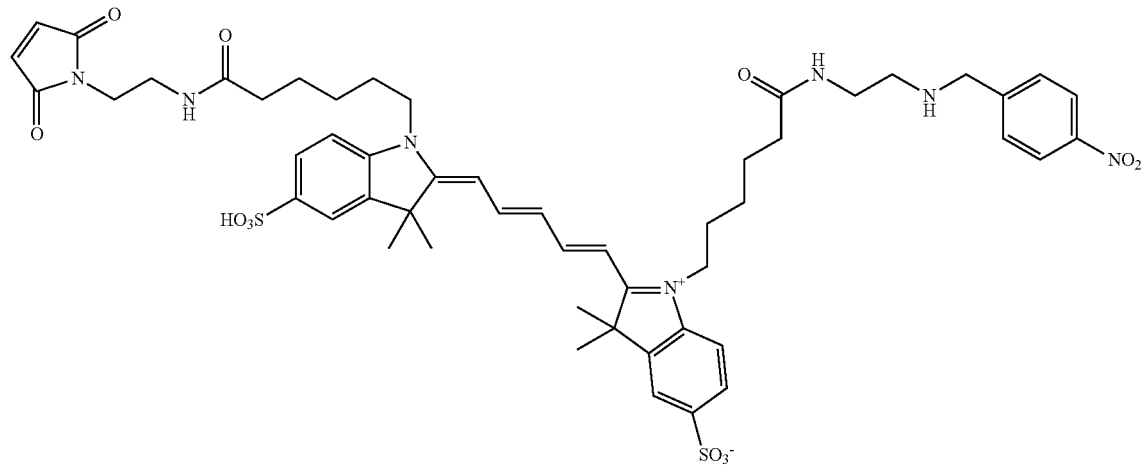

To a solution of N-(2-aminoethyl)maleimide)trifluoroacetate salt (500 nmol) in dry DMF (50 µL) was added a solution of NBA-Cy5-NHS (5 nmol) in dry DMF (5 µL) followed by a solution of DIEA (250 nmol) in dry DMF (50 µL). The reaction was vortexed and then sat at ambient temperature for 30 min at which point ethyl acetate (1.2 mL) was added to affect an immediate precipitation. The mixture was centrifuged and the supernatant was decanted. The remaining pellet was triturated with ethyl acetate (×2), each time removing the supernatant after centrifugation. The crude product was a single peak by HPLC, (rt=9.05 min) and was used without further purification. HRMS: Calcd. for $C_{52}H_{63}N_7O_{12}S_2$ [M+Na]$^+$1064.3874. Found 1064.3849.

Similar protocols were followed to provide the Trolox derivatives:

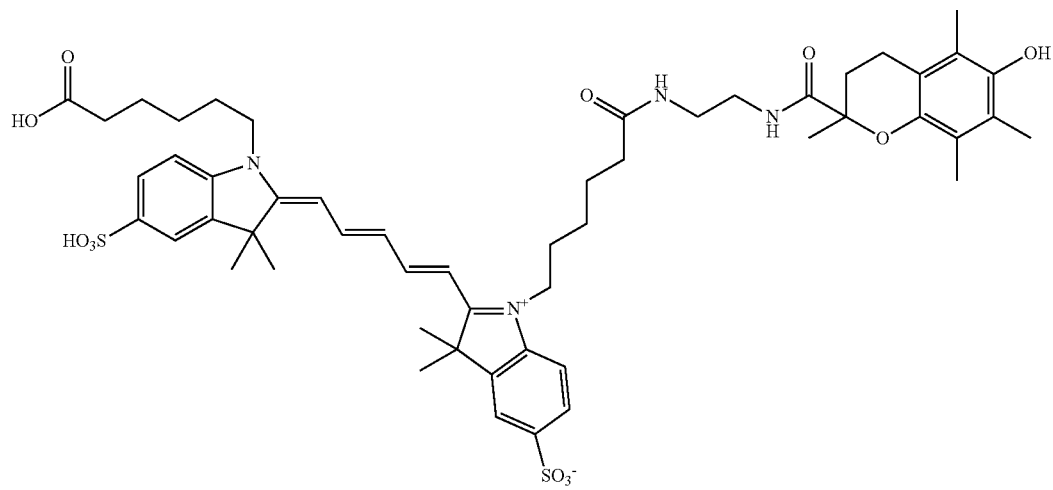

Trolox-Cy5-COOH was obtained as a dark blue powder following lyophilization, rt=8.54 min.

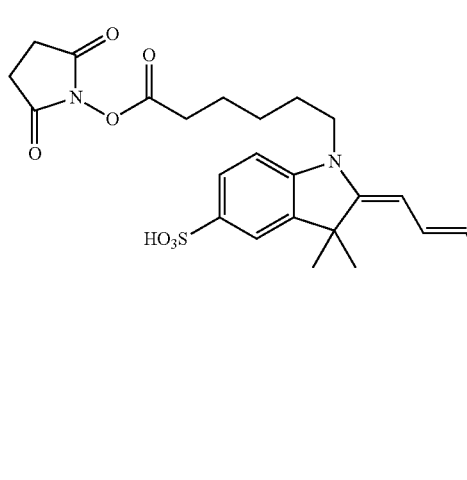
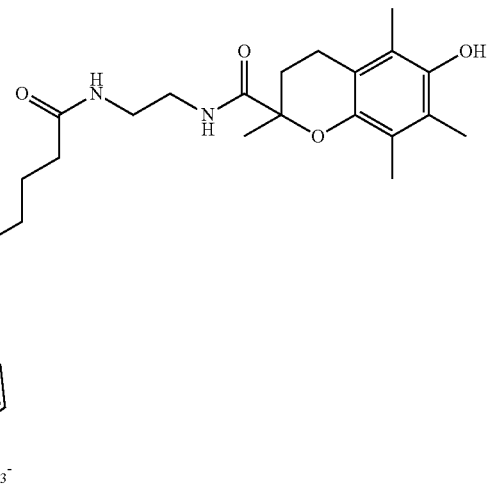

Trolox-Cy5-NHS was obtained as a dark blue powder following lyophilization, rt=9.13 min. HRMS: Calcd. for $C_{57}H_{71}N_5O_{14}S_2$ [M+Na]$^+$ 1136.4337. Found 1136.4335.

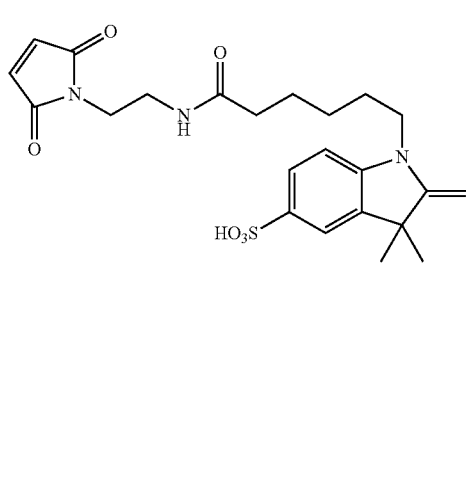

Trolox-Cy5-Mal was obtained as a dark blue powder following lyophilization, rt=9.30 min.

What is claimed is:

1. A composition comprising a fluorophore having attached thereto at least one protective agent moiety selected from cyclooctatetraene (COT), Trolox, p-nitrobenzyl alcohol (NBA), chloramphenicol, n-propyl gallate, and 1,4-diazabicyclo[2.2.2]octane (DABCO), wherein the at least one protective agent moiety is attached covalently to the fluorophore either directly or via a linker.

2. The composition of claim 1, wherein at least two protective agent moieties are attached to said fluorophore.

3. The composition of claim 1, wherein said linker has a size of less than 1,000 Daltons.

4. The composition of claim 1, wherein said composition is conjugated to a biomolecule or a surface of a bulk solid by either a direct bond or by a conjugating group connecting said biomolecule or surface and at least one of the fluorophore or said at least one protective agent moiety.

5. The composition of claim 1, wherein said fluorophore exhibits an emission wavelength greater than 594 nm.

6. A method for performing single-molecule Fluorescence Resonance Energy Transfer (FRET), the method comprising measuring the FRET efficiency of a labeled biomolecule comprised of a biomolecule attached to a donor fluorophore and acceptor fluorophore, wherein said donor and/or acceptor fluorophores are attached covalently either directly or via a linker to one or more protective agent moieties selected from cyclooctatetraene (COT), Trolox, p-nitrobenzyl alcohol (NBA), chloramphenicol, n-propyl gallate, and 1,4-diazabicyclo[2.2.2]octane (DABCO).

7. A method for detecting a cellular process in an organism using fluorescence, the method comprising (i) administering to said organism a targeting probe comprising a biomolecule possessing a targeting portion thereon, at least one fluorophore, and at least one protective agent moiety selected from cyclooctatetraene (COT), Trolox, p-nitrobenzyl alcohol (NBA), chloramphenicol, n-propyl gallate, and 1,4-diazabicyclo[2.2.2]octane (DABCO), wherein said protective agent moiety is attached covalently either directly or via a linker to said fluorophore such that the protective agent moiety enhances the photophysical properties of said fluorophore, and ii) detecting said targeting probe using fluorescence in said organism.

* * * * *